US007384913B2

(12) United States Patent
Oko et al.

(10) Patent No.: US 7,384,913 B2
(45) Date of Patent: Jun. 10, 2008

(54) PT32 SPERM PROTEIN, SPERM C-YES, OOCYTE CYTOPLASMIC C-YES, AND USES THEREOF

(75) Inventors: Richard Oko, Kingston (CA); Peter Sutovsky, Columbia, MO (US)

(73) Assignees: Queen's University at Kingston, Kingston, Ontario (CA); Oregon Health Sciences University, Portland, OR (US)

( * ) Notice: Subject to any disclaimer, the term of this patent is extended or adjusted under 35 U.S.C. 154(b) by 0 days.

(21) Appl. No.: 11/224,577

(22) Filed: Sep. 12, 2005

(65) Prior Publication Data

US 2006/0240512 A1 Oct. 26, 2006

Related U.S. Application Data

(62) Division of application No. 09/864,291, filed on May 25, 2001, now Pat. No. 6,995,252.

(60) Provisional application No. 60/206,979, filed on May 25, 2000.

(30) Foreign Application Priority Data

May 25, 2000 (CA) .................................. 2307128

(51) Int. Cl.
*A61K 38/00* (2006.01)
*C07K 14/00* (2006.01)
(52) U.S. Cl. .................. 514/2; 530/350; 530/387.1; 536/23.5; 435/320.1; 435/325; 435/69.7
(58) Field of Classification Search .................. 514/2; 435/320.1, 325, 69.7; 530/350, 387.1; 536/23.5
See application file for complete search history.

(56) References Cited

U.S. PATENT DOCUMENTS

| 5,672,488 | A | 9/1997 | Dean ........................ 435/69.3 |
| 5,753,231 | A | 5/1998 | Herr et al. ................ 424/185.1 |
| 5,770,363 | A | 6/1998 | Brown ........................ 435/6 |
| 5,843,754 | A | 12/1998 | Susko-Parrish et al. ...... 435/450 |
| 5,897,988 | A | 4/1999 | Huszar ........................ 435/2 |
| 5,916,768 | A | 6/1999 | Dean ........................ 435/69.3 |
| 5,945,577 | A | 8/1999 | Stice et al. .................... 800/24 |
| 5,952,222 | A | 9/1999 | Rosenkrans, Jr. et al. .. 435/325 |
| 5,989,549 | A | 11/1999 | Sullivan et al. .......... 424/184.1 |
| 5,989,550 | A | 11/1999 | Harris et al. .............. 424/185.1 |
| 5,994,619 | A | 11/1999 | Stice et al. .................... 800/21 |
| 6,011,197 | A | 1/2000 | Strelchenko et al. .......... 800/24 |
| 6,013,770 | A | 1/2000 | Reeves et al. .............. 530/367 |
| 6,013,857 | A | 1/2000 | Deboer et al. ................ 800/15 |
| 6,034,212 | A | 3/2000 | Sudol et al. ................ 530/324 |
| 6,045,799 | A | 4/2000 | Reeves et al. ........... 424/192.1 |
| 6,197,940 | B1 | 3/2001 | Klinefelter |
| 6,211,429 | B1 | 4/2001 | Machaty et al. .............. 800/24 |
| 6,585,982 | B1 | 7/2003 | Grondahl et al. |
| 6,593,139 | B1 | 7/2003 | Yanagimachi et al. |
| 6,610,543 | B2 | 8/2003 | Choay et al. |
| 6,641,526 | B1 | 11/2003 | Wakayama et al. |
| 6,716,812 | B1 | 4/2004 | Fraser et al. |
| 6,737,272 | B2 | 5/2004 | Kuo et al. |
| 6,965,016 | B2 | 11/2005 | Klinefelter |
| 2002/0028509 | A1 | 3/2002 | Choay et al. |
| 2003/0131371 | A1 | 7/2003 | Choi et al. |
| 2005/0025750 | A1 | 2/2005 | Fissore et al. |

FOREIGN PATENT DOCUMENTS

| WO | WO 97/40386 | 10/1997 |
| WO | WO 00/40700 | 7/2000 |
| WO | WO 01/30970 A2 | 5/2001 |
| WO | WO 01/70261 | 9/2001 |
| WO | WO 03/040354 A1 | 5/2003 |
| WO | WO 2004/060056 A2 | 7/2004 |

OTHER PUBLICATIONS

Abassi, Y.A., et al., "Evidence that Src-type tryosine kinase activity is necessary for initiation of calcium release at fertilization in sea urchin eggs," *Dev. Biol.* 218:206-210, Plenum Press (Feb. 2000).

Battaglia, D.E., et al., "Failure of oocyte activation after intracytoplasmic sperm injection using round-headed sperm," *Fertil. Steril.* 68:118-122, Elsevier Science (1997).

Bellvé, A.R., et al., "The perinuclear matrix as a structural element of the mouse sperm nucleus," *Biol. Repord.* 47:451-465, Society for the Study of Reproduction (1992).

Carroll, D.J., et al., "Identification of PLCγ-dependent and independent events during fertilization of sea urchin eggs," *Dev. Biol.* 206:232-247, Plenum Press (1999).

Chen, H.I., et al., "The WW domain of Yes-associated protein binds a proline-rich ligand that differs from the consensus established for Src homology 3-binding modules," *Proc. Natl. Acad. Sci. USA* 92:7819-7823, National Academy of Sciences (1995).

Chen, H.I., et al., "Characterization of the WW domain of Human Yes-associated protein and its polyproline-containing ligands," *J. Biol. Chem.* 272:17070-17077, American Society for Biochemistry and Molecular Biology, Inc. (1997).

Courtens, J.L., et al., "The perinuclear substance of boar, bull ram and rabbit spermatozoa," *J. Ultrastruct. Res.* 57:54-64, Academic Press, Inc. (1976).

(Continued)

*Primary Examiner*—Chih-Min Kam
(74) *Attorney, Agent, or Firm*—Quarles & Brady LLP

(57) ABSTRACT

The perinuclear theca 32 (PT32) protein is disclosed and shown to interact with tyrosine kinase c-Yes. PT32, c-Yes, fragments thereof, and molecules that bind thereto can be used in methods of enhancing fertility, treating or diagnosing diminished fertility and abnormal spermiogenesis, in providing contraception, and in identifying contraceptive and fertility-enhancing agents. Transgenic, non-human animals also are disclosed.

13 Claims, 15 Drawing Sheets

OTHER PUBLICATIONS

Figure 1:
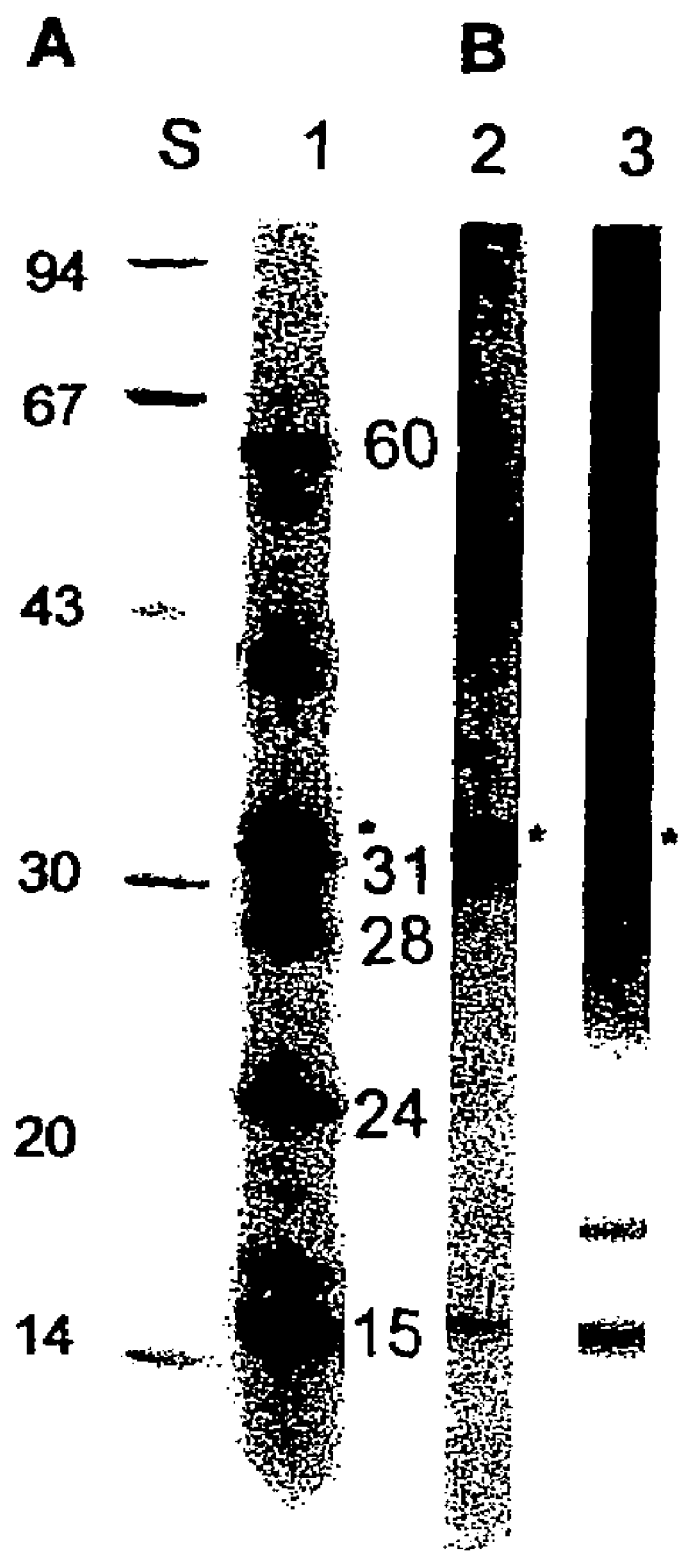

Edirisinghe, W.R., et al., "Cytogenetic analysis of unfertilized oocytes following intracytoplasmic sperm injection using spermatozoa from a globozoospermic man," *Hum. Reprod.* 13:3094-3098, Oxford University Press (1998).

Einbond, A., et al., "Towards prediction of cognate complexes between the WW domain and proline-rich ligand," *FEBS Lett.* 384:1-8, Elsevier Science B.V. (1996).

Escalier, D., "Failure of differentiation of the nuclear-perinuclear skeletal complex in the round-headed human spermatozoa," *Int. J. Dev. Biol.* 34:287-297, UBC Press (1990).

Giusti, A.F., et al., "Evidence that a starfish egg Src family tyrosine kinase associates with PLC-γ1 SH2 domains at fertilization," *Dev. Biol.* 208:189-199, Plenum Press (Apr. 1999).

Giusti, A.F., et al., "Evidence that fertilization activates starfish eggs by sequential activation of a Src-like kinase and phospholiphase C gamma," *J. Biol. Chem.* 275:16788-16794, American Society for Biochemistry and Molecular Biology, Inc. (Jun. 2000).

Gordo, A.C., et al., "Injection of sperm cytosolic factor into mouse metaphase II oocytes induces different developmental fates," *Biol. Reprod.* 62:1370-1379, Society for the Study of Reproduction (May 2000).

Hess, H., et al., "The protein complexity of the cytoskeleton of bovine and human sperm heads: the identification and characterization of cyclin II," *Exp. Cell Res.* 218:174-182, Academic Press, Inc. (1995).

Hess, H., et al., "Molecular characterization of mammalian cyclin, a basic protein of the sperm head cytoskeleton," *J. Cell Biol.* 122:1043-1052, Rockefeller University Press (1993).

Hewitson, L.C., et al., "Microtubule and chromatin configurations during rhesus intracytoplasmic sperm injection: successes and failures," *Biol. Reprod.* 55:271-280, Society for the Study of Reproduction (1996).

Hewitson, L., et al., "Unique checkpoints during the first cell cycle of fertilization after intracytoplasmic sperm injection in rhesus monkeys," *Nat. Med.* 5:431-433, Nature Publishing Company (Apr. 1999).

Hurst, S., et al., "Expression of testis-specific putative actin-capping protein associated with the developing acrosome during rat spermiogenesis," *Mol. Reprod. Dev.* 49:81-91, Wiley-Liss, Inc. (1988).

Kay, B.K., et al., "The importance of being proline: the interaction of proline-rich motifs in signaling proteins with their cognate domains," *FASEB J.* 14:231-241, Federation of American Societies for Experimental Biology (Feb. 2000).

Kimura, Y., et al., "Analysis of mouse oocyte activation suggests the involvement of sperm perinuclear material," *Biol. Reprod.* 58:1407-1415, Society for the Study of Reproduction (1998).

Korley, R., et al., "Analysis of protein composition of the mouse sperm perinuclear theca and characterization of its major protein constituent," *Biol. Reprod.* 57:1426-1432, Society for the Study of Reproduction (1997).

Leclerc, P., et al., "Distribution and localization of calmodulin-binding proteins in bull spermatozoa," *Biol. Reprod.* 62:1875-1881, Society for the Study of Reproduction (Jun. 2000).

Lee, S.C., et al., "Sperm factor initiates capacitance and conductance changes in mouse eggs that are more similar to fertilization than $IP_3$-, or $Ca^{3x}$- induced changes," *Dev. Biol.* 232:127-148, Plenum Press (Apr. 2001).

Longo, F.J., et al., "Basic proteins of the perinuclear theca of mammalian spermatozoa and spermatids: A novel class of cytoskeletal elements," *J. Cell Biol.* 105:1105-1120, Rockefeller University Press (1987).

Machaty, Z., et al., "Porcine oocyte activation induced by a cytosolic sperm factor," *Mol. Reprod. Dev.* 57:290-295, Wiley-Liss, Inc. (Nov. 2000).

Mehlmann, L., et al., "SH2 domain-mediated activation of phospholipase C is not required to initiate $CA^{2-}$ release at fertilization in mouse egss," *Dev. Biol.* 203:221-232, Plenum Press (1998).

Okitsu, O., et al., "Activation of bovine oocyte matured in vitro by injection of bovine and human spermatozoa or their cytosolic fractions," *Zygote* 9:89-95, Cambridge University Press (Feb. 2001).

Oko, R. and Clermont, Y., "Isolation, structure and protein composition of the perforatorium of rat spermatozoa," *Biol. Reprod.* 39:673-687, Society for the Study of Reproduction (1988).

Oko, R., et al., "Regional differences in composition of the perforatorium and outer periacrosomal layer of the rat spermatozoa as revealed by immunocytochemistry," *Am. J. Anat.* 188:64-73, Wiley-Liss, Inc. (1990).

Oko, R. and Clermont, Y., "Origin and distribution of perforatorial proteins during spermatogenesis of the rat: an immunocytochemical study," *Anat. Rec.* 230:489-501, Wiley-Liss, Inc. (1991).

Oko, R. and Maravei, D., "Protein composition of the perinuclear theca of bull spermatozoa," *Biol. Reprod.* 50:1000-1014, Society for the Study of Reproduction (1994).

Oko, R., et al., "A novel testicular protein, with sequence similarities to a family of lipid binding proteins, is a major component of the rat sperm perinuclear theca," *Dev. Biol.* 166:235-245, Plenum Press (1994).

Oko, R., et al., "Developmental expression and possible role perinuclear theca proteins in mammalian spermatozoa," *Reprod. Fertil. Dev.* 7:777-797, CSIRO (1995).

Oko, R., et al., "Distribution and possible role perinuclear theca proteins during bovine spermiogenesis," *Microsc. Res. Tech.* 32:520-532, Wiley-Liss, Inc. (1995).

Oko, R., et al., "Germ cell-specific DNA and RNA binding proteins p48/52 are expressed at specific stages of male germ cell development and are present in the chromatoid body," *Mol. Reprod. Dev.* 44:1-13, Wiley-Liss, Inc. (1996).

Oko, R., "Occurrence and formation of cytoskeletal proteins in mammalian spermatozoa," *Andrologia* 30:193-206, Blackwell Wissenschafts Verlag GmbH (1998).

Oko, R. and Clermont, Y., "Spermiogenesis," in: *Encyclopedia of Reproduction* vol. 4, Knobil, E. and Neill, J.D., eds., Academic Press, Inc., San Diego, California, pp. 602-609 (1998).

Oko, R., et al., "The sperm head cytoskeleton," in: *Proceedings of the VIIth International Congress of Andrology*, Robaire, B., et al., eds., Medimond Publishing Company, Englewood, New Jersey, pp. 37-51 (Jun. 2001).

Parrington, J., "Does a soluble sperm factor trigger calcium release in the egg at fertilization?"*J. Andrology* 22:1-11, Allen Press (Jan. 2001).

Parrington, J., et al., "The soluble mammalian sperm factor protein that triggers $Ca^{2x}$oscillations in eggs: evidence for expressison of mRNA(s) coding for sperm factor protein(s) in spermatogenic cells," *Biol. Cell.* 92:267-275, Elsevier Science (Jul. 2000).

Parrington, J., et al., "Calcium oscillations in mammalian eggs triggered by a soluble sperm protein," *Nature* 379:364-367, Macmillan Journals Ltd. (1996).

Perry, A.C.F., et al., "A novel trans-complementation assay suggests full mammalian oocyte activation is coordinately initiated by multiple submembrane sperm compartments," *Biol. Reprod.* 60:747-755, Society for the Study of Reproduction (Mar. 1999).

Perry, A.C., et al., "Mammalian oocyte activation by the synergistic action of discrete sperm head components: induction of calcium transients and involvement of proteolysis," *Dev. Biol.* 217:386-393, Academic Press, Inc. (Jan. 2000).

Pouresmaeili, F., et al., "Molecular cloning and structural analysis of the gene encoding PERF 15 protein present in the perinuclear theca of the rat spermatozoa," *Biol. Reprod.* 57:655-659, Society for the Study of Reproduction (1997).

Prochazka, R. and Fiser, P.S., "Behaviour of blastomere nuclei fused to mouse oocytes is affected by oocyte enucleation and age," *Reprod. Nutr. Dev.* 35:695-701, EDP Sciences (1995).

Runft, L.L., et al., "Sperm extract injection into ascidian eggs signals $Ca^{2+}$release by the same pathway as fertilization," *Development* 127:3227-3236, Company of Biologists Ltd. (Aug. 2000).

Runft, L.L., et al., "Calcium release at fertilization of *Xenopus* eggs requires type I IP(3) receptors, but not SH2 domain-mediated activation of PLCγ or G (q)—mediated activation of PLCβ," *Dev. Biol.* 214:399-411, Plenum Press (Oct. 1999).

Rybouchkin, A., et al., "Analysis of the oocyte activating capacity and chromosomal complement of round-headed human spermatozoa by their injection into mouse oocyte," *Hum. Reprod.* 11:2170-2175, Oxford University Press (1996).

Rybouchkin, A.W., et al., "Fertilization and pregnancy after assisted oocyte activation and intracytoplasmic sperm injection in a case of round-headed sperm associated with deficient oocyte activation capacity," *Fertil. Steril.* 68:1144-1147, American Society for Reproductive Medicine (1997).

Sato, Y., et al., "Adenophostin, a potent agonist of the inositol 1, 4, 5-triphosphate receptor, is useful for fertilization of mouse oocytes injected with round spermatids leading to normal offspring, *Bio. Reprod.* 58:867-873, Society for the Study of Reproduction (1998).

Schmitt, M.C., et al., "A novel, testis-specific member of the cellular lipophilic transport protein superfamily, deduced from a complementary deoxyribonucleic acid clone," *Biol. Reprod.* 51:239-245, Society for the Study of Reproduction (1994).

Schultz, R.M. and Kopf, G.S., "Molecular basis of mammalian egg activation," *Curr. Topics Dev. Biol.* 30:21-62, Academic Press, Inc. (1995).

Sette, C., et al., "Involvement of phospholipase Cγl in mouse egg activation of mouse eggs by microinjection of a truncated c-kit tyrosine kinase present in spermatozoa," *J. Cell Biol.* 124:1063-1074, Rockefeller University Press (1998).

Shearer, J., et al., "Role of phospholipase C gamma at fertilization and during mitosis in sea urchin eggs and embryos," *Development* 126:2273-2284, Company of Biologists Ltd. (May 1999).

Sofikitis, N., et al., "The early haploid gamete develops a capacity for fertilization after the coalescence of the proacrosomal granules," *Hum. Reprod.* 12:2713-2719, Oxford University Press (1997).

Sudol, M., "Yes-associated protein (YAP65) is a proline-rich phosphoprotein that binds to the SH3 domain of the Yes proto-oncogene product," *Oncogene* 9:2145-2152, Stockton Press (1994).

Sudol, M., et al., "Characterization of a novel protein-binding module—the WW domain," *FEBS Lett.* 369:67-71, Elsevier Science B.V. (1995).

Sudol, M., "From Src homology domains to other signaling modules: proposal of the protein recognition code," *Oncogene* 17:1469-1474, Stcokton Press (1998).

Sudol, M., et al., "New wrinkles for an old domain," *Cell* 103:1001-1004, Cell Press (Dec. 2000).

Sutovsky, P., et-al., "Intracytoplasmic sperm injection for Rhesus monkey fertilization results in unusual chromatin, cytoskeletal, and membrane events, but eventually leads to pronuclear development and sperm aster assembly,"*Hum. Reprod.* 11:1703-1712, Oxford University Press (1996).

Sutovsky, P., et al., "Fate of the sperm mitochondria, and the incorporation, conversion, and disassembly of the sperm tail structures during bovine fertilization," *Biol. Reprod.* 55:1195-1205, Society for the Study of Reproduction (1996).

Sutovsky, P., et al., "The removal of the sperm perinuclear theca and its association with the bovine oocyte surface during fertilization," *Dev. Biol.* 188:75-84, Plenum Press (1997).

Sutovsky, P., et al., "On-stage selection of single round spermatids using a vital, mitochondrion-specific fluorescent probe MitoTracker™ and high resolution differential interference contrast microscopy," *Hum. Reprod.* 14:2301-2312, Oxford University Press (Sep. 1999).

Sutovsky, P. and Schatten, G., "Paternal contributions to the mammalian zygote: fertilization after sperm-egg fusion," *Int. Rev. Cytol.* 195:1-65, Academic Press, Inc. (Nov. 1999).

Sutovsky, P., et al., "Ubiquitin-based sperm assay for the diagnosis of male factor infertility," *Hum. Reprod.* 16:250-258, Oxford University Press (Feb. 2001).

Swann, K., "A cytosolic sperm factor stimulates repetitive calcium increases and mimics fertilization in hamster eggs," *Development* 110:1295-1302, Company of Biologists Ltd. (1990).

Talian, J.C., et al., "A rapid procedure for preparing fluorescein-labelled specific antibodies from whole antiserum: its use in analyzing cytoskeletal architecture," *J. Cell Biol.* 97:1277-1282, Rockefeller University Press (1983).

Tanaka, H., et al., "Isolation and characterization of cDNA clones specifically expressed in testicular germ cells," *FEBS Lett.* 355:4-10, Elsevier Science B.V. (1994).

Tang, T.S., et al., "$Ca^{2+}$ oscillations induced by a cytosolic sperm protein factor are mediated by a maternal machinery," *Development* 127:1142-1150, Company of Biologists Ltd. (Mar. 2000).

Terada, Y., et al., "Microfilament stabilization by jasplakinolide arrests oocyte maturation, cortical granule exocytosis, sperm incorporation, cone resorption, and cell-cycle progression, but not DNA replication, during fertilization in mice," *Mol. Reprod. Dev.* 56:89-98, Wiley-Liss, Inc. (May 2000).

Tovich, P.R., et al., "Isolation and perinuclear immunolocalization of somatic histones H2B and H3 in bull sperm heads," *J. Androl.* (Suppl.): Abstract p. 19, (May/Jun. 2001).

Van Steirteghem, A.C., et al., "High fertilization and implantation rates after intracytoplasmic sperm injection," *Hum. Reprod.* 8:1061-1066, Oxford University Press (1993).

Von Bulow, M., et al., "Molecular nature of calicin, a major basic protein of the mammalian sperm head cytoskeleton," *Exp. Cell Res.* 219:407-413, Academic Press, Inc. (1995).

Von Bulow, M., et al., "Cpβ3, a novel isoform of an actin-binding protein, is a component of the cytoskeletal calyx of the mammalian sperm head," *Exp. Cell. Res.* 233:216-224, Academic Press, Inc. (1997).

Wilding, M., et al., "A soluble extract from human spermatozoa activates ascidian oocytes," *Dev. Growth Differ.* 39:9-36, Japanese Society of Developmental Biologists (1997).

Witton, C.J., et al., "Injection of a boar sperm factor causes calcium oscillations in oocytes of the marsupial opposum *Nonodelphis domestica,*" *Zygote* 7:271-277, Cambridge University Press (Nov. 1999).

Wolf, E., et al., "Nuclear transfer in mammals: recent developments and future perspectives," *J. Biotechnol.* 65:99-110, Elsevier Science (1998).

Wolf, D.P., et al., "Nuclear transfer in the rhesus monkey: practical and basic implications," *Biol. Reprod.* 60:199-204, Society for the Study of Reproduction (Feb. 1999).

Wolny, Y.M., et al., "Human glucosamine-6-phosphate isomerase, a homologue of hamster oscillin, does not appear to be involved in $Ca^{2+}$ release in mammalian oocytes," *Mol. Reprod. Dev.* 52:277-287, Wiley-Liss, Inc. (Mar. 1999).

Wolosker, H., et al., "Molecularly cloned mammalian glucosamine-6-phosphate deaminase localizes to the transporting epithelium and lacks oscillin activity," *FASEB J.* 12:91-99, Federation of American Societies for Experimental Biology (1998).

Wu, H., et al., "Partial characterization of the calcium-releasing activity of porcine sperm cytosolic extracts," *Dev. Biol.* 203:369-381, Plenum Press (1998).

Yagi, R., et al., "A WW domain-containing yes-associated protein (YAP) is a novel transcriptional co-activator," *EMBO J.* 18:2551-2562, Oxford University Press (May 1999).

Yang, X., et al., "Nuclear transfer in cattle: effect of nuclear donor cells, cytoplast age, co-culture, and embryo transfer," *Mol. Reprod. Dev.* 35:29-36, Wiley-Liss, Inc. (1993).

Yazawa, H., et al., "Comparison of oocyte activation and $Ca^{2+}$ oscillation-inducing abilities of round/elongated spermatids of mouse, hamster, rat, rabbit and human assessed by mouse oocyte activation assay," *Hum. Reprod.* 15:2582-2590, Oxford University Press (Dec. 2000).

Yazawa, H., et al., "Oocyte activation and $Ca^{2+}$ oscillation-inducing abilities of mouse round/elongated spermatids and the developmental capacities of embroys from spermatid injection," *Hum. Reprod.* 16:1221-1228, Oxford University Press (Feb. 2001).

Wu, A.T.H., et al., "PAWP, A Sperm Specific WW-Domain Binding Protein, Promotes Meiotic Resumption and Pronuclear . . . ," J. Biol. Chem. 282:12164-12175 (2007).

FIG 2A (SEQ ID NO:4)

1 CGGCACGAGGGGCGGCAGGAGGGGGCCTG*GGCAGG*

```
36  ATG GCA GTG AAC CAG AGC CAC ACC GAG AGC CGT CGT GGG GCC CTC ATC CCC TCT GGC GAA
 1   M   A   V   N   Q   S   H   T   E   S   R   R   G   A   L   I   P   S   G   E

96  AGT GTC TTG AAG CAG TGT GAG GAT GTG GAC CTC TGC TTC CTA CAG AAA CCA GTG AAA TCC
21   S   V   L   K   Q   C   E   D   V   D   L   C   F   L   Q   K   P   V   E   S

156 TAT CTC TTT AAT GGC ACA AAG AAA GGA ACG TTG TTT CTC ACT TCA TAC CGG GTG GTC TTC
41   Y   L   F   N   G   T   K   K   G   T   L   F   L   0T  S   Y   R   V   V   F

216 GTG ACT TCA CAC TTA GTC AAT GAC CCC ATG CTT TCT TTT ATG ATG CCG TTT GGC CTG ATG
61   V   T   S   H   L   V   N   D   P   M   L   S   F   M   M   P   F   G   L   M

276 AGT GAC TGC ACC ATT GAA CAA CCA ATT TTT GCC CCC AAC TAC ATT AAA GGA ACC ATT CAG
81   S   D   C   T   I   E   Q   P   I   F   A   P   N   Y   I   K   G   T   I   Q

336 GCA GCT CCA GGT GGT GGC TGG GAA GGA CAA GCT GTT TTT AAG TTA TCC TTC AGG AAA GGA
101  A   A   P   G   G   G   W   E   G   Q   A   V   F   K   L   S   F   R   K   G

396 GGT GCC ATC GAA TTT GCC CAA CTG ATG GTA AAA GCT GCC TCT GCT GCT GCC AGA GGA ATT
121  G   A   I   E   F   A   Q   L   M   V   K   A   A   S   A   A   A   R   G   I

456 CCA CTT GGA AGT GTA AAT TAC TGG TTC GAC ACT TCA GGA CTG TAC ATA ATT ACT GTC CCA
141  P   L   G   S   V   N   Y   W   F   D   T   S   G   L   Y   I   I   T   V   P
```

FIG 2B

```
516 GGG GCT GCA GTG TGC TCC TCA CAG ACA CCT TGT CCA GCA TAT CCA ATT GTG ATC TAT GGA
161  G   A   A   V   C   S   S   Q   T   P   C   P   A   Y   P   I   V   I  (Y   G

576 CCC CCA CCA CCA GGA TAT ACA GTC CAA CCA GGG GAA TAT GGA ACT CCA CCA GAA GGA TAT
181  P   P   P   P   G   Y)  T   V   Q   P   G   E  (Y   G   T   P   P   E   G) (Y
         ▲   ▲   ▲   ▲

636 GGA GCC CAA CCA GGG GGA TAT GGA GCC CCA CCT ATG GGA TAT GGA GCC CCG CCT GTG GGA
201  G   A   Q   P   G   G) (Y   G   A   P   P   M   G) (Y   G   A   P   P   V   G)

696 TAT GGA GTC CCA CCT GGG GGA TAT GGA GTC CCA CCT GGG GGA TAT GGA GTC CCA CCT GGG
221 (Y   G   V   P   P   G   G) (Y   G   V   P   P   G   G) (Y   G   V   P   P   G

756 GGA TAT GGA GCC CCA CCT GGG GGA TAT GGA GTC CCA CCT GGG GGA TAT GGT GCC CCA CCT
241  G] (Y   G   A   P   P   G   G) (Y   G   V   P   P   G   G) (Y   G   A   P   P

816 GGG GGA TAT GGA GCC CCA CCT GCA GGA TAT GGA GCC CCA CCA GCT GGA AAT GAA GCC CTA
261  G   G] (Y   G   A   P   P   A   G) (Y   G   A   P   P   A   G) N   E   A   L

876 CCC CCT GCA TAT GAA GCT CCA TCT GCT GGA AAT ACA GCT GCC TCT CAC AGA TCT ATG ACA
281  P   P   A   Y   E   A   P   S   A   G   N   T   A   A   S   H   R   S   M   T
         ▲   ▲   ▲   ▲

936 GCT CAG CAG GAG ACT TCT CTT CCC ACT ACC TCA TCT TCT TAG
301  A   Q   Q   E   T   S   L   P   T   T   S   S   S   ⊗
```

*GTCCATTTACCACCTTCTCAGAGT*⁴²TAAACCTTGAAGACTCACCAAGCAAAGGGCACCCTAAAACTGAAGTCACAGTAAGAAGG
AAGACCCAGGTGCCAGTGGTAGGAGGTGTTCGTGTGCACGCAGTGGTCTGATCTTCTCCACACACCTGTGAGGTCCTGTGCC
TCAAAACAGATGAAGGTGAGAAGACGACTCCTGTTCTCAAGGAAGGAAGATGCTTGAAAACAGACTGCAAGCCAACTAGAGAG
AGAGAGATGTGAAGTGGCACATAAAACAGCTTGGGGATGGAGACTGACTCTCTTTAGAAAACAGGCCTTCTCCCTGCCTCTGA
CCTGAGCAGAAAAGAGAAATCGCTGGAACCAAAGAGCTAGGGTCACCCTGCTTAGACGCCCTCGATTAAAGCCTGCTTGCTGT
TGCATAAAAAAAAAAAAAAAAA(1413)

FIG 3A

```
            10         20         30         40         50         60
PT32   MAVNQSHTESRRGALIPSGESVLKQCEDVDLCFLQKPVESYLFNGTKKGTLFLTSYRVVF
       ::.:..:.:. :.... . ::.:.. ..:.: :.          :.::::::::..:: :::.:
WBP2   MALNKNHSEGG-GVIVNNTESILMSYDHVELTFNDMKNVPEAFKGTKKGTVYLTPYRVIF
            10         20         30         40         50

70         80         90        100        110        120
PT32   VTSHLVNDPMLSFMMPFGLMSDCTIEQPIFAPNYIKGTIQAAPGGGWEGQAVFKLSFRKG
       ...      .: : :::::: ::..:: :.::.:. :.::: ...: ::::::::.: .::..: :
WBP2   LSKG--KDAMQSFMMPFYLMKDCEIKQPVFGANFIKGIVKAEAGGGWEGSASYKLTFTAG
          60         70         80         90        100        110

130        140        150        160        170
PT32   GAIEFAQLMVKAASAAARG-IPLGSVNYWFDTSGLYIITVPGAAVCSSQTPC ----313   (SEQ ID NO:19)
       :::::::..: :....: :.:: .: :. .: . :: :.,  :    :      ::
WBP2   GAIEFGQRMLQVASQASRGEVPNGAYGYPYMPSGAYVFPPP---VANGMYPC ----261   (SEQ ID NO:17)
           120        130        140        150        160
```

FIG 3B

```
         10        20        30        40        50        60
PT32 MAVNQSHTESRRGALIPSGESVLKQCEDVDLCFLQKPVESYLFNGTKKGTLFLTSYRVVF
     ::::.::  .:: : ::  :::.::.:  .::: : :.:   : ::..:::..::::::::.:
WBPM MAVNQNHTVDRRWAAIPHGESLLKKCSEVDLSFPQSPPGSNLFSGTKRGALFLTSYRVIF
         10        20        30        40        50        60

70        80        90       100       110       120
PT32 VTSHLVNDPMLSFNMPFGLMSDCTIEQPIFAPNYIKGTIQAAPGGGWEGQAVFKLSFRKG
     :::.   :::::.::  :::  ::...::.::::::.  :::::::::::  :::::.:.::  ::::
WBPM VTSRADNDPMFSFTMPFHLMNNCTVEQPIFGANYIKGTIQAAPDGGWEGSATFKIVFRKG
         70        80        90       100       110       120

130       140       150       160       170       180
PT32 GAIEFAQLMVKAASAAARGIPLGSVNYWFDTSGLYIITVPGAAVCSSQTPCPAYPIVIYG
     :::.:::::.::::::::::..:::   ....:.  :.:.::  :    . .:  :: .. ::
WBPM GAIDFAQLMAKAASAAAQGVPLRVASFWMGPLGIYVIT--GDR--NMYAP-QAYQVA-YG
        130       140       150       160           170

190       200       210       220
PT32 PPPPGYTVQPGEYGTPPEGYGAQPGGYGAPPMGYGAPPVGYGV-PPG------------
     :: :: ...:  :::.:  ::::  :.:::::::.:: ::   :: : :::
WBPM APPAGYGASPVGYGVPSAGYGAPPAGYGAPPVGYVAPSPGYDVLPPGYGAVRYGSPPPLY
        180       190       200       210       220       230

230       240       250                260
PT32 -----GYGVPPGGYGVPPGGYGAPPGGYGVP--------------PGGYGAPPGGYGAPP
     :::::: :::  ::  ::..:: ::  .:              : : :..::  : :::
WBPM VATPMGYGVPPPGYGPPPVRYGSPPPGYEAPTMEYGAQPPRYGTTPMGSGSPPPRYEAPP
        240       250       260       270       280       290

270       280       290       300       310
PT32 AGYGAPPAGNEALPP-------AYEAPSAGNTAASHRSMTAQQ---ETSLPTTSSS----
     :::.::.: :...::     : :::  ::. :.  :....:.   ...::.:::::
WBPM MGYGTPPSGRESIPPGSRATSVAQEAPPAGSEAGHPMSVAVQNPEFQASFPSTSSSQVHS
        300       310       320       330       340       350

PT32 ----- (SEQ ID NO:5)
WBPM PRSKM (SEQ ID NO:18)
```

FIG 4A

```
              80        90       100       110       120       130
PT32    MPFGLMSDCTIEQPIFAPNYIKGTIQAAPGGGWEGQAVFKLSFRKGGAIEFAQLMVKAAS
        ::  ::..  :.::::.::  :.::::::::  :::::::.::: :::.:  :::::::::::
WBPH    MPFDLMTNLTVEQPVFAANFIKGTIQAAPYGGWEGQATFKLVFRNGDAIEFAQLMVKAAS
              10        20        30        40        50        60

140       150       160       170       180       190
PT32    AAARGIPLGSVNYWFDTSGLYIITVPGAAVCSSQTPCPAYPIVIYGPPPPGYTVQPGEYG
        :                                       ...:: :: :: . :  ::
WBPH    A---------------------------------------VIVYGAPPAGYGAPPPGYG
                                                        70        80

200       210       220       230       240       250
PT32    TPPEGYGAQPGGYGAPPMGYGAPPVGYGVPPGGYGVPPGGYGVPPGGYGAPPGGYGVPPG
        .::  ::::::  :   .:::.:  : :: :::.::  .:::.:..:  :::::: :::..::
WBPH    APPAGYGAQPVGNEGPPVGYRASPVRYGAPPLGYGAPPAGYGAPPLGYGAPPLGYGTPPL
              90        100       110       120       130       140

260       270       280       290       300       310
PT32    GYGAPPGGYGAPPAGYGAPPAGNEALPPAYEAPSAGNTAASHRSMTAQQETSLPTTSSS
        ::::::  :::::::::  .::: .:  : .  :  . .:::  .. ..::.:::..:::
WBPH    GYGAPPLGYGAPPAGNEGPPAGYRASPAGSGARPQESTAA----QAPENEASLPSASSS
              150       160       170       180       190

PT32    ----------------------------  (SEQ ID NO:9)

WBPH    QDKEDDSGQPFLRKSAFQCLLECDDYLIVR  (SEQ ID NO:10)
              200       210       220
```

FIG 4B

```
(SEQ ID NO:11) 1  ATGCCATTTGATCTGATGACGAACCTCACTGTTGAACAACCAGTATTTGCTGCAAACTTC
(SEQ ID NO:12) 1   M  P  F  D  L  M  T  N  L  T  V  E  Q  P  V  F  A  A  N  F
              61  ATTAAGGGAACTATTCAGGCAGCTCCATATGGTGGCTGGGAAGGACAAGCTACTTTTAAA
              21   I  K  G  T  I  Q  A  A  P  Y  G  G  W  E  G  Q  A  T  F  K
             121  TTAGTCTTCAGAAATGGAGATGCCATTGAATTTGCCCAGTTGATGGTGAAAGCTGCCTCT
              41   L  V  F  R  N  G  D  A  I  E  F  A  Q  L  M  V  K  A  A  S
             181  GCTGTTGCCCGAGGATTTCCACTTAGAACCTTAAATGACTGGTTCAGCTCTATGGGAATT
              61   A  V  A  R  G  F  P  L  R  T  L  N  D  W  F  S  S  M  G  I
             241  TATGTAATTACTGGGGAAGGGAATATGTGCACTCCACAGATGCCTTGTTCAGTTATTGTC
              81   Y  V  I  T  G  E  G  N  M  C  T  P  Q  M  P  C  S  V  I  V
             301  TATGGGGCCCCACCTGCAGGATATGGAGCCCCACCTCCCGGATACGGAGCCCCACCTGCA
             101  [Y  G  A  P  P  A  G][Y  G  A  P  P  P  G][Y  G  A  P  P  A
             361  GGATATGGAGCCCAACCCGTAGGAAATGAAGGCCCGCCTGTGGGATACAGAGCCTCACCT
             121   G] Y  G  A  Q  P  V  G  N  E  G  P  P  V  G  Y  R  A  S  P
             421  GTGCGATATGGAGCCCCACCTCTTGGATACGGAGCCCCACCTGCAGGATATGGAGCCCCA
             141   V  R [Y  G  A  P  P  L  G][Y  G  A  P  P  A  G][Y  G  A  P
             481  CCTCTAGGATATGGAGCCCCACCTCTTGGATATGGAACCCCACCTCTCGGATATGGAGCC
             161   P  L  G][Y  G  A  P  P  L  G][Y  G  T  P  P  L  G][Y  G  A
             541  CCACCTCTCGGATATGGAGCCCCACCTGCAGGAAATGAAGGCCCGCCTGCGGGATACAGA
             181   P  P  L  G][Y  G  A  P  P  A  G] N  E  G  P  P  A  G  Y  R
             601  GCCTCACCTGCTGGATCAGGAGCCAGGCCTCAGGAATCTACAGCAGCCCAGGCTCCTGAA
             201   A  S  P  A  G  S  G  A  R  P  Q  E  S  T  A  A  Q  A  P  E
             661  AACGAGGCTTCTCTTCCCTCTGCCTCCTCTTCTCAGGTCCATTCTTAACCTTCTAAGATG
             221   N  E  A  S  L  P  S  A  S  S  S  Q  V  H  S ***
                  TAAACCTTGAAGACTCACCAAGCAAAGAGGTACCCTAAAATTGAAGTCAGGATAAGGAGG
                  ACGACTCAGCTTAGAGTCATTGATTGATCTGCATTGTGAAAATTAGGAAACCAGATGCTC
                  CCATGTTCTCAAGGACGACCTTTCTTAAGGAAGTCAGTACGTGGGCAACAGTGATGAGAG
                  GAAGAGAGGAGAGACTCAACCAACTAGAGCAGGGATAAGGTTTCCCTTGTTCAGCTTTTC
                  AGTGTCTGCTGGAATGTGATGATTACCTCATTGTCAGGTAG 42
```

FIG 6
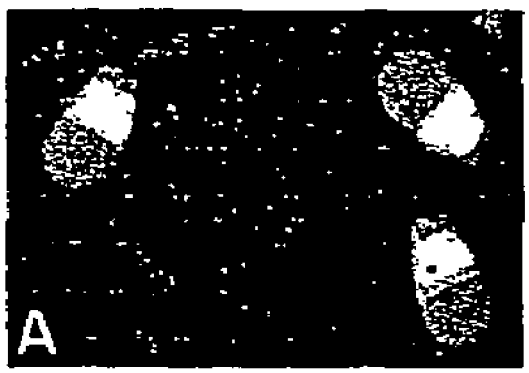

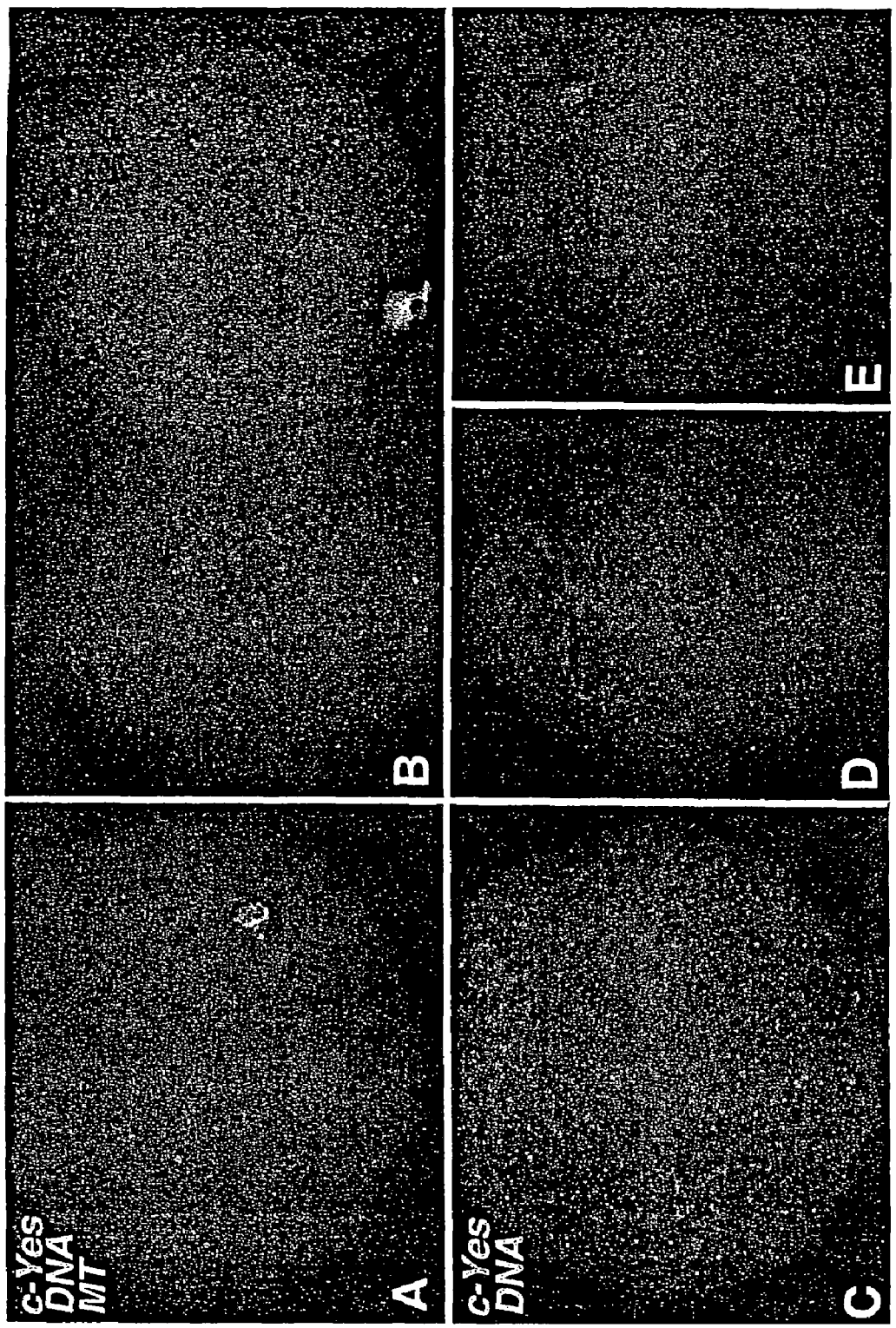
FIG 8 - I

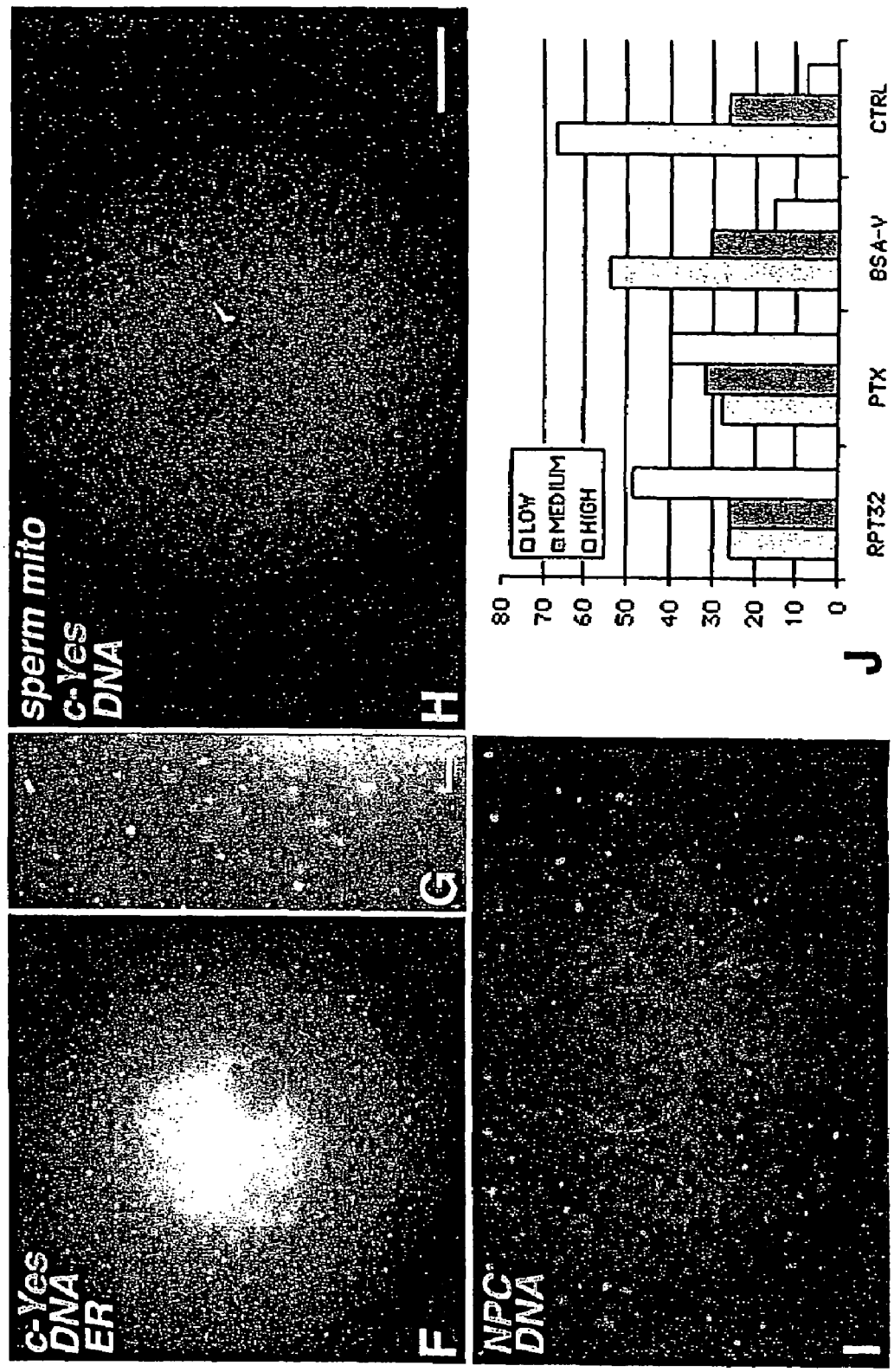
FIG 8 - II

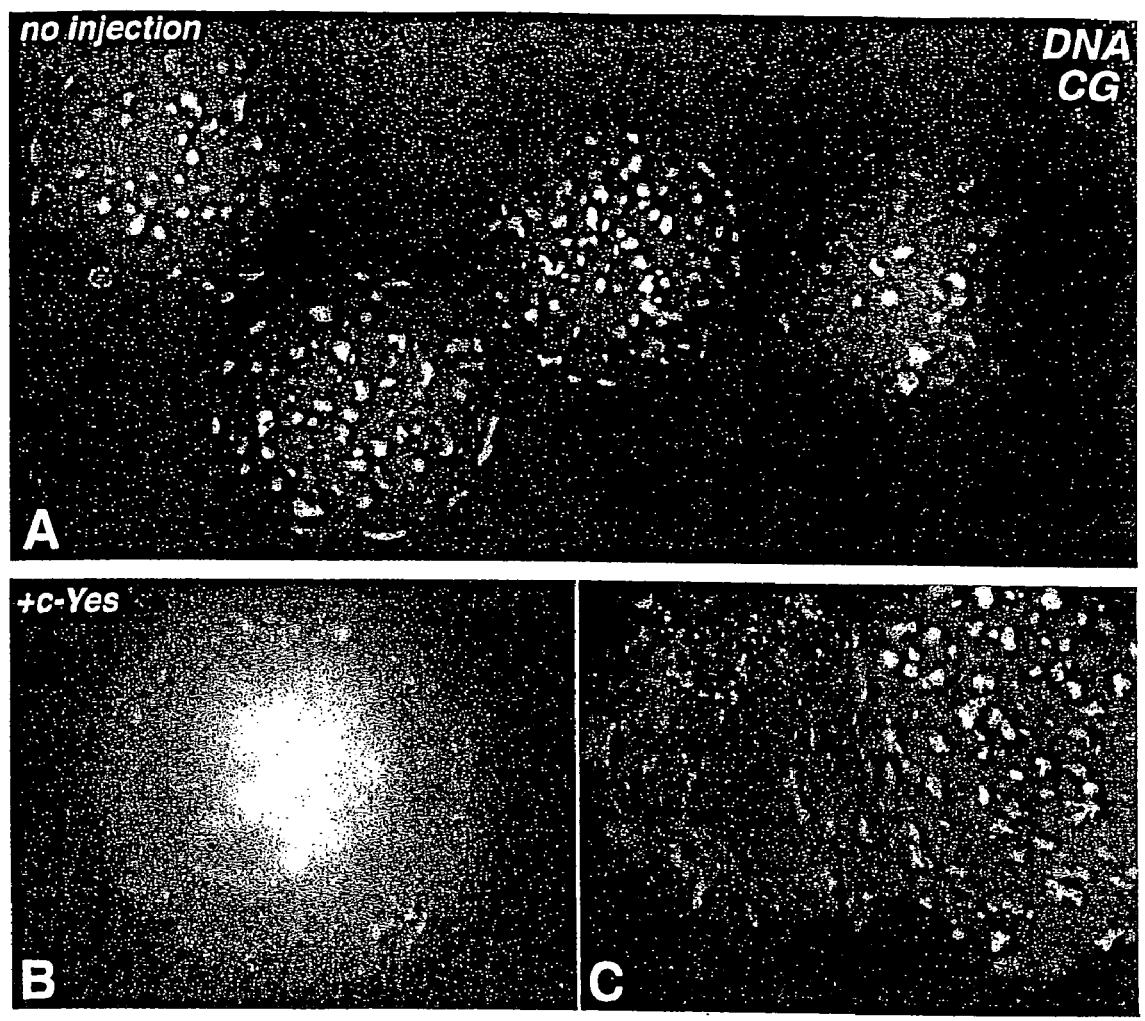
FIG 9 - I

FIG 9 - II
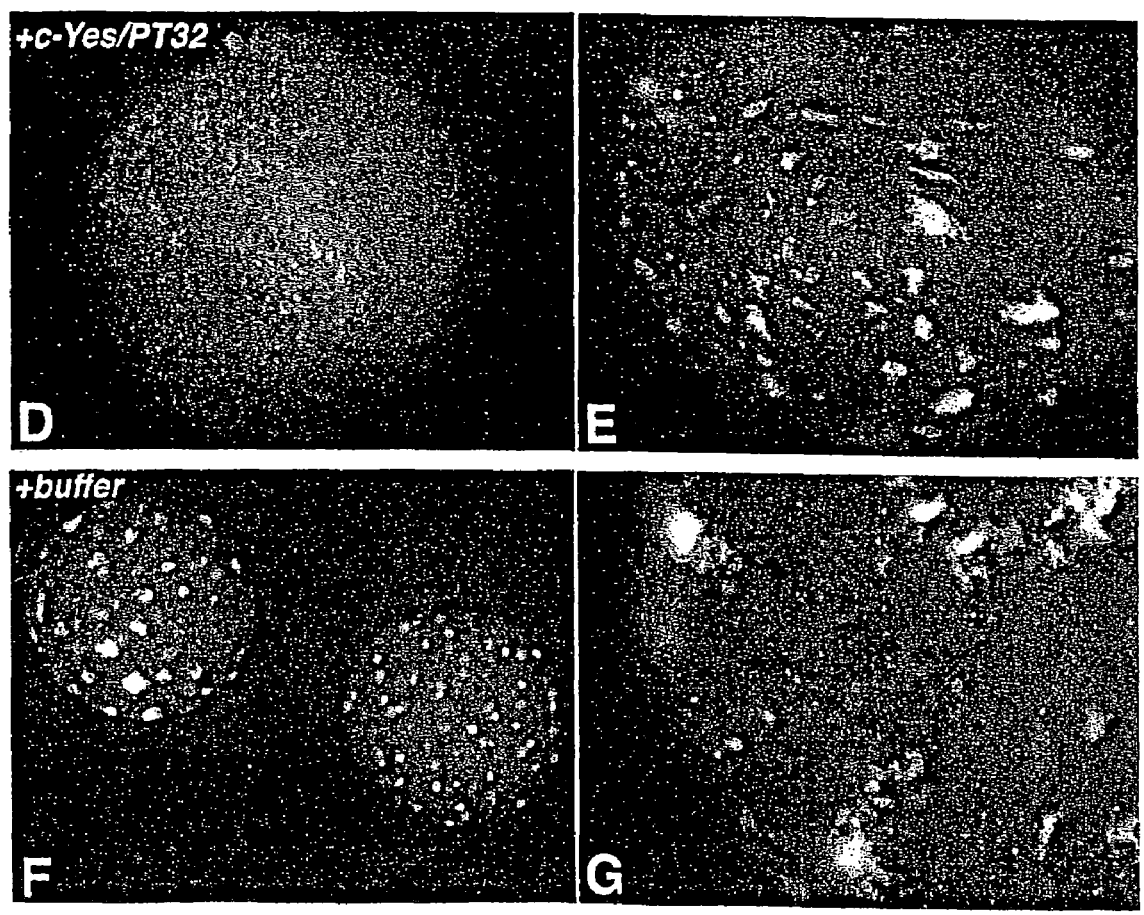

FIG 10

```
  1 mgcikskedk gpamkyrtdn tpepisshvs hygsdssqat qspaikgsav nfnshsmtpf
 61 ggpsgmtpfg gasssfsavp spypstltgg vtvfvalydy earttddlsf kkgerfqiin
121 ntegdwwear siatgktgyi psnyvapads iqaeewyfgk mgrkdaerll lnpgnqrglf
181 lvresettkg ayslsirdwd evrgdnvkhy kirkldnggy yittraqfes lqklvkhyre
241 hadglchklt tvcptvkpqt qglakdawei preslrlevk lgqgcfgevw mgtwngttkv
301 aiktlkpgtm mpeaflqeaq imkklrhdkl vplyavvsee piyivtefmt kgslldflke
361 gegkflklpq lvdmaaqiad gmayiermny ihrdlraanl lvgdnlvcki adfglarlie
421 dneytarqga kfpikwtape aalygrftik sdvwsfgill telvtkgrvp ypgmvnrevl
481 eqvergyrmp cpqgcpeslh elmklcwkkd pderptfeyl qsfledyfta tepqyqpgdn
541 l
```

(SEQ ID NO:20)

PT32 SPERM PROTEIN, SPERM C-YES, OOCYTE CYTOPLASMIC C-YES, AND USES THEREOF

CROSS-REFERENCE TO RELATED APPLICATIONS

This application is a divisional of application Ser. No. 09/864,291, filed May 25, 2001 now U.S. Pat. No. 6,995,252 which claims the benefit of Provisional Application 60/206,979 filed May 25, 2000, both of which are incorporated herein by reference.

STATEMENT REGARDING FEDERALLY-SPONSORED RESEARCH AND DEVELOPMENT

Part of the work performed during development of this invention utilized U.S. Government funds, awarded by the National Institutes of Health (Grant No. R-21, RR14293-01) and by the United States Department of Agriculture (New Investigator Award #99-35203-7785). The U.S. Government has certain rights in this invention

BACKGROUND OF THE INVENTION

1. Field of the Invention

The invention relates to proteins of the mammalian sperm and oocyte, and uses thereof, e.g., in enhancing fertility and in contraception.

2. Background Art

Oocyte activation in mammals encompasses the resumption of second meiosis and the activation of anti-polyspermy defense, which are accompanied by calcium oscillations periodically crossing oocyte cytoplasm (reviewed by Schultz, R. M., and Kopf, G. S., "Molecular basis of mammalian egg activation,"in Current Topics in Developmental Biology, Pedersen, R. A., and Schatten, G. P., (eds), Vol. 30, Academic Press Inc., San Diego, (1995) pp. 21-62). In bovine and other mammals, the fertilization-induced oocyte activation is also accompanied by the assembly of nuclear pore complexes (NPC) into the cytoplasmic annulate lamellae (AL), and by the insertion of NPCs into a de novo-formed nuclear envelope (NE) of the female and male pronuclei (Sutovsky et al., J. Cell Sci. 111:2841-2854 (1998)). Three hypotheses were offered to explain the sperm-induced oocyte activation in mammals: The conduit, or calcium bomb hypothesis (Jaffe, L. F., Ann. N.Y. Acad. Sci. 339:86-101 (1980)) implicates the direct, sperm-generated "injection" of $Ca^{2+}$ ions into oocyte cytoplasm at fertilization. The receptor hypothesis (e.g. Jones, K. T., and Whittingham, D. G., Dev. Biol. 178:229-237 (1996); Swann, K., Development 110:1295-1302 (1990)) maintains that the specific receptors on the sperm and oocyte plasma membranes activate a signaling cascade leading to the release of $Ca^{2+}$ from internal stores in oocyte ER. Finally, the oscillogen hypothesis favors a soluble oscillogenic factor, presumably a polypeptide, which is released from the sperm head into the oocyte cytoplasm at the time of gamete fusion (Kimura, Y., et al., Biol. Reprod. 58:1407-1415 (1998); Parrington, J., et al., Nature 379:364-368 (1996); Perry, A. C. F., et al., Biol. Reprod 60:747-755 (1999)). Although there is a substantial amount of data in favor of each of the above hypotheses, and each of them may be relevant to certain animal taxa, recent studies seem to support the validity of the oscillogen hypothesis in mammals. The actual mechanism by which the spermatozoon introduces the oscillogenic molecules into oocyte cytoplasm is not known.

Perinuclear theca (PT) is a cytoskeletal coat of the mammalian sperm nucleus that is inserted between the nuclear envelope and the sperm plasma membrane (Bellvé, A. R., et al., Biol. Reprod. 47:451-465 (1992); Courtens, J. L., et al., J. Ultrastruct. Res. 57:54-64 (1976); Lalli, M., and Clermont, Y., Am. J. Anat. 160:419-434 (1981); Oko, R., and Clermont, Y., Biol. Reprod. 39:673-687 (1988)). During spermiogenesis, the PT attaches the acrosomal vesicle to the sperm nucleus and may be involved in shaping it (Oko, R., and Maravei, D., Biol. Reprod. 50:1000-1014 (1994); Oko, R., and Maravei, D., Microsc. Res. Tech. 32:520-532 (1995); Oko, R., and Clermont, Y., "Spermiogenesis," in Encyclopedia of Reproduction, Knobil, E. and Neil, J. D., (eds.), Vol. IV, Academic Press Inc., San Diego (1998) pp. 602-609). At fertilization, the PT is removed from the sperm nucleus with the aid of oocyte's cortical microvilli (Sutovsky et al., Dev. Biol. 188:75-84 (1997)). Otherwise, an intact PT would constitute an unsurpassable hurdle preventing the access of the zygotic cytoplasm to the sperm nucleus, which at that time undergoes the remodeling into a male pronucleus. Recent studies of infertile men suffering from globozoospermy (Battaglia, D. E., et al., Fertil. Steril. 68:118-122 (1997); Edirisinghe, W. R., et al., Hum. Reprod. 13:3094-3098 (1998); Rybouchkin, A., et al., Hum. Reprod. 11:2170-2175 (1996)), a rare spermatogenic disorder in which the absence of PT causes the round shape of the sperm nucleus (Escalier, D., Int. J. Dev. Biol. 34:287-297 (1990)), demonstrated that such spermatozoa fail to induce oocyte activation after intracytoplasmic sperm injection (ICSI). Human and non-human primate oocytes are activated by ICSI with normal spermatozoa (Hewitson, L. C., et al., Biol. Reprod. 55:271-280 (1996); Palermo, G., et al., Lancet 340:17-18 (1992); Sutovsky, P., et al., Human Reprod. 14:2301-2312 (1996); Van Steirteghern, A., et al., Hum. Reprod. 8:1061-1066 (1993)) and the intracytoplasmic injection of crude (Swann, K., Development 110:1295-1302 (1990)) or partially purified (Kimura, Y., et al., Biol. Reprod 58:1407-1415 (1998); Perry, A. C. F., et al., Biol. Reprod. 60:747-755 (1999)) sperm extracts or demembranated sperm heads (Kimura, Y., et al., Biol. Reprod. 58:1407-1415 (1998)) activates rodent oocytes.

BRIEF SUMMARY OF THE INVENTION

The present invention is derived, at least in part, from the observation that, even though the PT is removed from the sperm nucleus at the egg surface, it is incorporated completely into oocyte cytoplasm, where it dissolves concomitantly with the progress of pronuclear development. This observation conforms with the increased oocyte activation rates that are obtained after intracytoplasmic injections of pure PT extracts into bovine oocytes, as compared with sham-injected oocytes. The activated oocytes injected with PT-extracts, but not the control, sham-injected, oocytes, displayed the patterns of the nuclear pore complex (NPC) and annulate lamellae (AL) assembly typical of natural fertilization. Furthermore, secondary spermatozoa prevented from entering the oocyte cytoplasm by polyspermy block still show PT release from any part of the sperm head that has fused with the oolemma. Ultrastructural studies showed the dissolution of PT in the oocyte cytoplasm during monospermic fertilization and polyspermy. Taken together, these data support the view that sperm PT harbors the oocyte activating-factor(s) and provides a mechanism for the release of oscillogen(s) from the sperm head into oocyte cytoplasm at fertilization. As discussed below, the sperm perinuclear theca protein PT32 is one such oscillogen, which directly or indirectly interacts with the protein tyrosine kinase c-Yes during spermatogenesis and fertilization.

Accordingly, the invention features an isolated perinuclear theca polypeptide that includes (a) at least one of (i) the sequence PPPGY (SEQ ID NO:1) and (ii) the sequence LPPAY (SEQ ID NO:2) and (b) at least three domains (e.g., 4, 5, 6, 7, 8, 9, 10, 11, or 12 or more domains), each domain comprising the sequence YGXPPXG (SEQ ID NO:3), wherein Y represents a Tyrosine residue, G represents a Glycine residue, L represents a Leucine residue, A represents an Alanine residue, X represents any amino acid residue, and P represents a Proline residue. Optionally, some or all of the YGXPPXG (SEQ ID NO:3) domains may include additional amino acid residues (e.g., 1, 2, 3, 4, or 5 additional residues) flanking SEQ ID NO:3. In various embodiments, the polypeptide has a molecular weight of about 32 kDa (e.g., about 28-33 kDa); and/or the polypeptide induces oocyte activation; and/or the polypeptide binds to: (i) tyrosine kinase c-Yes, and/or (ii) an adapter protein that binds to tyrosine kinase c-Yes; and/or (iii) phospholipase C. Preferably, the polypeptide is a component of a phospholipase C signal transduction pathway. The c-Yes adapter protein(s) can be present in the sperm and/or oocyte.

Included within the invention are fragments of the polypeptide that are (i) antigenic, (ii) biologically active, and/or (iii) able to bind to the protein tyrosine kinase c-Yes and/or to c-Yes adapter proteins. An "antigenic" fragment is a portion of the polypeptide which is capable of eliciting an immune response in a host and capable of interacting with antibodies or immune cells in vitro or in vivo. A "biologically active" fragment is a portion of the polypeptide which is capable of inducing oocyte activation alone or by interacting with other polypeptides, such as tyrosine kinase c-Yes or tyrosine kinase c-Yes adapter proteins. Typically, such a fragment contains at least 3 (typically, at least 10 or all) of the YGXPPXG domains (SEQ ID NO:3), along with a PPPGY domain (SEQ ID NO:1) or LPPAY domain (SEQ ID NO:2).

An exemplary polypeptide of the invention is a bovine PT32 having the sequence of SEQ ID NO:5, illustrated in FIG. 2, or conservative variants thereof. Such a polypeptide can be encoded by the coding sequence contained within GenBank accession no. AF322215. Another exemplary polypeptide of the invention is human PT32, which has the sequence of SEQ ID NO:12, as illustrated in FIG. 4B, or conservative variants thereof.

More generally, the invention features an isolated perinuclear theca polypeptide that includes (a) the sequence PPXY (SEQ ID NO:8) and (b) at least three domains (e.g., 4, 5, 6, 7, 8, 9, 10, 11, 12, or more domains), each domain comprising the sequence XGXPPXG (SEQ ID NO:3), wherein Y represent a Tyrosine residue, G represents a Glycine residue, X represents any amino acid, and P represents a Proline residue. Optionally, some or all of the YGXPPXG (SEQ ID NO:3) domains may include additional amino acid residues (e.g., 1, 2, 3, 4, or 5 additional residues) flanking SEQ ID NO:3. The sequence PPXY (SEQ ID NO:8) is also referred to herein as the PY motif. Examples of sequences that include a PY motif are the sequences PPPGY (SEQ ID NO:1) and LPPAY (SEQ ID NO:2). The sequence PPXY (SEQ ID NO:8) is present in both the human and murine PT32 proteins. In various embodiments, the polypeptide has a molecular weight of about 32 kDa (e.g., about 28-33 kDa), the polypeptide binds to tyrosine kinase c-Yes, and/or the polypeptide induces oocyte activation. Such polypeptides can be used in the methods described herein as an alternative to, or in combination with, PT32. For example, such polypeptides can be used in methods for enhancing fertility, treating or diagnosing diminished fertility and/or abnormal spermiogenesis, providing contraception, and in identifying fertility-enhancing agents, as described herein for PT32.

In a related aspect, the invention features a WW domain binding protein that comprises amino acid residues 61 to 97 of SEQ ID NO:12, or conservative variants thereof. For example, the invention includes human testicular WW domain binding protein, set forth as SEQ ID NO:12, and conservative variants thereof.

Peptidomimetics of the aforementioned polypeptides also are included within the invention. In Morgan et al. ("Approaches to the discovery of non-peptide ligands for peptide receptors and peptidases." Annual Reports in Medicinal Chemistry. Ed. F. J. Vinick. San Diego: Academic Press, 1989, pp. 243-252), peptide mimetics are defined as "structures which serve as appropriate substitutes for peptides in interactions with receptors and enzymes. The mimetic must possess not only affinity, but also efficacy and substrate function." As used herein, the terms "peptidomimetic" and "peptide mimetic" are interchangeable according to the above-excerpted definition. That is, a peptidomimetic exhibits function(s) of a peptide, without restriction of structure. Peptidomimetics of the present invention, i.e., analogues of biologically active fragments of PT32 or c-Yes, may include amino acid residues or other moieties which provide the functional characteristics described herein.

The invention also features isolated polynucleotides encoding the aforementioned polypeptides. As used herein, "polynucleotide" generally refers to any polyribonucleotide or polydeoxyribonucleotide, which may be unmodified RNA or DNA, including cDNA, genomic DNA, and synthetic DNA, or modified RNA or DNA. The DNA may be double-stranded or single-stranded, and if single stranded may be the coding strand or non-coding (anti-sense) strand. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms of the polynucleotides typically found in nature, as well as the chemical forms of DNA and RNA characteristic of viruses and cells. "Polynucleotide" also embraces relatively short polynucleotides, often referred to as oligonucleotides.

Fragments of the polynucleotides of the present invention may be used as hybridization probes for a cDNA library to isolate the full length cDNA and to isolate other cDNAs which have a high sequence similarity to the polynucleotides or similar function to the encoded polypeptides. Probes of this type preferably have at least 15 bases, and may contain, for example, 18, 20, 25, 30, or 50 or more bases. The probe may also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of cDNA, genomic DNA or mRNA to determine to which members of the library the probe hybridizes.

An exemplary polynucleotide of the invention includes the sequence of SEQ ID NO:4, illustrated in FIG. 2, or degenerate variants thereof. Such a polynucleotide sequence is included within the nucleic acid deposited as GenBank accession no. AF322215. Another exemplary polynucleotide of the invention includes the sequence of SEQ ID NO:11, illustrated in FIG. 4B, or degenerate variants thereof. In various embodiments, the invention also includes: (i) a gene that includes such a polynucleotide; (ii) a vector that includes such a polynucleotide or such a gene; and (iii) a host cell that contains such a vector. In addition, the invention includes a method of producing a polypeptide by maintaining the aforementioned host cell under conditions such that the polypeptide is expressed, then collecting the polypeptide. In further embodiments, the invention features: (i) a WW domain binding protein comprising amino acid residues 61 to 97 of SEQ ID NO:12, or conservative variants thereof; and (ii) an isolated polypeptide comprising amino acid residues 61 to 97 of SEQ ID NO:12.

In other embodiments, the invention includes: (i) an isolated polynucleotide comprising a sequence that is at least 75% identical to nucleotides 36 to 933 of SEQ ID NO: 4; (ii) an isolated polynucleotide comprising a sequence that is at least 75% identical to nucleotides 1 to 705 of SEQ ID NO:11; (iii) an isolated polypeptide comprising a sequence that is at least 75% identical to SEQ ID NO:5; and (iv) an isolated polypeptide comprising a sequence that is at least 75% identical to SEQ ID NO:12.

Also included within the invention is a method for inducing oocyte activation, the method comprising contacting an oocyte with (i) an isolated polypeptide comprising the sequence of murine testicular WBP like protein (WBPM; SEQ ID NO:18) or (ii) a biologically active fragment thereof, or conservative variants of (i) or (ii). Similarly, the invention includes a method for enhancing fertility in a mammal, the method comprising expressing in a germ cell of the mammal an isolated polypeptide comprising (i) the sequence of SEQ ID NO:18 or (ii) a biologically active fragment thereof, or conservative variants of (i) or (ii). This murine protein can be used in the various methods described herein for PT32. For example, the invention includes a method for identifying a modulator of oocyte activation, the method comprising contacting a test compound with an oocyte; treating the oocyte with the an isolated polypeptide comprising (i) the sequence of SEQ ID NO:18 or (ii) a biologically active fragment thereof, or conservative variants of (i) or (ii), under conditions sufficient to induce oocyte activation in the absence of the test compound; and detecting inhibition or enhancement of oocyte induction as an indication that the test compound is a modulator of oocyte activation.

The term "gene" means the segment of DNA involved in producing a polypeptide chain; it includes regions preceding and following the coding region (leader and trailer) as well as intervening sequences (introns) between individual coding segments (exons). It may further include regulatory elements, such as promoters, enhancers, operators, and repressors, which are useful in promoting, regulating, and/or repressing expression of the gene.

The present invention further relates to variants of the herein described polynucleotides which encode fragments, analogs and derivatives (including semi-synthetic variants) of the polypeptides of the invention. "Variant," as the term is used herein, is a polynucleotide or polypeptide that differs from a reference polynucleotide or polypeptide, respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be naturally occurring, such as an allelic variant, or it may be a variant that is not known to occur naturally. Non-naturally occurring variants of polynucleotides and polypeptides may be made by mutagenesis techniques or by direct synthesis.

Also included within the invention are antibodies that specifically bind to the polypeptides of the inventions. Such antibodies can be polyclonal or monoclonal. For example, antibodies that specifically bind to PT32 can be raised by immunizing mammals, e.g., rabbits, with fragments of PT32. For example, antibodies can be raised against a polypeptide having the amino acid sequence TSYRVVFVT-SHLVNDPMLSFMMPF (SEQ ID NO:6) or NEALPPA-YEAPSAGNT (SEQ ID NO:7). Such antibodies can be used in immunological assays, e.g., Western blotting, ELISAs, and in situ immunofluorescent studies.

The aforementioned such antibodies can be formulated with a pharmaceutically acceptable carrier to produce a pharmaceutical composition for use, for example, in immunocontraceptive methods. Other suitable pharmaceutical compositions may include a pharmaceutically acceptable foam and at least one of the following molecules: an antibody that specifically binds to PT32, an antibody that specifically binds to c-Yes, PT32 or a fragment thereof, c-Yes or a fragment thereof, an agonist or antagonist of PT32, and an agonist or antagonist of c-Yes. Such compositions can be used to modulate (enhance or inhibit) oocyte activation in fertility-enhancing or contraceptive methods.

Various methods also are included within the invention. For example, the invention features a method for inducing or enhancing oocyte activation, the method comprising contacting an oocyte of a mammal (e.g., a human or cow) with at least one of: (1) an isolated polypeptide, such as PT32, that includes (a) at least one of (i) the sequence PPPGY (SEQ ID NO:1) and (ii) the sequence LPPAY (SEQ ID NO:2) and (b) at least three domains (e.g., 4, 5, 6, 7, 8, 9, 10, 11, or 12 or more domains), each domain comprising the sequence YGXPPXG (SEQ ID NO:3), or a biologically active fragment thereof, or a peptidomimetic thereof, and/or (2) a c-Yes polypeptide or a biologically active fragment thereof; additionally, the oocyte is contacted with globozoospermic sperm or with round spermatids, which sperm or spermatids optionally lack PT32 and/or c-Yes. Oocyte activation can be induced in vitro or in vivo. In a related method, an oocyte is contacted with a composition consisting essentially of PT32 and/or c-Yes, or a biologically active fragment(s) thereof.

The invention also includes a method for enhancing fertility in a mammal by expressing a biologically active polypeptide of the invention in a germ cell of the mammal (e.g., human, bovine, pig, sheep, goat, monkey, or horse). More particularly, the invention includes a method for treating globozoospermy by expressing in spermatozoa an isolated polypeptide that includes (a) at least one of (i) the sequence PPPGY (SEQ ID NO:1) and (ii) the sequence LPPAY (SEQ ID NO:2) and (b) at least three domains (e.g., 4, 5, 6, 7, 8, 9, 10, 11, or 12 or more domains), each domain comprising the sequence YGXPPXG (SEQ ID NO:3). Preferably, the polypeptide is a biologically active polypeptide (e.g., biologically active PT32.

Similarly, the invention features a method for treating round spermatids by expressing in the round spermatids an isolated polypeptide that includes (a) at least one of (i) the sequence PPPGY (SEQ ID NO:1) and (ii) the sequence LPPAY (SEQ ID NO:2) and (b) at least three domains (e.g., 4, 5, 6, 7, 8, 9, 10, 11, or 12 or more domains), each domain comprising the sequence YGXPPXG (SEQ ID NO:3). Preferably, the polypeptide is a biologically active polypeptide (e.g., biologically active PT32).

In a related aspect, the invention features a method for enhancing fertility and/or activating an oocyte in a mammal by contacting an oocyte with (e.g., introducing into the oocyte) tyrosine kinase c-Yes, or a biologically active fragment thereof. A biologically active tyrosine kinase c-Yes polypeptide or fragment thereof is capable of phosphorylating a target protein.

Methods for identifying modulators (i.e., enhancers or inhibitors) of oocyte activation also are included within the invention. In an exemplary method, a test compound is contacted with an oocyte, and the oocyte is treated with a biologically active polypeptide of the invention under conditions sufficient to induce oocyte activation in the absence of the test compound. Modulation of oocyte induction then is detected as an indication that the test compound is an modulator of oocyte activation.

A related method for identifying a modulator of oocyte activation includes (A) contacting a test compound with (I) a polypeptide, such as PT32, that includes (a) at least one of (i) the sequence PPPGY (SEQ ID NO:1) and (ii) the sequence LPPAY (SEQ ID NO:2) and (b) at least three domains, each domain comprising the sequence YGXPPXG (SEQ ID NO:3), or a fragment thereof that binds to c-Yes or to an adapter protein that binds to c-Yes, and (II) tyrosine kinase c-Yes or a fragment thereof that binds to PT32 or to an adapter protein, under conditions sufficient to permit in the absence of the test compound binding of the polypeptide or fragment thereof to tyrosine kinase c-Yes or the fragment thereof, and (B) detecting modulation (i.e., enhancement or inhibition) of binding of the polypeptide or the fragment thereof to the tyrosine kinase c-Yes or the fragment thereof as an indication that the test compound is an modulator of oocyte activation.

The invention also provides methods for modulating (i.e, enhancing or inhibiting) fertilization. For example, the invention includes a method for inhibiting fertilization of a mammalian oocyte by inhibiting the interaction of PT32 with tyrosine kinase c-Yes in the oocyte. Such inhibition can include contacting the oocyte with at least one of: (a) an antibody that specifically binds to PT32 and (b) an antibody that specifically binds to tyrosine kinase c-Yes.

In an exemplary immunocontraceptive method, a polypeptide that includes (a) at least one of (i) the sequence PPPGY (SEQ ID NO:1) and (ii) the sequence LPPAY (SEQ ID NO:2) and (b) at least three domains, each domain comprising the sequence YGXPPXG (SEQ ID NO:3), or an antigenic fragment of such a polypeptide, is introduced into a mammal (typically a male), such that an immune response is elicited. For example, PT32 can be used in such a method. The polypeptide, or antigenic fragment thereof, elicits an immune response in the mammal, and the biological activity of PT32 endogenous to the mammal is inhibited, thereby inhibiting fertilization.

Optionally, the polypeptide or antigenic fragment thereof is produced as a fusion protein that includes the polypeptide (or antigenic fragment) covalently linked to a second polypeptide. The second polypeptide can be a conventional carrier protein, which preferably is foreign to the host (e.g., ovalbumin or keyhole limpet hemocyanin (KLH)) to facilitate the elicitation of an immune response. Such fusion polypeptides (or, alternatively, antigenic, non-fusion polypeptides of the invention) can be formulated with a conventional adjuvant to produce a vaccine for administration to a mammal (e.g., human or bovine) in a immunocontraceptive method. Alternatively, the second polypeptide of a fusion polypeptide can be a marker sequence that facilitates detection or purification of the polypeptide of the invention. For example, the marker sequence can be a hexahistidine tag, e.g., supplied by a pQE-9 vector, to provide for purification of a recombinant polypeptide from a prokaryotic (bacterial) host cell. Alternatively, the marker sequence can be a hemagglutinin (HA) tag (i.e., an epitope of an influenza hemagglutinin protein) to facilitate purification from a eukaryotic, e.g., mammalian, host cell (e.g., COS-7) cells. In another example, a green fluorescent protein (GFP) is fused to a polypeptide of the invention to facilitate protein detection using fluorescent methods. A variety of other art-known marker-polypeptides can be fused to the polypeptides of the invention to produce fusion proteins.

As an alternative to introducing a polypeptide vaccine into a mammal, a DNA vaccine can be used to elicit an immune response in the mammal. For example, a polynucleotide encoding a polypeptide (e.g., PT32) that includes (a) at least one of (i) the sequence PPPGY (SEQ ID NO:1) and (ii) the sequence LPPAY (SEQ ID NO:2) and (b) at least three domains, each domain comprising the sequence YGXPPXG (SEQ ID NO:3), can be administered to the mammal under conditions that permit expression of the polypeptide in the mammal, thereby eliciting an immune response against the polypeptide. Preferably, the polypeptide is not biologically active. Optionally, a DNA vaccine can include a polynucleotide encoding a carrier protein fused to the polypeptide.

The invention also includes several diagnostic methods. For example, the invention includes a method for diagnosing diminished fertility in a mammal by measuring in a germ cell (spermatozoa or oocyte) of the mammal the level of (A) tyrosine kinase c-Yes and/or (B) a polypeptide (e.g., PT32) that includes (a) at least one of (i) the sequence PPPGY (SEQ ID NO:1) and (ii) the sequence LPPAY (SEQ ID NO:2) and (b) at least three domains, each domain comprising the sequence YGXPPXG (SEQ ID NO:3). A diminution in the levels of c-Yes and/or the polypeptide in the germ cell (e.g., by 10%, 25%, 50% or even more) indicates that the mammal suffers from (or is at risk for) diminished fertility.

In a related aspect, the invention provides a method for diagnosing abnormal spermiogenesis in a mammal. The method includes comparing (1) the pattern of the distribution of a polypeptide that includes (a) at least one of (i) the sequence PPPGY (SEQ ID NO:1) and (ii) the sequence LPPAY (SEQ ID NO:2) and (b) at least three domains, each domain comprising the sequence YGXPPXG (SEQ ID NO:3) (e.g., PT32), throughout mature spermatozoa of the mammal with (2) the pattern of the distribution of the polypeptide throughout healthy, mature spermatozoa, wherein an abnormal distribution pattern is an indication that spermiogenesis in the mammal is abnormal. For example, the failure of PT32 to be localized (i) between the acrosome and the nucleus of the spermatozoa and/or (ii) on the post-acrosomal portion of the head of the spermatozoa is an indication that spermiogenesis is abnormal in the mammal.

A related method for diagnosing spermiogenesis in a mammal involves comparing (i) the pattern of the distribution of tyrosine kinase c-Yes throughout mature spermatozoa of the mammal with (ii) the pattern of the distribution of tyrosine kinase c-Yes throughout healthy, mature spermatozoa, wherein an abnormal distribution pattern is an indication that spermiogenesis in the mammal is abnormal.

The invention also features a transgenic non-human mammal whose germ cells contain a disruption in the endogenous gene encoding PT32, e.g., by insertion of a selectable marker sequence at the PT32 locus, and the disruption results in the lack of expression or function of PT32. Preferably, the non-human mammal is murine, bovine, or a monkey. Optionally, the animal may be bovine. Such an animal can be used as an animal model for studying human fertility and reproductive biology, as sperm produced from such animals can be expected to be defective (e.g., globozoospermic), and such animals can be expected to have diminished fertility.

Additionally, such an animal can be used as an animal model for screening compounds to identify modulators of oocyte activation. For example, such an method can include contacting an oocyte with (i) sperm produced by the transgenic non-human mammal, and (ii) a test compound, and detecting an inhibition or enhancement of oocyte activation as an indicator that the test compound is a modulator of oocyte activation. If desired, the transgenic non-human animals of the invention can be used as negative control animals for comparison to wild-type animals.

Also included within the invention is a transgenic non-human mammal whose germ cells contain a disruption in the endogenous gene encoding tyrosine kinase c-Yes, wherein the disruption comprises the insertion of a selectable marker sequence, and wherein the disruption results in the lack of expression or function of the tyrosine kinase c-Yes. Such animals (e.g., mice, monkeys, etc) can be used as animal models in studies of human fertility and reproductive biology.

In a related aspect, the invention includes a method for identifying a modulator of oocyte activation, the method comprising contacting an oocyte of the above-described transgenic non-human mammal having a disrupted c-Yes gene with (i) a test compound and (ii) spermatozoa, and detecting inhibition or enhancement of oocyte activation as an indicator that the test compound is a modulator of oocyte activation.

These and other aspects of the present invention should be apparent to those skilled in the art from the teachings herein.

BRIEF DESCRIPTION OF THE DRAWINGS/FIGURES

FIG. 1A is an image of a coomassie blue-stained 8 to 18% linear gradient SDS-polyacrylamide gel of a bull sperm head NaOH extract (Step 3 of perinuclear theca extraction protocol), showing localization of PT32 (*) in relation to other more prominent perinuclear theca polypeptides (PT). Lane S, standards (units in kDa). FIG. 1B is a western blot of a bull sperm head NaOH extract immunostained with $1^{st}$ (lane 1) and $2^{nd}$ (lane 2) boosts of anti-sera raised in a rabbit against the whole NaOH extract. The antigenicity of the $1^{st}$ boost towards a 32 kDa polypeptide was exploited in the immuno screening of a bull testicular cDNA expression library.

FIG. 2 is a listing of the nucleotide and amino acid sequences of the testicular specific PT32 protein. The largest open reading frame encoding a 313 amino acid polypeptide commences at nucleotide 36 and terminates at nucleotide 975. The stop codon, TAG, is shown. The polyadenylation signal sequence is indicated by ▫▫▫▫▫▫from bases 1374-1379. Two oligopeptides (amino acids 54-87 and 277-292, in bold letters and numbered by ① and ②) were generated for antibody production. The underlined and bracketed sequences indicate a unique and repeating sequence motif found in PT32, YGXPPXG (SEQ ID NO:3) (where X represents any amino acid residue). The PY motif, PPXY (SEQ ID NO:8), is positioned at amino acids 183-186 and 281-284. The first bracketed region highlights an overlapping region of both the unique PT32 motif and the PY motif.

FIG. 3A is an amino acid sequence alignment of bovine PT32 and mouse somatic WBP2. FIG. 3B is an amino acid sequence alignment of bovine PT32 and mouse testicular WBP like protein (WBPM).

FIG. 4A is an amino acid sequence alignment of bovine PT32 and human WBP2 like protein (WBPH). These two proteins share 54% global sequence identity. The YGXPPXG (SEQ ID NO:3) motif and PY motif (SEQ ID NO:8) are present in WBPH. FIG. 4B provides the nucleotide and deduced amino acid sequences of htWBP (human testicular WW domain Binding Protein). The ORF contains 708 nt which translate to 235 amino acid residues. The sequences of the primers used to obtain this clone are in bold fonts and indicated by the numbered arrow heads. The underlined sequence from amino acids 61 to 97 represents a sequence that was not found in WBPH. The unique YGXPPXG (SEQ ID NO:3) motif is depicted by ([ ]) and in bold font. The PY motif is in bold font and underlined. The stop codon TAA is indicated by (•••).

Figure 5:
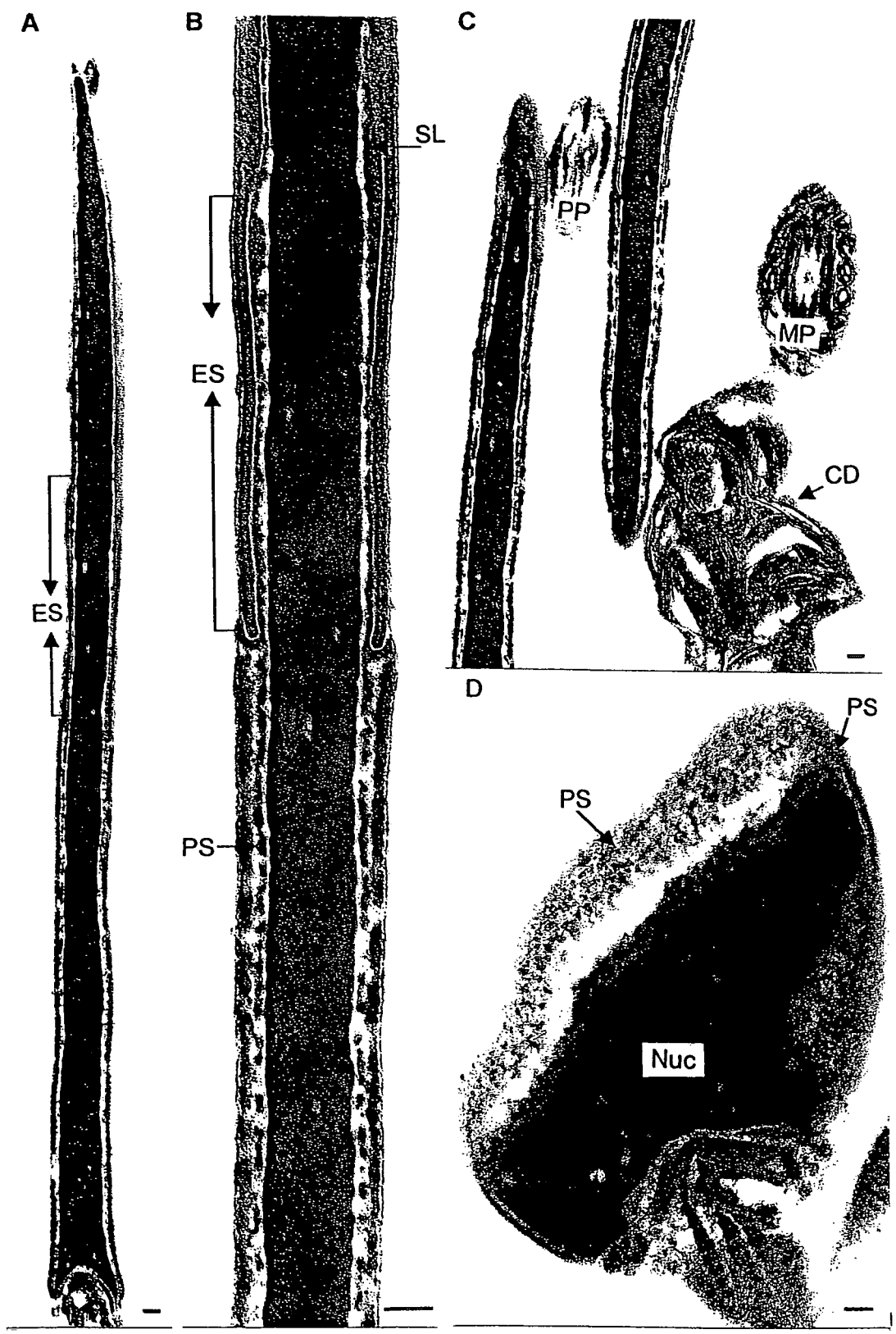

FIGS. 5A-5D are electron micrographs of cauda epididymal bull sperm sections immunogold-labeled with affinity-purified anti-rPT32 serum. FIG. 5A is a sagittal section through the whole sperm head. FIG. 5B is a higher magnification sagittal section providing more detail. PT32-labeling is restricted to the postacrosomal sheath (PS). Sperm membranes appear as white lines. FIG. 5C is a survey section through cauda epididymal sperm exposing the sperm head, cytoplasmic droplet (CD), mid-piece (MP) and the principal piece (PP) of the tail. FIG. 5D is an oblique section through the caudal face of the bull sperm head exposing the immunogold-labeled postacrosomal sheath. Note that PT32 is evenly distributed over the surface of the PS. The double-layered nuclear envelope can be seen clearly in the upper right hand corner (asterisk). Nuc, nucleus. Bars, 0.2 μm.

FIGS. 6A-6C show immunofluorescence labeling of PT32 with anti-oN32 in bull spermatozoa (FIG. 6A), Rhesus monkey spermatids (FIG. 6B), and Rhesus monkey spermatozoa (FIG. 6C). In bull sperm and Rhesus spermatids, labeling is in the postacrosomal sheath and equatorial segment regions. In the mature Rhesus sperm, labeling is confined to the equatorial segment. PT32, which stained green, and DNA, which stained blue by DAPI, were detected.

Figure 7:
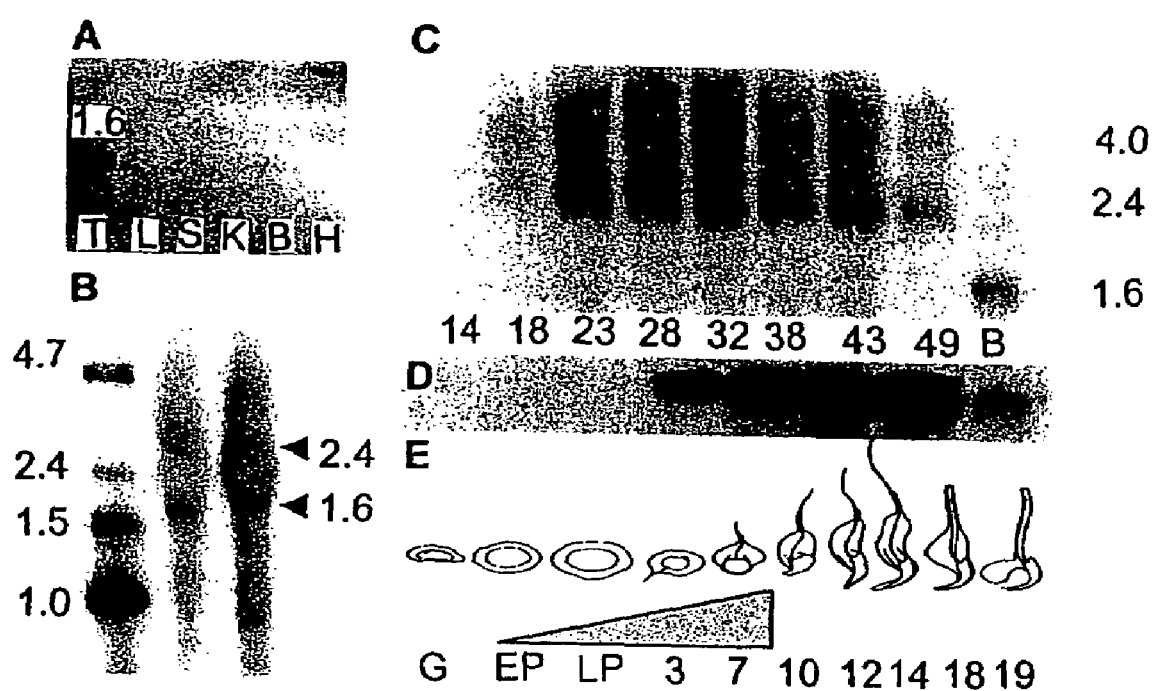

FIGS. 7A-7E show RNA obtained from various tissues probed with PT32 anti-sense RNA. FIG. 7A is a tissue comparative blot. Each lane was loaded with 10 µg of total RNA obtained from various tissues of the bull: T, testis; L, liver; S, spleen; K, kidney; B, brain; H, heart. FIG. 7B is a species comparative blot. Bull (B) and human (H) lanes were loaded with 5 µg of testicular RNA. In bull, one major 1.6 kb band was detected, whereas two major signals at 1.6 and 2.4 kb were found in human. FIG. 7C shows the developmental analysis of 5 µg samples of total RNA from testis of rats at 14 to 49 days of age. Lane B is bull testis total RNA sample used as control. FIG. 7D represents the same blot as above stripped and rehybridized with an antisense riboprobe made from an outer dense fiber cDNA. FIG. 7E is a schematic representation of the relative quantity and distribution of PT32 transcripts during rat spermatogenesis. The right-angle triangle depicts the gradual increase of PT32 mRNA(s) from early pachytene (EP) to the early spermatid elongation phase of spermiogenesis (steps 7-10). G, spermatogonia; LP, late pachytene. The numbers indicate the spermatid developmental steps.

FIGS. 8A-8J show that injection of rPT32 or PT extracts induced clustering of intrinsic c-Yes kinase in oocytes. FIG. 8A shows oocytes were fixed at metaphase-II prior to microinjection. FIG. 8B shows the oocytes at 20 hours after injection of rPT32. FIG. 8C shows oocytes that received crude PT extracts. FIG. 8D shows oocytes that received BSA-V. FIG. 8E shows oocytes after 20 hours of culture in fertilization medium, without injection. FIGS. 8F and 8G show the partial overlap of c-Yes speckles (which stained red) with ER marker α-PDI (which stained green). FIG. 8H shows the clustering of c-Yes in the cytoplasm of an oocyte fertilized in vitro by a spermatozoon (sperm tail mitochondria were rendered green by MitoTracker green FM). FIG. 8I shows the assembly of the nuclear pore complexes (NPC; which stained red) and cytoplasmic, NPC-containing annulate lamellae in an oocyte injected with rPT32. FIG. 8J shows the occurrence of c-Yes-positive foci in the cytoplasm of oocytes injected as described above, as demonstrated by subjective evaluation after immunofluorescence labeling. Representative images of oocytes with low, medium and high clustering of c-Yes are shown in FIGS. 8A, 8C and 8D, respectively. As shown in FIG. 8B, the left oocyte displays a medium and the right oocyte a high level of c-Yes clustering. Spindle and midbody microtubules (FIGS. 8A and 8B, which stained green) were labeled with anti-β-tubulin antibody E7, DNA (FIGS. 8A-8B, which stained blue) with DAPI.

FIGS. 9A-9G shows bovine oocytes undergo cell cycle activation, pronuclear development and cortical granule exocytosis upon the microinjection of recombinant c-Yes alone (FIGS. 9B and 9C), or in combination with recombinant c-Yes adapter-binding protein-like perinuclear theca protein PT32 (FIGS. 9D, 9E). Note that the partial loss of CG in the activated oocytes (FIGS. 9B and 9D, left oocyte in FIG. 9C) that resulted in the loss of typical patchy pattern of CG distribution, seen in the oocytes that were not activated by microinjection and remained arrested in the metaphase of second meiosis (FIG. 9C, right oocyte; FIG. 9E; metaphase plates of chromosomes are present). Control, uninjected oocytes (FIG. 9A) and control oocytes injected with vehicle buffer without recombinant proteins (FIGS. 9F and 9G) did not become activated and displayed a metaphase-II arrangement of chromosomes along with patchy distribution of cortical granules. DNA was counterstained by DAPI (which stained blue).

FIG. 10 is a listing of the amino acid sequence of an exemplary c-Yes protein. The sequence of this protein also can be found in the SWISSPROT database under accession number P09324.

DETAILED DESCRIPTION OF THE INVENTION

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereaux, J., eds., M Stockton Press, New York, 1991). While there exist a number of methods to measure identity between two polynucleotide or polypeptide sequences, the term "identity" is well known to skilled artisans (Carillo, H., and Lipton, D., SIAM J Applied Math (1988) 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., SIAM J Applied Math (1988) 48:1073. Methods to determine identity and similarity are provided by computer programs. Preferred computer program methods to determine identity and similarity between two sequences include, but are not limited to, GCS program package (Devereux, J., et al., *Nucleic Acids Research* (1984) 12(1):387), BLASTP, BLASTN, FASTA (Altschul, S. F. et al., *J. Molec. Biol.* (1990) 215:403).

As an illustration, by a polynucleotide having a nucleotide sequence having at least, for example, 95% "identity" to a reference nucleotide sequence, is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

Similarly, by a polypeptide having an amino acid sequence having at least, for example, 95% "identity" to a reference amino acid sequence, is intended that the amino acid sequence of the polypeptide is identical to the reference sequence except that the polypeptide sequence may include up to five amino acid alterations per each 100 amino acids of the reference amino acid. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxyl terminal positions of the reference amino acid sequence or anywhere between those terminal positions, interspersed either individually among residues in the reference sequence or in one or more contiguous groups within the reference sequence.

The present invention further relates to polynucleotides which hybridize to PT32 as set forth in SEQ ID NO:4 or SEQ ID NO:11 if there is at least 65%, preferably at least 75% or 90%, and more preferably at least 95% identity between the sequences. The present invention particularly relates to polynucleotides which hybridize under stringent conditions to PT32 as set forth in SEQ ID NO:4 or SEQ ID NO:11. As herein used, the term "stringent conditions" means hybridization in 6× sodium chloride/sodium citrate (SSC) at about 45° C., followed by one or more washes in 0.2×SSC, 0.1% SDS at 50-65° C. The polynucleotides which hybridize to the polynucleotides described herein (e.g., to SEQ ID NO:4 or 11), in a preferred embodiment, encode polypeptides which retain substantially the same function as the PT32 polypeptides of the invention (e.g., binding to c-Yes and/or activation of oocyte induction).

Alternatively, the polynucleotide may have at least 20 bases, preferably 30 bases, and more preferably at least 50 bases which hybridize to a PT32 polynucleotide under stringent conditions, as set forth in SEQ ID NO:4 or 11, and which has an identity thereto, as herein described, and which may or may not retain activity. For example, such polynucleotides may be employed as probes for the polynucleotides described herein, for example, for recovery of the polynucleotide or as a PCR primer.

Thus, the present invention is directed to polynucleotides having at least 65% identity, e.g., at least 75% or 90% identity, and preferably at least a 95% identity, to a polynucleotide which encodes PT32, e.g., the polypeptide of SEQ ID NO:5 or SEQ ID NO:12 (which can be encoded by the polynucleotide of SEQ ID NO:4 or 11), as well as fragments thereof, which fragments have at least 20 bases, and preferably at least 30 or 50 bases, and to polypeptides encoded by such polynucleotides.

The present invention also relates to vectors which include polynucleotides of the present invention, host cells which are genetically engineered with vectors of the invention, and the production of polypeptides of the invention by recombinant techniques. Cell-free translation systems can also be employed to produce such proteins using RNAs derived from the DNA constructs of the present invention.

Host cells are genetically engineered (e.g., transduced, transformed, or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants, or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, non-chromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art, such as Sambrook et al., MOLECULAR CLONING: A LABORATORY MANUAL, 2nd Ed., Cold Spring Harbor Laboratory Press, Cold Spring Harbor, N.Y. (1989)(the disclosure of which is hereby incorporated by reference).

The DNA sequence in the expression vector is operatively linked to an appropriate expression control sequence(s) (promoter) to direct mRNA synthesis. As representative examples of such promoters, there may be mentioned: an LTR or SV40 promoter, the $E.$ $coli$ lac or trp promoters, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in $E.$ $coli$.

The vector containing the appropriate DNA sequence as described herein, as well as an appropriate promoter or control sequence(s), may be employed to transform an appropriate host to permit the host to express the protein. Introduction of polynucleotides into host cells can be effected by methods described in many standard laboratory manuals, such as Davis et al., BASIC METHODS IN MOLECULAR BIOLOGY (1986) and Sambrook et al., MOLECULAR CLONING: A LABORATORY MANUAL, 2nd Ed., Cold Spring Harbor Laboratory Press, Cold Spring Harbor, N.Y. (1989) such as calcium phosphate transfection, DEAE-dextran mediated transfection, transduction, microinjection, cationic lipid-mediated transfection, electroporation, transduction, scrape loading, ballistic introduction, or infection.

Examples of appropriate hosts include, without limitation, bacterial cells, such as Streptococci, Staphylococci, E. coli, Streptomyces and Bacillus subtilis; fungal cells, such as yeast cells and Aspergillus cells; insect cells such as Drosophila S2 and Spodoptera Sf9 or Sf21 cells; and animal cells such as CHO, COS, HeLa, C127, 3T3, BHK, HEK 293 and Bowes melanoma cells. Animal cells, particularly human or bovine cells, are preferred. Such host cells can be somatic cells or germ cells; artisans of ordinary skill can readily select a cell type suitable to artisan's purpose.

A variety of expression systems can be used to produce the polypeptides of the invention. Such systems include, inter alia, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., MOLECULAR CLONING, A LABORATORY MANUAL (supra).

More particularly, the present invention also includes recombinant constructs comprising one or more of the sequences as broadly described above. The constructs include a vector, such as a plasmid or viral vector, into which a polynucleotide sequence of the invention has been inserted, in a forward or reverse orientation. In a preferred aspect of this embodiment, the construct also includes regulatory sequences, e.g., a promoter operably linked to the polynucleotide sequence of the invention. Suitable vectors and promoters are known to those of skill in the art, and are commercially available. The following vectors are provided by way of example. Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); ptrc99a, pKK223-3, pKK233-3, pDR540, pRIT5 (Pharmacia). Eukaryotic: pWLNEO, pSV2CAT, pOG44, pXT1, pSG (Stratagene) pSVK3, pBPV, pMSG, pSVL (Pharmacia).

Promoter regions can be selected from any desired gene using CAT (chloramphenicol transferase) vectors or other vectors with selectable markers. Two appropriate vectors are PKK232-8 and PCM7. Exemplary bacterial promoters include lacI, lacZ, T3, T7, gpt, lambda $P_R$, $P_L$ and trp. Exemplary eukaryotic promoters include CMV immediate early, HSV thymidine kinase, early and late SV40, LTRs from retroviruses, and mouse metallothionein-I promoters. Selection of the appropriate vector and promoter is well within the level of ordinary skill in the art.

For secretion of the translated protein into the lumen of the endoplasmic reticulum, into the periplasmic space or into the extracellular environment, appropriate secretion signals may be incorporated into the desired polypeptide. These signal sequences may be heterologous to the polypeptides of the invention.

In a further embodiment, the present invention relates to host cells containing the above-described constructs. The host cell can be a higher eukaryotic cell, such as a mammalian cell (e.g., a germ cell or a somatic cell), or a lower eukaryotic cell, such as a yeast cell, or the host cell can be a prokaryotic cell, such as a bacterial cell. Introduction of the construct into the host cell can be effected any of a variety of art-known methods, such as microinjection, calcium phosphate transfection, DEAE-Dextran mediated transfection, or electroporation (Davis, L., Dibner, M., Battey, I., Basic Methods in Molecular Biology, (1986)). The constructs in host cells can be used in a conventional manner to produce the gene product encoded by the recombinant sequence. Alternatively, the polypeptides of the invention can be synthetically produced by conventional peptide synthesizers.

As used herein, the term "polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslational natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1-12 in POSTTRANSLATIONAL COVALENT MODIFICATION OF PROTEINS, B C. Johnson, Ed., Academic Press, New York, 1983; Seifter et al., "Analysis for protein modifications and non-protein cofactors," *Meth Enzymol* (1990) 182:626-646 and Rattan et al., "Protein Synthesis: Posttranslational Modifications and Aging", *Ann NY Acad Sci* (1992) 663:48-62.

The terms "fragment," "derivative," and "analog" when referring to the polypeptides of the invention mean a polypeptide which either retains substantially the same function as a reference polypeptide, e.g., retains the ability to bind to c-Yes or PT32, or which retains a biological activity of the reference polypeptide, e.g., retains the ability to induce oocyte activation.

The polypeptide of the present invention may be a recombinant polypeptide, a natural polypeptide, a synthetic polypeptide, or a semi-synthetic polypeptide, preferably a recombinant polypeptide.

The fragment, derivative or analog of the polypeptide of the invention may be, without limitation, (i) one in which one or more of the amino acid residues are substituted with a conserved or non-conserved amino acid residue (preferably a conserved amino acid residue) and such substituted amino acid residue may or may not be one encoded by the genetic code, (ii) one in which one or more of the amino acid residues includes a substituent group, (iii) one in which the polypeptide is fused with another compound, such as a compound to increase the half-life of the polypeptide (for example, polyethylene glycol), (iv) one in which additional amino acids are fused to the polypeptide, e.g., employed for purification of the polypeptide, (v) one which contains a proprotein sequence, or (vi) one in which a signal sequence is fused to the polypeptide. Such fragments, derivatives, and analogs are deemed to be within the scope of those skilled in the art from the teachings herein.

The polypeptides of the present invention include the sequence set forth herein as SEQ ID NO:5, as illustrated in FIG. 2, and SEQ ID NO:12, as illustrated in FIG. 4B, as well as polypeptides that have at least 75% similarity (preferably at least 75% identity), preferably at least 90% similarity (more preferably at least 90% identity), to such polypeptides, and still more preferably at least 95% similarity (still more preferably at least 95% identity) to such polypeptides. As known in the art "similarity" between two polypeptides is determined by comparing the amino acid sequence and its conserved amino acid substitutes of one polypeptide to the sequence of a second polypeptide. Conservative substitutions are described in the patent literature, for example, in U.S. Pat. No. 5,264,558. It is thus expected, for example, that interchange among non-polar aliphatic neutral amino acids glycine, alanine, proline, valine and isoleucine would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could possibly be made, as could substitutions among the charged basic amino acids, lysine and arginine. Substitutions among the aromatic amino acids, including phenylalanine, histidine, tryptophan and tyrosine could also possibly be made. These sorts of substitutions and interchanges are well known to those of skill in the art. Other substitutions might well be possible. It would be expected that the greater the percentage of sequence similarity of a variant protein with a reference (e.g., naturally occurring) protein, the greater the degree of biological activity retained. Of course, as conservatively substituted variants having the activity of PT32 as described herein are intended to be within the scope of this invention, so are polynucleotides encoding such variants.

Also included are portions of such polypeptides, including antigenic portions of the polypeptide, which generally contain at least 8 amino acids and more preferably at least 10 amino acids. Biologically active portions of such polypeptides are included, which generally contain at least 5 domains (preferably 6, 7, 8, 9, 10, 11, 12, or more domains) that include the amino acid sequence YGXPPXG (SEQ ID NO:3). Preferably, such portions also contain the amino acid sequence PPPGY (SEQ ID NO:1). Such portions of the polypeptide also are expected to be c-Yes binding portions. If desired, the biological activity of a given polypeptide can be measured by measuring the ability of the polypeptide to activate oocyte induction, e.g., using method described herein. The ability of a particular polypeptide to bind to c-Yes can be measured, if desired, in a conventional assay of protein-protein interactions, e.g., in a co-immunoprecipitation assay, in a two-hybrid assay, or in an in situ immunoassay (e.g., as described herein).

Fragments or portions of the polypeptides of the present invention may be employed for producing the corresponding full-length polypeptide by peptide synthesis; therefore, the fragments may be employed as intermediates for producing the full-length polypeptides. Similarly, fragments or portions of the polynucleotides of the present invention may be used to synthesize full-length polynucleotides of the present invention. Preferred fragments of the polypeptides of the present invention or fragments of the nucleotide sequence coding therefor, include, for example, truncation polypeptides having the amino acid sequence of a PT32 polypeptide, except for deletion of a continuous series of residues that includes the amino terminus, or a continuous series of residues that includes the carboxyl terminus, or deletion of two continuous series of residues, one including the amino terminus and one including the carboxyl terminus. Also preferred are fragments characterized by structural or functional attributes, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are antigenic fragments, biologically active fragments (including those with a similar activity, or an improved activity, or with a decreased undesirable activity), fragments that are immunogenic in an animal (especially in a human or bull), and fragments that bind to tyrosine kinase c-Yes. A given fragment may have more than one of the aforementioned properties. For example, a given fragment may be both biologically active and antigenic.

The polypeptides of the invention can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli or the S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in an appropriate phase with translation initiation and termination sequences, and, preferably, a leader sequence capable of directing secretion of translated protein into the periplasmic space or extracellular medium. Optionally, the heterologous sequence can encode a fusion protein, such as a protein that includes an identification peptide (e.g., a hexahistidine tag) imparting desired characteristics, e.g., stabilization or simplified purification of expressed recombinant product.

Useful expression vectors for bacterial use are constructed by inserting a DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotech, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, such methods are well know to those skilled in the art. If desired, the polypeptides of the invention may be solubilized from plasma membranes in digitonin using conventional techniques.

Various mammalian cell culture systems can also be employed to express recombinant protein. Examples of mammalian expression systems include the COS-7 lines of monkey kidney fibroblasts, described by Gluzman, *Cell* 23:175 (1981), and other cell lines capable of expressing a compatible vector, for example, the C127, 3T3, CHO, HeLa, HEK and BHK cell lines. Mammalian expression vectors may comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 splice, and polyadenylation sites may be used to provide the required non-transcribed genetic elements.

The polypeptides of the invention can be recovered and purified from recombinant cell cultures by methods such as those including ammonium sulfate or ethanol precipitation, acid extraction, anion or cation exchange chromatography, phosphocellulose chromatography, hydrophobic interaction chromatography, affinity chromatography, hydroxylapatite chromatography, metal affinity chromatography (e.g., Ni-NTA), and lectin chromatography. Optionally, high performance liquid chromatography (HPLC) can be employed in the purification steps. Protein refolding steps can be used, as necessary, in completing configuration of the polypeptide.

The present invention also relates to the use of the polynucleotides described herein (e.g., a polynucleotide encoding PT32) for use as diagnostic reagents. For example, detection of a mutated form of PT32 provides a diagnostic tool that can add to, or define, a diagnosis of a disease or susceptibility to a disease which results from under-expression, over-expression or altered expression of PT32. For example, mutations in the PT32 gene can result in alterations in the shape or spermatozoa and/or cause (or contribute to) diminished fertility in a mammal. Mutations in the PT32 gene may be detected at the DNA level by a variety of conventional techniques.

Nucleic acids for diagnosis may be obtained from a subject's cells or bodily fluids, such as from spermatozoa, blood, urine, saliva, tissue biopsy, or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled PT32 nucleotide sequences or fragments thereof. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et al., *Proc Natl Acad Sci USA* (1985) 85: 4397-4401. In another embodiment, an array of oligonucleotide probes comprising PT32 nucleotide sequences or fragments thereof can be constructed to conduct efficient screening of, e.g., genetic mutations. Array technology methods are well known and have general applicability and can be used to address a variety of questions in molecular genetics including gene expression, genetic linkage, and genetic variability. (See for example M. Chee et al., *Science* 274: 610-613 (1996)).

The invention also provides a method for assessing the quality of spermatozoa. The method involves measuring the level of PT32 expression in the sperm of a mammal (e.g., a human or cattle), and comparing the level of PT32 expression with the level of PT32 expression found in normal mammals of the same species. A depreciation in the level of PT32 expression in the mammal (e.g., a 15%, 25% 50% depreciation or more) indicates that the mammal's sperm are of diminished quality. Mammals having diminished levels of PT32 expression are impaired in their ability to induce oocyte activation. Thus, the invention provides a method for determining whether a mammal has an impaired ability to induce oocyte activation. Such impairment may result in infertility of the mammal.

Biologically active polypeptides of the invention (e.g., PT32 and/or c-Yes) can be used in various assisted reproductive techniques (ART), including, but not limited to, intracytoplasmic sperm injection (ICSI) of impaired sperm (e.g., globozoospermic sperm) or of immature sperm; round spermatid injection (ROSI); and nuclear transfer (i.e., cloning) methods using somatic, embryonic, or germ cells. Such methods are well known in the art, as described, for examples in U.S. Pat. Nos. 6,050,935; 5,935,800; 5,908,380; 5,897,988; 5,882,928; 5,770,363; 5,691,194; 5,627,066; 6,066,725; 6,013,857; 6,011,197; 5,994,619; 5,952,222; 5,945,577; 5,942,435; 5,907,080; 5,863,528; 5,858,963; 5,849,991; 5,843,754; 5,817,453; and 5,741,957, and Eyestone and Campbell, *J. Reprod. Fert. Supp.* 54:489-497 (1999), each of which is incorporated herein by reference. See also Shiga et al. *Theriogenology* 52(3):527-35 (1999); Nour et al., *Theriogenology* February; 51(3):661-6 (1999); Booth et al. *Theriogenology* 51(5):999-1006. (1999); Trounson et al. *Reprod Fertil Dev.* 10(7-8):645-50 (1998); Karnikova et al. *Reprod Nutr Dev.* 38(6):665-70 (1998); Wolf et al. *Biol Reprod*. February; 60(2):199-204 (1999); Wolf et al., *J Biotechnol.* 65(2-3):99-110 (1998); Peura et al., *Mol Reprod Dev.* 50(2):185-91(1998); Zakhartchenko et al Mol Reprod Dev. 1997 November; 48(3):332-8; Wells et al., Biol Reprod. 1997 August; 57(2):385-93; Taniguchi et al. J Vet Med Sci. 1996 July; 58(7):635-40; Ouhibi et al. *Reprod Nutr Dev.* 1996; 36(6):661-6; Prochazka and Fiser Reprod Nutr Dev. 1995; 35(6):695-701; Yang et al. Mol Reprod Dev. 1993 May; 35(1):29-36; First and Prather, J Reprod Fertil Suppl. 1991; 43:245-54; and Czolowska et al. J Cell Sci. 1986 August; 84:129-38, each of which is incorporated herein by reference.

The use of recombinant proteins, such as recombinant PT32 and/or recombinant c-Yes, in ART offers advantages not provided by conventional methods for artificial activation of oocytes. Oocyte activation with crude sperm extracts may introduce into the oocyte sperm components that normally are removed before the sperm enters the egg, and which may be detrimental to embryonic development (e.g., the acrosome). In addition, sperm can carry viruses such as HIV and SIV, which may be propagated by using crude sperm extracts. Furthermore, ethical concerns are raised by the use of sperm extracts from male donors (i.e., "cytoplasmic fathers") in carrying out ICSI or ROSI. Such concerns can be avoided by using a recombinant protein, e.g., PT32 and/or c-Yes, to activate an oocyte.

The PT32 and c-Yes proteins also are useful in the field of contraception. Specifically, the PT32 and/or c-Yes protein can be used as targets in conventional immunocontraception methods. A variety of such methods have been described, and can readily be modified for use with the PT32 and c-Yes polypeptides described herein. Examples of conventional immunocontraceptive methods are disclosed in U.S. Pat. Nos. 6,045,799; 6,027,737; 6,013,770; 5,989,550; 5,989,549; 5,916,768; 5,753,231; and 5,672,488, each of which is incorporated herein by reference. Generally, an immunocontraceptively effective dose of the PT32 or c-Yes protein (or an antigenic fragment thereof) is administered to the mammal (e.g., human) to be treated. Preferably, a chimeric protein containing all or an antigenic portion of PT32 or c-Yes is administered to the mammal in a contraceptively effective dosage. The chimeric protein includes a carrier protein or fragment thereof, such as ovalbumin or KLH. The protein(s) of the present invention may be administered with a suitable diluent, adjuvant, carrier or in a depot (slow release) formulation to allow prolonged exposure of the protein to the host mammal's immune system. A contraceptively effective dosage is a dosage sufficient to elicit the production of an immune response (e.g., antibody or immune cell production) in the mammal.

The polypeptides of the invention, e.g., PT32, can also be used to identify test compounds (e.g., agonists and antagonists, such as small molecules and polypeptides) that bind to the polypeptides of the invention, or to measure the ability of test compounds to bind to the polypeptides. Such assays can be carried out, for example, in cells or in cell-free preparations. The test compound can be a natural, synthetic, or semi-synthetic substance, e.g., a structural or functional mimetic. See Coligan et al., *Current Protocols in Immunology* 1(2): Chapter 5 (1991). In a preferred embodiment, the invention includes a method for identifying test compounds that are agonists or antagonists (i.e., that promote or inhibit) the binding of PT32 to c-Yes. Such test compounds can be identified with conventional methods. For example, conventional two-hybrid methods for identifying compounds that affect protein-protein interactions are well known in the art and can be used in the invention, as described, for example, in U.S. Pat. Nos. 5,965,368; 5,955,280; and 6,004,746, each of which is incorporated herein by reference.

An exemplary potential antagonist is an antisense construct prepared through the use of antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes the polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.* 6:3073 (1979); Cooney et al., *Science* 241:456 (1988); and Dervan et al., *Science* 251:1360 (1991)), thereby preventing transcription and the production of the targeted polypeptide (e.g., PT32). The antisense RNA oligonucleotide hybridizes to the mRNA in vivo and blocks translation of the mRNA molecule into the polypeptide (antisense—Okano, J. *Neurochem.* 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of a polypeptide of the invention.

The polypeptides, antibodies, or test compounds (e.g., antagonists or agonists) of the invention may be employed in combination with a suitable pharmaceutical carrier or device. Such compositions comprise a therapeutically effective amount of the polypeptide or test compound, and a pharmaceutically acceptable carrier or excipient. Examples of such carriers and excipients include, but are not limited to, saline, buffered saline, dextrose, water, glycerol, ethanol, and combinations thereof. Optionally, the polypeptide, antibodies, or test compounds can be formulated with a carrier and/or device conventionally used for delivering contraceptive or fertility-enhancing agents. For example, conventional foams, gels, sponges, suppositories, creams, tablets, controlled delivery devices, vaginal-soluble waffles, ointments, lotions, sprays, jellies, patches, and lubricants (e.g., for condoms, diaphragms, cervical caps), and the like can be used in conjunction with the molecules of the invention. Suitable carriers and devices that can be modified to contain the molecules of the invention are well known in the art. Without limitation, examples are described in U.S. Pat. Nos. 5,725,870; 5,527,534; 4,795,761; 6,063,395; and 6,056,966, all of which are incorporated by reference herein. Such foams, creams, and the like can be administered, e.g., intravaginally, to a mammal to provide a contraceptive (e.g., a contraceptive barrier) in a contraceptive method (e.g., to inhibit fertilization), or to provide a fertility-enhancing agent in a method for enhancing fertility. As desired, the formulation can be optimized to suit the mode of administration. Polypeptides and other molecules of the present invention may be employed alone or in conjunction with other compounds, such as therapeutic or contraceptive compounds.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the compounds of the present invention may be employed in conjunction with other therapeutic compounds.

The pharmaceutical compositions may be administered in a convenient manner such as by topical, intravenous, intraperitoneal, intramuscular, subcutaneous, intranasal or intradermal routes. The pharmaceutical compositions are administered in an amount which is effective for treating and/or prophylaxis of the specific indication. In general, the various pharmaceutical agents described herein will be administered in an amount of at least about 10 µg/kg body weight and in most cases they will be administered in an amount not in excess of about 8 mg/Kg body weight per day. In most cases, the dosage is from about 10 µg/kg to about 1 mg/kg body weight daily, taking into account the routes of administration, symptoms, etc.

The polypeptides of the invention, and antagonists or agonists that are polypeptides, may be employed in accordance with the present invention by expression of such polypeptides in vivo, which is often referred to as "gene therapy." For an overview of gene therapy, see Chapter 20, "Gene Therapy and Other Molecular Genetic-based Therapeutic Approaches," (and references cited therein) in *Human Molecular Genetics*, T. Strachan and A P Read, BIOS Scientific Publishers Ltd (1996).

Thus, for example, cells (particularly spermatozoa) may be engineered in vivo for expression of a polypeptide in vivo by, for example, procedures known in the art. As known in the art, a producer cell for producing a retroviral particle containing RNA encoding the polypeptide of the present invention may be administered to a mammal (e.g., a human or a bovine mammal) for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retroviruses, for example, an adenovirus which may be used to engineer cells in vivo after combination with a suitable delivery vehicle.

Retroviruses from which the retroviral vectors may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques* 7(9):980-990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters (e.g., an adenoviral major late promoter), thymidine kinase (TK) promoters (e.g., a Herpes Simplex Virus thymidine kinase promoter), B19 parvovirus promoters, a respiratory syncytial virus (RSV) promoter; inducible promoters, such as the MMT promoter, the metallothionein promoter; heat shock promoters; the albumin promoter; the ApoAI promoter; human globin promoters; and human growth hormone promoters. The promoter also may be the native promoter which controls the genes encoding the polypeptides. Preferably, the promoter is a testis- or sperm-specific promoter to facilitate selective expression of the polypeptide in germ cells of the mammal. The selection of a suitable promoter will be apparent to those skilled in the art from the teachings contained herein.

The retroviral vector is employed to transduce packaging cell lines to form producer cell lines. Examples of packaging cells that may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5-14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral vector may be encapsulated into a liposome, or coupled to a lipid, and then administered to a host.

The producer cell line generates infectious retroviral particles that include the nucleic acid sequence(s) encoding the polypeptides. Such retroviral particles then may be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells. Preferably, the cell is a testicular cell, to facilitate expression of the polypeptide in germ cells of the mammal.

The present invention also provides a method for identifying polypeptides related to the polypeptides (e.g., PT32) of the present invention. These related polypeptides may be identified by homology to a polypeptide of the present invention, by low stringency cross hybridization, or by identifying polypeptides that interact with related natural or synthetic binding partners (e.g., c-Yes) and/or elicit physiological effects as the polypeptides of the present invention (e.g., induction of oocyte activation). The detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

The sequences of the present invention are also valuable for chromosome identification. The sequence is specifically targeted to, and can hybridize with, a particular location on an individual mammalian chromosome. Moreover, there is a current need for identifying particular sites on the chromosome. Few chromosome marking reagents based on actual sequence data (repeat polymorphisms) are presently available for marking chromosomal location.

Briefly, sequences can be mapped to chromosomes by preparing PCR primers (preferably 15-25 bp) from the cDNA encoding polypeptide of the invention (e.g., PT32). Computer analysis of the cDNA typically is used to rapidly select primers that do not span more than one exon in the genomic DNA. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance in Man* (available on line through Johns Hopkins University Welch Medical Library). The relationship between genes and diseases that have been mapped to the same chromosomal region are then identified through linkage analysis (co-inheritance of physically adjacent genes).

Next, it is necessary to determine the differences in the cDNA or genomic sequence between affected and unaffected subjects. If a mutation is observed in some or all of the affected subjects, but not in any normal subjects, the mutation is likely to be the causative agent of the disorder (e.g., infertility or abnormal spermiogenesis).

The polypeptides of the invention, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by introducing the polypeptides into an animal, e.g., a non-human mammal, such as a rabbit or mouse. The antibody so obtained will then bind the polypeptides of the invention. In this manner, even a sequence encoding only a fragment of the polypeptides can be used to generate antibodies binding the whole native polypeptides, as described further herein.

For preparation of monoclonal antibodies, any technique that provides antibodies produced by continuous cell line cultures can be used. Examples include the hybridoma technique (Kohler and Milstein, 1975, *Nature* 256:495-497), the trioma technique, the human B-cell hybridoma technique (Kozbor et al., 1983, *Immunology Today* 4:72), and the EBV-hybridoma technique to produce human monoclonal antibodies (Cole, et al., 1985, in *Monoclonal Antibodies and Cancer Therapy*, Alan R. Liss, Inc., pp. 77-96).

Techniques described for the production of single chain antibodies (e.g., U.S. Pat. No. 4,946,778) can be adapted to produce single chain antibodies to immunogenic polypeptides of the invention. Also, transgenic animals (e.g., mice) may be used to express humanized antibodies to immunogenic polypeptides of the invention.

The above-described antibodies may be employed, for example, to isolate or to identify cells expressing the polypeptide, or to purify the polypeptide by affinity chromatography. Alternatively, such antibodies can be used in immunoassays (e.g., in situ immunofluorescence studies or immunoprecipitation methods), or in passive immunocontraceptive methods.

The present invention also includes transgenic non-human mammals, particularly murine and bovine mammals, that have been altered to contain a sequence which confers a deficiency in the normal expression of PT32 and/or c-Yes. Similarly, non-human transgenic mammals that overexpress PT32 and/or c-Yes are included within the invention. The mammals of the present invention can be heterozygous or homozygous for the desired trait, provided that the mammals contain the altered PT32 coding sequence.

As used herein, a mammal is said to be altered to contain a sequence which conveys a deficiency in the normal expression of PT32 if recombinant techniques are utilized to insert, delete or replace sequences encoding for, or directing the expression of, PT32. The insertion, deletion or replacement within such sequences has the effect of altering the normal level of expression of the given sequence or altering the activity of the protein which is expressed.

Mammals can be altered such that the mammal expresses a lower level of the protein when compared to a non-altered mammal (in some cases a mammal "deficient" in expressing normal levels of a protein will be incapable of expressing detectable levels of the given protein). In some instances, where a mammal is altered such that a target gene is deleted or a large insertion is generated within the target sequence, the mammal will not produce detectable levels of the given protein. However, in some instances it may be possible for extremely low quantities of the protein to be produced, although such product may, in itself, be inoperative, or not functional in its usual physiological actions.

As used herein, "normal expression" is defined as the level of expression which is present in a wild-type or non-altered animal. A variety of techniques known in the art can be used to quantitate the level at which a given protein is expressed. These include, but are not limited to immunological techniques such as an ELISA, RIA, or western blot, or quantitative analytical techniques such as spectroscopy or flame chromatography.

Alternatively the mammals of the present invention can be altered so as to express an altered form of the given protein. Mammals can be altered such that a specific mutation is introduced into a given region of a PT32 protein.

The mammals of the present invention are preferably obtained by methods known in the art as homologous recombination (HR). This method has long been known in lower eukaryotes (e.g., yeast), and has also been described for the mouse (for review, see Capecchi, TIG 5(3):70-76 (1989) and also see Smithies et al., *Nature* 317:230 (1985); Zijlstra et al., *Nature* 342:435 (1989); Schwartzberg et al., *Science* 246:799 (1989); DeChiara et al., *Nature* 345:78 (1990)).

Homologous recombination essentially comprises isolating genomic sequences containing the target gene, employing known genetic engineering techniques to mutate or otherwise disable or modify the gene, and then reintroducing the gene into the relevant species. This is achieved by preparing a culture of pluripotent, or totipotent, cells, typically taken from embryos (ES cells). The advantage of these cells is that they can be successfully cultured for a large number of generations under conditions in which they will not differentiate and can be reintroduced into recipient embryos.

Typically the technique of electroporation, is used to render the ES cells capable of taking up exogenous DNA. The modified gene is then introduced, in a suitable manner, to these cells. Once taken up, recombination may occur, although this may be by random integration as well as by homologous recombination.

To select cells in which a recombination event has taken place, a selectable marker sequence may be used. For example, it is well known to employ the bacterial Neo gene to confer resistance to neomycin, or an analogue thereof, such as G418. The marker gene may be inserted in the gene to be modified, thereby disabling the target gene, while providing a positive selectable marker. Clones which are Neo+ have integrated the vector.

To further select homologous recombinants, the ends of the modified gene may have other markers inserted, such as the Herpes Simplex Virus thymidine kinase (HSVTK) gene. In a HR event, the HSVTK genes will not be recombined, and the marker will not be transferred. Therefore, the desired recombinant will be resistant to, for example, Gancyclovir, which is converted into a toxic metabolite when the HSVTK gene product is present (after a non-homologous recombination event).

Correct clones may be identified by the technique of PCR or by genomic Southern blotting. Subsequently, when a suitable clone has been identified, the ES cells may be injected into early-stage embryos, (blastocysts), and reintroduced into a pseudopregnant female. Chimeric animals will generally result from at least some of these embryos, their tissues deriving in part from the selected clone. Thus, the germ-line may also be chimeric, spermatozoa or ova containing the modified gene. Progeny deriving from such germ cells will be heterozygous for the gene. The heterozygous progeny can be cross-bred to yield homozygous animals. Confirmation of the allelic structure of the mammals can be ascertained by Southern blotting, for example.

The present invention also envisages cell lines suitable for generating mammals, particularly mice, of the invention, and techniques for generating such lines and mice. Thus, to obtain mice according to the present invention, one skilled in the art can use the strategy of homologous recombination (HR) in embryonic stem cells (ES cells) to replace the wild-type sequences encoding PT32 with an altered sequence.

The absence of PT32 in a cell line or animal allows one skilled in the art to screen for genes and agents which can restore the altered mice to a wild-type phenotype, as well as to screen for agents which act as agonists or antagonists of PT32. Such animals are particularly useful as a source of abnormal spermatozoa that can be used, for example, in studies of oocyte activation. In addition, such non-human mammals can be used as animal models in methods for treating humans. Additionally, the mammals of the present invention allow the investigation, at the cellular level as well as at the in vivo level, of a system which lacks PT32. This will allow researchers further to establish the importance of PT32. The animals and cells lines of the present invention may also be deficient in the expression of other genes, such as tyrosine kinase c-Yes, and thus provide the opportunity to study the interactions of PT32 and/or c-Yes with other proteins. Thus, it will be appreciated that there are many uses to which the mammals and cell lines of the present invention may be put. Artisans of ordinary skill will recognize that methods similar to the foregoing methods can be used to produce transgenic animals that are deficient in c-Yes expression, or to produce transgenic animals that overexpress PT32 and/or c-Yes.

The present invention will be further described with reference to the following examples; however, it is to be understood that the present invention is not limited to such examples. All parts or amounts, unless otherwise specified, are by weight.

In order to facilitate understanding of the following examples, certain methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accordance with conventional procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available, and their reaction conditions, cofactors and other requirements were used as would be known to the ordinarily skilled artisan. For analytical purposes, typically 1 µg of plasmid or DNA fragment is used with about 2 units of enzyme in about 20 µl of buffer solution. For the purpose of isolating DNA fragments for plasmid construction, typically 5 to 50 µg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction may electrophoresed directly on a gel to isolate the desired fragment.

"Oligonucleotides" refers to either a single stranded polydeoxyribonucleotide or two complementary polydeoxyribonucleotide strands, which may be chemically synthesized. Such synthetic oligonucleotides have no 5' phosphate and thus will not ligate to another oligonucleotide without adding a phosphate, e.g., with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase per 0.5 µg of approximately equimolar amounts of the DNA fragments to be ligated.

"Oocyte activation" means the initiation of the resumption of second meiosis by an oocyte. Typically, oocyte activation is accompanied by induction of anti-polyspermy defense and pronuclear development. Oocyte activation begins with the cyclic release of calcium ions from the oocyte's endoplasmic reticulum (i.e., "calcium oscillations"). Thus, oocyte activation can be detected by detecting the release of calcium ions, e.g., using a conventional assay. Ultimately, oocyte activation typically leads to the first embryonic cleavage. See, e.g., Perry et al., *Developmental Biol.* 217:386-393 (2000), incorporated herein by reference.

Generally, techniques described herein can be performed essentially as described in Sambrook et al., MOLECULAR CLONING: A LABORATORY MANUAL, 2nd Ed., Cold Spring Harbor Laboratory Press, Cold Spring Harbor, N.Y. (1989).

The following examples illustrate the present invention and the advantages thereof. These examples are set forth to illustrate the invention, not limit the scope of the invention.

EXAMPLES

The following materials and methods were used in the examples set forth herein. Alternative suitable materials and methods are known in the art and can be used in practicing the invention.

All patents, patent applications, and publications cited herein are incorporated herein by reference.

Extraction of Perinuclear Theca Extracts

Isolated bull and human sperm heads were exposed to three successive extractions. The first and second extractions solubilize the acrosome, head membranes, and hydrophobic and ionically bound proteins, leaving essentially a shell of insoluble perinuclear theca surrounding the condensed nucleus (Oko, R., and Maravei, D., *Biol. Reprod.* 50:1000-1014 (1994)). The first extraction was in 0.2% Triton X-100 for 1 hour, followed by centrifugation to obtain the sperm head pellet. Essentially all that remained was the rigid PT shell surrounding the condensed sperm nucleus. The second extraction step, in 1M NaCl, and the third extraction step, in 100 mM NaOH, were used to solubilize both non-covalently (SDS-soluble) and covalently (SDS-insoluble) bonded PT proteins, respectively, from the sperm head pellet. The supernatant recovered in this last extraction step (PT extract) was neutralized, dialyzed and lyophilized for use in SDS-PAGE analysis and western blotting as described previously by Oko and Maravei, *Biol. Reprod.* 50:1000-1014(1994). Upon examination by electron microscopy, the sperm head pellet remaining after the last extraction step consisted only of condensed nuclei. Also, all of the antibodies raised against this PT extract (see above reference), whether raised against the whole extract (pAB 427) or against each of its major proteins, exclusively immunolocalized to the PT of the sperm head, providing the confidence for the specificity of this extraction technique.

Differential Sperm Head Treatments

Isolated bull sperm heads underwent two cycles of freeze-thaw (freezing at −80° C. overnight and thawing at room temperature) followed by centrifugation. The supernatant, constituting the freeze-thaw extract, was then dialyzed and lyophilized for Western blot analysis, while the pellet was put through the 3 step extraction protocol above, and the final NaOH extract was immunoprobed.

Isolated bull sperm heads were treated with 0.1% Triton X-100 at 4° C. for 1 hour and pelleted by centrifugation. The pellet was washed 3 times with Tris-HCl in saline (25 mM TBS) at 4° C. The final pellet was incubated in 15 mM dithiothreitol (DTT) at 4° C. for 1 hour. The DTT-treated sample was then separated into supernatant (DTT-supernatant) and pellet (DTT-pellet) by centrifugation for subsequent immunoblot analysis.

Human, Rhesus Monkey and Bull Sperm and Spermatid Preparation

Frozen sperm from two anonymous donors suffering of sperm head defects reminiscent of partial globozoospermia were obtained with patients' consent from the Tohoku University Hospital, Sendai, Japan. Sperm counts in the fresh semen were $18.3 \times 10^6$ and $184.0 \times 10^6$. Sperm motility was 20% and 73.6%, respectively. Human sperm from a fertile, consenting donor were purchased from Follas Laboratories, Indianapolis, Ind. Prior to processing, sperm were thawed and washed by centrifugation through Tyrode's albumin-lactate-pyruvate medium with HEPES (TALP-HEPES).

Rhesus monkey semen was obtained from males having proven fertility that have been trained to routinely produce acceptable semen samples. After liquefaction of the coagulated ejaculate, the liquid semen was removed and washed three times in 10 mL of TALP-HEPES medium by centrifugation at 500×g for 5 minutes. After resuspension of the pellet in 1 mL TALP-HEPES, sperm were further diluted to a concentration of $20 \times 10^6$ sperm/mL in 1 mL equilibrated TALP medium (no HEPES), overlaid with 10 mL of mineral oil and incubated at 37° C. prior to use. Rhesus testes were obtained and cut open using a surgical knife. Blocks of tissue of approximately 10×10×5 mm in size were cut and transferred into a Petri dish with 35° C. warm TALP-HEPES medium, and minced using two fine forceps. Medium with the dispersed testicular cells was filtered through a 20 μm mesh to remove the debris and then collected into a 15 mL centrifuge tube. Cells were pelleted by centrifugation for 5 minutes at 500×g and fixed for immunofluorescence.

Straws of frozen bull sperm (ABS Global, DeForest, Wis.) were thawed and centrifuged for 10 minutes at 500×g through a two-layer Percoll gradient (45 and 90% in Sperm-TL medium). The sperm pellets were resuspended and incubated for 10 minutes at 37° C. in a modified Tyrode's medium (Serm-TL: Parrish, J. J., et al., *Theriogenology* 25:591-600 (1986); 100 mM NaCl, 3.1 mM KCl, 25 mM NaHCO$_3$, 29 mM NaH$_2$PO$_4$, 21.6 mM Na-lactate, 2 mM CaCl$_2$, 4 mM MgCl$_2$, 10 mM HEPES, 6 mg/mL bovine serum albumin, 25 μg/mL gentamicin, 1 mM pyruvate). For visualization of the sperm tails inside fertilized oocytes, sperm were incubated for 10 minutes in Sperm-TL medium supplemented with 400 nM MitoTracker Green FM (Molecular Probes Inc., Eugene, Oreg.), a vital mitochondrial dye with high affinity for sperm mitochondrial membranes (Sutovsky, P. et al., *Biol. Reprod* 55:1195-1205 (1996)) prior to in vitro fertilization. Labeled sperm were washed by a repeated resuspension and centrifugation in Sperm-TL medium. Bull testes were purchased from a slaughterhouse, and pieces of testicular tissue of approximately 10×10×5 mm were minced in a Petri dish filled with TL-HEPES medium. Collected testicular cells were filtered, centrifuged, and fixed for immunofluorescence as described for rhesus monkey tissues.

PT32 Antibody Preparation

Polyclonal serum was raised in a rabbit against the entire NaOH extract of sperm heads (from the third extraction step of the above protocol). The serum was used to immunoscreen a bull testicular cDNA expression library. The immunoscreening took advantage of the fact that the serum from the first boost (anti-PT serum) recognized only two of the extracted PT proteins on western blots: a 32 kDa protein (PT32) and a 15 kDa protein (PT15 or subH2Bv), the identity of which was known.

Once PT32 was cloned, polyclonal antibodies were raised in rabbits against two synthetic oligopeptides chosen from the N-terminus (amino acid residues TSYRVVFVT-SHLVNDPMLSFMMPF (SEQ ID NO:6), anti-oN32) and C-terminus (amino acid residues NEALPPAYEAPSAGNT (SEQ ID NO:7), anti-oC32) of the deduced open reading frame of the cDNA clone of bovine PT32. These antibodies were used to verify the authenticity of the clone on western blots of NaOH extracts and in sperm prepared for immunofluorescence.

The final immune sera were produced in rabbits against the entire open reading frame of recombinant PT32 protein (anti-rPT32) for the purpose of ultrastructural localization by electron microscopy. Each of the three antibodies (antioN32, anti-oC32, and anti-rPT32) was affinity purified before use on western blot-isolated recombinant PT32 according to the methodology of Oko and Maravei, *Biol. Reprod.* 50:1000-1014 (1994).

Cloning of cDNA Encoding PT32

Anti-PT serum, recognizing only PT32 and PT15, was used to screen a bull testicular ZAP EXPRESS™ cDNA library (Stratagene, LaJolla, Calif.) essentially following the method of Young and Davis, *Science* 222:778-782 (1983) and *Proc. Natl. Acad. Sci. USA* 80:1194-1198 (1983). Phagemids (pBKk-CMV) of six sequential positive clones were excised from a λ phage genome by transfecting them into XL-1 Blue cells in the presence of ExAssist helper phage. Subsequently the circularized, packaged and secreted phagemids were transformed into XLOLR cells with kanamycin selection. The selected colonies were grown for plasmid isolation (High Pure Plasmid Isolation Kit, Roche Diagnostics, Laval, QC), and inserts were released from the phagemid vectors by EcoRI and NotI restriction digests. The DNA was analyzed on 1.2% agarose gels. The phagemids of all six original clones, containing inserts of approximately 1.4 kb, were then sequenced. Because all of the clones were identical, only one clone (PT32 cDNA) was chosen for second and third rounds of sequencing, in which both DNA strands were sequenced completely.

Construction, Expression and Purification of Recombinant PT32

The open reading frame of the PT32 cDNA was subcloned into the pET28b vector (Novagen, Madison, Wis.) between the HindIII and XhoI sites. The nucleic acid sequence was then verified by sequence analysis. The pET28b recombinant construct was then transformed into *E. coli* BL21 DE3[PlyS] cells (Novagen, Madison, Wis.), which then were induced with 1 mM isopropyl-β-D-galactopyranoside for 4 hour at 37° C. to express PT32 protein. Subsequently the *E. coli* cells were pelleted and sonicated in lysis buffer (50 mMNaH$_2$PO$_4$, pH 8.0; 300 mM NaCl; 10 mM imidazole). To purify the His-tagged PT32 fusion protein, the bacterial lysate was incubated with a Ni-NTA agarose slurry (Qiagen, Mississauga, ON) overnight at 4° C., followed by three 10 minute washes. The fusion protein was washed in wash buffer (50 mM NaH$_2$PO$_4$, pH 8.0; 300 mM NaCl; 20 mM imidazole) and subsequently eluted with elution buffer (50 mM NaH$_2$PO$_4$, pH 8.0; 300 mM NaCl; 250 mM imidazole) on poly-prep chromatography columns (Bio-Rad, Mississauga, ON) and the His-tag was cleaved off from the fusion protein using thrombin. The protein was further purified on ion-exchange columns (Sigma, St. Louis, Mo.) before being analyzed by SDS-PAGE and immunoblotting. The recombinant protein was subsequently used for antibody production and micro-injection studies.

SDS-PAGE, Western Blotting and Immunoblotting

Lyophilized PT protein extracts, and bull and primate sperm were solubilized in 2% SDS-5% β-mercaptoethanol for 5-10 minutes at 100° C., and fractionated on either 8-18% linear gradient or 12% SDS—polyacrylamide discontinuous gels according to Laemmli, U. K., *Nature* 277: 680-685 (1970). The protein concentration of dialyzed PT proteins before lyophilization was determined using the Bio-Rad protein assay. Relative molecular masses of proteins were determined by comparison with the mobility of low molecular weight standards.

Proteins that were fractionated on SDS-PAGE were electrophoretically transferred from preparative gels to immobilin (0.45 µm pore size; Millipore, Mississauga, ON) using a Hoefer Transport Apparatus according to the transfer techniques proposed by Towbin et al, *J. Immunol. Meth.* 72:313-340 (1984). The specificity of anti-PT antibodies was tested on western blots using a secondary goat anti-rabbit IgG conjugated to alkaline phosphatase (Cappel-Cooper Biomedical, Inc., Malvern, Pa.). The phosphate reaction was developed using conventional techniques (McGadey, J., *Histochemie* 23:180-184 (1970)).

Northern-Blotting and Chemiluminescent Detection

Total RNA from various tissues was prepared using the RNeasy Mini-preparation kit (Qiagen, Mississauga, ON). It was mixed with sample buffer containing formaldehyde, formamide and MOPS. The RNA was denatured at 65° C. for 10 minutes before separation in 1.2% agarose-formaldehydegels. The gels were washed with 20×SSC (3M NaCl, 300 mM sodium citrate, pH 7.0) and transferred to nylon membrane (Roche Diagnostics, Laval, QC) in 20×SSC buffer. The RNA was then UV cross-linked at 125 mJ to the membrane using the GS Gene Linker (Bio-Rad Laboratories, Hercules, Calif.).

DIG-labeled sense and antisense ribo-probes were synthesized by in vitro transcription of the PT32 cDNA clone, and used for northern blot hydridization in accordance with the DIG System User's Guide for Filter Hybridization (Roche Biomolecular, Germany). Briefly, after prehybridization, the blots were incubated overnight a 68° C. in hybridization buffer containing 100 ng/mL DIG labeled ribo-probes and then washed twice at 21° C., blocked in blocking buffer, and incubated with alkaline phosphatase-conjugated Fab sheep anti-digoxygenin IgG. After two washes and equilibration in detection buffer, the blots were incubated between two sealed transparencies with a chemiluminescent substrate solution for 15 minutes at 37° C. before being placed over film for development.

RT-PCR of Total Testis RNA

The first strand cDNA template was generated using reverse transcription PCR from both the bull and human testis total RNA. For the bull cDNA template, the upstream primer (→1 in FIG. 4B) was designed from 6 nucleotides upstream of the start codon, 5'-GGCAGGGATGGCAGT-GAACCAG-3' (SEQ ID NO:13). The downstream primer (←2 in FIG. 4B) was obtained from the antisense sequence beyond the stop codon, 5'-GTCCATTTACCACCTTCTCA-GAG-3' (SEQ ID NO:14). The downstream primer was used in reverse transcription PCR to obtain the cDNA template of the total bull testis RNA using a SuperScript™ preamplification system (GibcoBRL, Burlington, ON). Both primers were then used for amplification of the cDNA at 50° C. for 30 cycles.

From a BLASTN search (Altschul et al., *Nucleic Acids. Res.* 25:3389-3402 (1997)), an uncharacterized human 678 bp cDNA sequence localized on chromosome 22 and demonstrating high sequence similarity to PT32 (65.6%), was obtained from the database of the *Homo sapiens* genomic contig sequences of the NCBI annotation project (Accession No. XM_001168). The first 18 nucleotides of this cDNA were used to design the upstream primer (5'-ATGC-CATTTGATCTGATG-3' (SEQ ID NO:15)), while the downstream primer was designed from the complementary nucleotides of 661 to 678 (5'-ATGGAGTAACAGTCCATC-3') (SEQ ID NO:16). The cDNA template was obtained using the downstream primer, and its amplification was generated using both upstream and downstream primers at 50° C. for 30 cycles. The products were analyzed by 1% agarose gel electrophoresis.

Subcloning and Sequencing of the Human PT32 Homolog

Human PT32 cDNA obtained by PCR was inserted into the pCRII-TOPO vector (Invitrogen, Carlsbad, Calif.). Positive clones were selected, and the DNA sequence of the insert was determined by sequencing.

Immunocytochemistry

Pieces (1 mm$^2$) of cauda epididymides obtained from bulls were immersed immediately after their slaughter in a fixative (0.8% glutaraldehyde and 4% paraformaldehyde in 0.1M phosphate-buffered saline (PBS), pH 7.2, 50 mM lysine (glut-parafix)). Following fixation, the tissue was washed in PBS and incubated overnight at 5° C. in PBS containing $NH_4Cl$. The tissue blocks were then rinsed in PBS, dehydrated in graded ethanol up to 90%, and infiltrated progressively with increasing gradients of LR White (Polysciences, Inc., Warrington, Pa.) in 90% ethanol until 100% concentration of LR White was achieved. After a final change of LR White containing 0.1% w/v Benzil, the embedded tissues in gelatin capsules were polymerized overnight under UV light at −20° C.

Bull testes collected immediately after slaughter were first cleared of blood by perfusion in saline through the testicular artery and then perfused with either Bouin's fixative for light microscopy (LM) or with glut-para fix for electron microscopy (EM). Tissue was prepared for paraffin embedding (LM) and Lowicryl-4M embedding (EM) according to conventional methods (Oko et al, *Mol. Reprod. Dev.* 44:1-13 (1996)). Immunoperoxidase staining and immunogold labeling of 5 μm paraffin and ultrathin LR White or Lowicryl sections, respectively, was also performed in accordance with conventional techniques.

Immunofluorescence

Immunofluorescence studies were carried out using antibodies directed against each of: c-Yes, nuclear pore complexes, PT32, perinuclear theca protein 15 (PT15), and whole perinuclear theca extracts (antibody pAb427). Fertilization was performed according to the protocol of Parrish et al., *Theriogenology* 25:591-600 (1986). Fertilized or microinjected bovine oocytes were stripped of zona pellucida by incubation for 5 minutes in TL-HEPES containing 0.5% w/v protease. The oocytes were then transferred into 9-well glass plates and fixed for 40 minutes in 2% formaldehyde in 0.1 M PBS, and then permeabilized for one hour in 0.1% Triton-X-100 in 0.1 M PBS. Nonspecific reactions were blocked by a 1 hour incubation in 0.1 M PBS containing 10% normal goat serum (NGS). The oocytes then were incubated in a 1/50 solution of the anti-c-Yes antibody sc-14 (Santa Cruz Biotechnology, Inc.) in 0.1 M PBS containing 0.05% $NaN_3$, 2 mM EGTA, 1% NGS and 0.1% Triton=X-100 (referred to herein as labeling solution). After a short wash in labeling solution, the oocytes were incubated for 40 minutes with rhodamine-conjugated goat-anti rabbit IgG (Zymed; diluted 1/80) and 5 μg/mL of DAPI (Molecular Probes Inc., Eugene, Oreg.), which was added to the solution 10 minutes before the end of incubation. After a wash in labeling solution, oocytes were mounted on microscopy slides in a VectaShield mounting medium (Vector Labs). Co-localization of the cytoplasmic c-Yes foci with endoplasmic reticulum (ER) was revealed by double labeling of the microinjected oocytes with anti-c-Yes/GAR-TRITC (above) and a mouse monoclonal antibody against the ER-resident protein disulfide-isomerase (PDI; MA3-019, Affinity BioReagents, Inc., Golden, Colo.; diluted 1/50), which was detected by a goat anti-mouse IgG-FITC (Zymed; diluted 1/80). To examine the formation of nuclear envelope and nuclear pore complexes after rPT32 microinjection, oocytes were incubated with a nucleoporin-specific mouse monoclonal antibody, mAb 414 (BabCo; Berkeley, Calif.; diluted 1/200; Sutovsky et al., *J. Cell. Sci.* 111:2841-2854 (1998)), followed by incubation with a TRITC-conjugated goat anti-mouse IgG and DAPI.

Bull and rhesus monkey sperm and testicular cells were attached to poly-L-lysine coated coverslips as described previously (Sutovsky et al., *Int. Rev. Cytol.* 195:1-65 (1999)) and fixed and processed for immunofluorescence as described above. Antisera against PT32 (PT32-1 and PT32-2) and an unrelated PT protein, PT15, were used at a 1/200 dilution and followed by goat anti-rabbit IgG-TRITC (Zymed; diluted 1/80) and DAPI. Images were acquired with a Zeiss Axiophot microscope.

As an alternative to the foregoing immunofluorescence method, the modified protocol of Sutovsky et al. (*Biol. Reprod* 55:1195-1205 (1996)) was used to visualize sperm PT, nuclear pores, DNA and sperm tail mitochondria inside zygotes. Fertilized oocytes were removed from the fertilization drops at various time points ranging from 8 hours (sperm incorporation) to 24 hours (first mitosis) after insemination and stripped of zonae pellucidae by 0.5% pronase in a serum-free TL-HEPES containing 0.5% polyvinyl-pyrolidone (PVP; Sigma), then attached to the poly-L-lysine coated microscopy coverslips in warm (37° C.) 0.1 M phosphate-buffered saline (PBS; pH 7.2). Formaldehyde was added to the dishes with oocytes to a final concentration of 2% and fixed for 40 minutes at room temperature (RT). Zygotes (e.g., derived from MitoTracker-tagged sperm) were permeabilized overnight in 0.1% Triton-X-100 (TX-100; Sigma) in 0.1 M PBS, blocked for 25 minutes with 5% normal goat serum (NGS; Sigma) in 0.1 M PBS with 0.1% TX-100 and incubated for 40 minutes at RT with a mixture of the perinuclear theca-specific rabbit polyclonal antibody pAb 427 (Oko, R., and Maravei, D., Biol. Reprod. 50:1000-1014(1994); diluted (dil.) 1/200) and nuclear pore-specific mouse monoclonal antibody mAb 414 (BabCo, Berkeley, Calif.; Davis, L. I., and Blobel, G., *Proc. Natl. Acad. Sci. USA* 84:7552-7556 (1987); Sutovsky, P., et al., *J. Cell Sci.* 111:2841-2854 (1998); dil., 1/200), or other antibodies, such as anti-PT32 antibodies, or anti-c-Yes antibodies (Santa Cruz Biotechnology), followed by a 40 minutes incubation with the red fluorescent, TRITC-conjugated goat anti-rabbit IgG and a far-red emitting, CyS-conjugated goat anti mouse IgG (both from Zymed Labs, South San Francisco, Calif.; both dil. 1/40). DNA was stained by 4',6'-diamidino-2-phenylindole (DAPI; Molecular Probes, Eugene, Oreg.) added at 5 μg/mL to the secondary antibody solution 10 minutes before the end of incubation. All antibodies were diluted, and the zygotes were washed between and after the antibodies in 0.1 M PBS containing 0.1% TX-100, 1% NGS and 0.05 $NaN_3$. The coverslips with zygotes were mounted on microscopy slides in a VectaShield mounting medium (Vector Labs, Burlingame, Calif.) and examined on a Zeiss Axiophot epifluorescence microscope equipped with an RTE/CCD 1217 camera (Princeton Instruments, Inc., Trenton, N.J.), operated by MetaMorph software. Images were recorded onto Iomega Jazz cartridges (Iomega Corp., Roy, Utah) and archived on recordable CDS. Due to its stability after formaldehyde cross-linking, the fluorescence of the Mitotracker-labeled sperm tail mitochondria was retained after such processing and allowed the discrimination between the male, sperm-tail tagged pronuclei, and female, tail-free pronuclei, Final images were created by pseudo-coloring and superimposing the parfocal single channel images using Adobe Photoshop 4.0 software (Adobe Systems Inc., Mountain View, Calif.). Final composite images (PT=red, NPC=green, DNA=blue, sperm mitochondria=white) were contrast-enhanced, edited and printed on Sony UP-D-8800 color video printer using Adobe Photoshop 4.0. Two hundred and fifty zygotes and 50 oocytes were processed with the above antibodies and 50 zygotes were processed with preimmune rabbit serum as a negative control.

Oocyte Preparation, In Vitro Fertilization and Intracytoplasmic Injection of Recombinant PT32 and PT Extracts Bovine oocytes were isolated by aspiration from ovaries obtained from a local abattoir (Walt's Meats Inc., Woodland, Wash.) and matured in vitro for 24 hours (metaphase-II) in TC 199 medium (Sigma, St. Louis, Mo.), supplemented with 10% fetal calf serum, 0.2 U/mL FSH-P (Schering-Plough Animal Health Corp., Kenilworth, N.J.), 0.2 M pyruvate and 25 µg/mL gentamicin. MitoTracker Green-FM-tagged sperm were added at a final concentration of $1 \times 10^6$ sperm/mL to fertilization medium (TL; Sutovsky et al., Hum. Reprod 11:1703-1712 (1996)) supplemented with 5 µg/mL heparin. Incubation was carried out at 39° C. in a humid atmosphere of 5% $CO_2$.

For microinjections, holding pipettes (approx. outer diameter 100 µm; inner diameter 20 µm) and microinjection needles (approx. O.D. 2 µm and I.D. 0.5-1 µm) were prepared using a Microforge and mounted on a Nikon Diaphot microscope equipped with Narishige micromanipulators and Hoffman modulation contrast (HMC) optics. Injections were carried out on a heated stage at 35° C. in TALP-HEPES medium. A 5 µl drop of RPT32, diluted to 0.5 mg/mL or 0.05 mg/mL (2.5 pg or 0.25 pg) in an injection buffer (modified KHM; 78 mM KCl, 50 mM HEPES, 0.5 mM $MgCl_2$, pH 7.0) was placed next to the drop with oocytes under mineral oil on a large, 10 cm Petri dish serving as a microinjection stage. Approximately 5 pl of PT extract (in some experiments, 20 pL) was aspirated into the injection pipette. Oocytes were immobilized with the polar body at 12 o'clock and the injection needle was inserted through the zona into oocyte cytoplasm. The oolemma was breached and proteins injected in the center of the cytoplasm. Injected oocytes were incubated in 50 mL drops of fertilization medium at 39° C. in 5% $CO_2$ for 24 hours prior to the assessment of activation and cleavage. Activation was determined after the processing of the oocytes for immunofluorescence with anti-c-Yes antibody and a DNA stain DAPI. The uninjected oocytes served as controls.

Transmission Electron Microscopy

Fertilized oocytes were fixed in formaldehyde-glutaraldehyde fixative of Ito, S., and Karnovsky, M. J., J. Cell Biol. 89:168 (1968), containing 5% 2-4-6 trinitrophenol (picric acid; Sigma), post-fixed in 0.1% osmium tetroxide, dehydrated by an ascending ethanol series (30-100%), perfused with a solution of acetone and Epon 812, and embedded in Epon 812 resin. Tissue sections were cut using a Sorvall MT 5000 ultramicrotome, transferred onto 100 MESH Cu-grids, stained with uranyl acetate and lead citrate, and examined and photographed on a Philips 300 electron microscope. Negatives were scanned by an Umax Power Look 3000 scanner and printed using Adobe Photoshop 4.0 software.

Perinuclear Theca-Oolemma Binding Assay

Bull sperm were processed as described above and deprived of their plasma membranes by a 20 minute incubation at 37° C. in 0.05% lysophosphatidyl-choline (Lysolecithin; Sigma) diluted in KNIT medium (100 mM KCl, 2 mM $MgCl_2$, 10 mM Tris-HCl; pH 7.0). Mature, metaphase-II -arrested live oocytes were deprived of zonae pellucidae as described for immunofluorescence and transferred into drops of fertilization medium. One million demembranated sperm/ml were mixed with zona free oocytes, cultured for 4 hours, and fixed for immunofluorescence (pAb 427/DAPI, or DAPI only) or electron microscopy as described above.

Results

Incorporation of the Sperm Perinuclear Theca Into Oocyte Cytoplasm During Natural Fertilization Labeling of fertilized oocytes with the PT-specific antibody pAb 427 was combined with a nuclear pore complex-specific (NPC-specific) antibody (mAb 414) and the DNA stain DAPI, and with the use of MitoTracker-tagged spermatozoa, in order to monitor the removal and incorporation of sperm PT at fertilization. With the exception of DAPI-stained maternal chromosomes, the unfertilized, metaphase II-arrested oocytes displayed neither of the above immunofluorescent labelings. The intact PT was found on the surface of the oocyte-bound spermatozoa at an early stage of fertilization, and PT-labeling acquired a fuzzy appearance in the spermatozoa undergoing incorporation into oocyte cytoplasm. Clumps of the PT-derived material were found next to the incorporated sperm nuclei when the new nuclear envelope, delineated by mAb 414-positive NPCs, reformed on their surface. Such clumps of PT-material were seen near the male pronucleus throughout the initial stages of pronuclear development, during which the female chromatin completed its second meiotic division, and the oocytes extruded the second polar bodies. Remnants of the PT were last seen in the zygotes in which the developing male and female pronuclei entered the process of pronuclear apposition. No PT-derived material was detected in zygotes reaching full pronuclear size and apposition, and in the spontaneously activated parthenogenetic oocytes. Such spontaneous parthenogenotes also displayed aberrant patterns of NPC assembly.

Ultrastructure of the Interactions Between Sperm Perinuclear Theca and Oocyte Cortex Despite the fact that the process of sperm incorporation occurs rapidly and is seldom documented by electron microscopy, we succeeded in observing the interactions between sperm PT and the oocyte cortex/cytoplasm in several specimens. During sperm-oolemma binding, the oocyte microvilli seemed to fuse with sperm plasma membrane and this new zygotic membrane remained attached to the sperm PT. Such binding of PT to the oolemma was also observed during sperm incorporation into oocyte cytoplasms, when the oocyte microvilli remained attached to the innermost leaf of PT, while the outer layers of PT became detached from the sperm nucleus and partially dissolved in the cytoplasm. The dissolution of the sperm PT in oocyte cytoplasm was also observed with a partially incorporated spermatozoon, the complete incorporation of which was prevented by polyspermy block. The cytoplasm of this oocyte contained one female and one sperm tail-tagged male pronucleus with no signs of PT. The post-acrosomal sheath of the head of second spermatozoon, protruding into the perivitelline space, contained an intact PT. In contrast, the incorporated apical segment of this sperm head contained no PT and displayed partially decondensed chromatin surrounded by a newly formed nuclear envelope. To support the observations on PT-oolemma binding, bull spermatozoa were demembranated with 0.05% lysolecithin to expose their PT and co-cultured for 16 hours with zona-free oocytes. This treatment resulted in a strong binding of oocyte microvilli to the PT of such spermatozoa.

These experiments indicate that the perinuclear theca of mammalian spermatozoa contains factor(s) capable of triggering oocyte activation at fertilization. All antibodies raised against whole PT extracts, including pAb427, exclusively label the PT of sperm prepared for immunocytochemistry (Oko, R., and Maravei, D., Biol. Reprod 50:1000-1014 (1994)) confirming the purity of the preparation. When the PT extracts prepared for this study were subjected to electrophoresis and Western blotting, the Coomassie blue-stained bands overlapped with those cross-reacting with the PT-specific polyclonal antibody pAb 427, with the exception of the non-reactive major 60 kDa band which was previously identified as PT 60 (Oko, R., and Maravei, D., *Biol. Reprod.* 50:1000-1014 (1994)).

Characteristics of Anti-PT Serum

The anti-PT serum used to immunoscreen the bull testicular cDNA expression library was raised in rabbits against the SDS-insoluble bull PT polypeptides shown in lane 1 of FIG. 1A. The sequence identities of most of the prominent PT polypeptides (i.e., the 15-, 24-, 28-, 31- and 60-kDa polypeptides, lane 1) are known. As can be seen, PT32 (arrows) is a less prominent member of this group although it appeared to be the most antigenic (lanes 1 and 2 of FIG. 1B). This cDNA immunoscreening took advantage of such heightened antigenicity and the fact that the anti-PT serum from the first boost (lane 1, FIG. 1B) only recognized PT32 and a 15 kDa PT protein (SubH2Bv) whose sequence identity was already known. This anti-PT serum reacted exclusively with the PT of bull sperm at the electron microscope level, immunolabeling both the subacrosomal and postacrosomal regions of the PT.

Isolation and Sequence of PT32 cDNA Clone

Six positive cDNA clones were obtained from immunoscreening of a bull testicular ZAP Express phagemid library using anti-PT serum (1$^{st}$ boost) and, after appropriate processing, the clones were sequenced and found to be identical. FIG. 2 sets forth the nucleotide sequence of the largest clone (PT32 cDNA, 1413 nts). The largest open reading frame (ORF) of this clone begins at nucleotide 36 and ends at nucleotide 975, encoding a protein of 313 amino acids with a calculated molecular mass of 31,966 Da and a pI of 5.74. PT32 was found to have two PY motifs and 12 proline-rich self-repeating motifs (YGXPPXG) in its C-terminal half.

BLAST Sequence Comparison of PT32 (Bovine)

Using sequence comparison software, PT32 cDNA was found to be novel The ORF of the bovine PT32 cDNA shares a global 62% nucleotide sequence identity (BLASTN 2.1.2, matrix blastn matrix: 1-3; gap penalties: existence=5, extension=2) with the ORF of mouse somatic WW domain binding protein 2 (WBP2, accession no. U40826, cloned from a mouse embryo cDNA library) (FIG. 3A, SEQ ID NO:17). The bovine PT32 cDNA sequence was also found to be similar to a recently identified mouse testicular cDNA (GenBank accession no. AK015863), as set forth in FIG. 3B as SEQ ID NO:18. The deduced amino acid sequence from this mouse sequence is 52.9% identical (LALIGN, University of Virginia, Charlottesville, Va.; scoring matrix, opening gap penalty=−14, extending gap penalty=−4) to the bovine PT32 amino acid sequence (67.7% similar if conserved amino acid residues are considered). In addition, the unique YGXPPXG motif and the PY motif are found in this testicular mouse sequence 5 and 6 times, respectively. Furthermore, the calculated molecular mass (36 kDa) of this mouse polypeptide is consistent with results obtained from immunoblotting of rodent proteins.

Bovine PT32 also shared sequence similarity with a previously uncharacterized and preliminary human DNA sequence localized to chromosome 22. This human cDNA (GenBank accession no. XM_001168) was designated human "WBP2-like" protein and is referred to herein as WBPH (FIG. 4A). PT32 and WBPH share 64.5% nucleotide and 54% amino acid sequence identities. WBPH represents only a partial sequence. As described above, primers obtained from the ends of this sequence were used for RT-PCR on total RNA from human testis, and a PCR product of approximately 1000 nucleotides was obtained. This product was cloned, sequenced, and termed human testicular WW domain Binding Protein (htWBP). htWBP has an ORF of 708 nucleotides, which encodes a polypeptide having a deduced amino acid sequence of 235 residues. Thus, htWBP is a more complete sequence than WBPH as it contains a stretch of 37 amino acids, amino acids 61 to 97 of SEQ ID NO:12, that is not present in WBPH (FIG. 4B).

Verification of PT32's Identity, Recombinant PT32 Protein and Antibody Production For confirmation of PT32's identity, antibodies were produced from two synthesized oligo-peptides chosen from the N-terminal (anti-oN32) and C-terminal (anti-oC32) ends of the deduced open reading frame of PT32 cDNA. In addition, antiserum to the recombinant PT32 (anti-rPT32) was produced. Anti-oN32 reacted specifically with the recombinant PT32 on Western blots. All three antibodies demonstrated a specific immunoreaction with a 32 kDa protein band on Western blots of bull PT NaOH extracts (step 3 of the extraction protocol described above).

The anti-rPT32 antiserum was then used to screen NaOH-extracted human sperm by Western blotting. The antiserum detected a prominent band at 30 kDa and a less prominent band at 32 kDa.

Ultrastructural Localization of PT32

Immunogold-labeling of cauda epididymal sperm sections with affinity-purified anti-rPT32 demonstrated that PT32 was found predominantly over the postacrosomal sheath of the mature bull sperm PT (FIGS. 5A-5D). Occasionally, labeling was found in the subacrosomal layer of the equatorial segment region. No immunoreactivity was apparent in any other sperm structures. An oblique section through the caudal face of the sperm head indicated that PT32 is evenly distributed through the postacrosomal sheath and has a surface orientation. Immunofluorescence confirmed PT32's presence in the postacrosomal sheath of bull spermatozoa (FIG. 6A) and showed similar localization in developing and mature primate sperm (FIGS. 6B and 6C).

Comparative Northern Blot Analysis

Northern blots of total RNA isolated from various bull tissues probed with DIG-labeled antisense RNA transcribed from PT32 cDNA showed the presence of a major 1.6 kb transcript only in the testis (FIG. 7A). No signals were detectable with sense riboprobes. A comparative northern blot of total RNA isolated from bull and human testis probed as described above showed that, in contrast to the major 1.6 kb transcript in the bull, there are two major transcripts of 1.6 and 2.4 kb in the human (FIG. 7B). The latter signal was barely detectable in the bull. The detection of the two PT32 transcripts in the human testis is coincident with the detection of two PT32 cross-reactive human PT polypeptides (FIG. 7B), suggestive of alternative splicing of the same transcript.

Developmental Northern Blot Analysis

The expression profile of PT32 transcript(s) was examined using total RNA obtained from rats at 14 to 49 days postpartum (FIGS. 7C-7E). In contrast to the 1.6 kb transcript in bull testis, two distinct transcripts of 2.4 and 4.0 kb were detected in rat testis. A barely detectable signal for both these mRNAs was detected at day 18, corresponding to a time in spermatogenesis when primary spermatocytes first appear. The signals then gradually intensified until 32 days postpartum, corresponding to the time of round spermatid development. On day 38, corresponding to the time of early elongated spermatids, the signal intensity of the two transcripts diminished and remained so into adulthood (day 49). The drop in PT32 mRNA levels at the elongated phase of spermiogenesis corresponds with the first appearance of PT32 protein, indicating that the message is translated at this time of spermiogenesis.

Protein Expression of PT32 During Spermatogenesis

Immunoperoxidase staining of the bull testicular paraffin sections with affinity-purified anti-rPT32 antibody was restricted to the elongated spermatid population found in the outermost layer of the seminiferous epithelium. No immunostaining was found in round spermatids. PT32 immunoreactivity was first detected in the cytoplasmic lobe of step 9 spermatids (stage IX) and gradually increased in intensity until step 12 spermatids (stage XII). Thereafter, immunostaining remained intense in the cytoplasmic lobe of steps 13 and 14 spermatids (stages I-V) until step 6 (stage VI), when the residual spermatid cytoplasm was phagocytosed as residual bodies by the Sertoli cells Immunogold labeling of EM testicular sections revealed that PT32 was deposited in the wake of the descending microtubular manchette as the postacrosomal sheath was being laid down in step 11 of spermiogenesis (stage XI). After the descent of the manchette and consequent assembly of the postacrosomal sheath by the time of step 13 spermatids (stage I), PT32 immunoreactivity was found throughout the postacrosomal sheath and in the caudal-most region of the subacrosomal layer adjacent to the forming equatorial segment. By the time the equatorial segment formed (thinned) in step 14 spermatids, only trace amounts of PT32 immunogold labeling remained in the subacrosomal layer adjacent to the equatorial segment, the majority of immunogold being over the postacrosomal sheath.

The Presence of PT32 in Various Sperm Extracts

Because freeze-thaw sperm extracts contain factor(s) that activate the oocyte, we determined whether PT32 is present in these extracts and how much is extracted relative to what remains on the sperm head. PT32 was found both in freeze-thaw extracts of bull sperm heads and in subsequent NaOH extracts. Based on the intensity of the immunoreaction, PT32 appeared more prominent in the NaOH extract than in the freeze-thaw extract, indicating that the freeze-thaw extraction partially releases PT32 from the PT. Freeze-thaw extracts of Rhesus monkey and human sperm were also immunoreactive to anti-PT32 antibodies.

The soluble portion of DTT-treated Triton-demembranated mouse sperm heads also contains factor(s) for oocyte activation. Thus, we determined whether PT32 is present in the DTT extract of bull sperm heads, and the relative amount extractable from the sperm head. Although PT32 was detected in the supernatant portion of the DTT extract, it appeared more abundant in the pellet. Thus, a reducing agent such as DTT can release PT32 from the PT.

Comparative Immunodetection of PT32 in Normal and Globozoospermic Human Sperm

An anti-rPT32 antibody was used in Western blot analyses of normal and globozoospermic human sperm samples. In the normal sperm controls, two signals were detected at 30 and 32 kDa. In the globozoospermic sperm, which are characterized by a round-acrosomeless sperm head, no immunosignal was detectable with the anti-rPT32 antibody.

Microinjection of rPT32 into Bovine Oocyte Cytoplasm

Injection of rPT32 into the cytoplasm of metaphase II-arrested oocytes (Table 1) yielded rates of oocyte activation (84.1% and 81.8% for two different concentrations) that were similar to the rate of activation of oocytes injected with perinuclear theca extracts (PTX; 84.1%), but that were significantly higher than the rate of activation of oocytes that did not receive an injection (36%).

TABLE 1

Injection of dialyzed, lyophilized rPT32 into bovine oocytes, scored at 40 hours after microinjection.

|  | M-II | PN | Cleavage | Total Act. | Total Ex. |
| --- | --- | --- | --- | --- | --- |
| rPT32 (2.5 pg) | 7 | 20 (45.5%) | 17 (38.6%) | 37 (84.1%) | 44 |
| rPT32 (0.25 pg) | 9 | 26 (53.1%) | 14 (28.6%) | 40 (81.8%) | 49 |
| PTX crude | 7 | 22 (50.0%) | 15 (34.1%) | 37 (84.1%) | 44 |
| No injection | 7 | 18 (15.8%) | 23 (20.2%) | 41 (36.0%) | 48 |

Data from 3 repeated assays are shown. Oocytes were cultured for 24 hours in fertilization medium then transferred to CR-1 medium for embryo culture.

The structural effects of rPT32 injection were determined in eggs that were fixed at 20 hours after fertilization, a stage at which full size pronuclei are seen in in vitro fertilized bovine oocytes and at which the oocytes are past S-phase entry (FIGS. 8A-8J). Injection of rPT32 or PT extracts induced the clustering of intrinsic c-Yes kinase in the oocyte cytoplasm. The uninjected, M-II-arrested oocytes displayed a diffuse, background-like cytoplasmic localization of c-Yes and a metaphase-arrangement of chromosomes. The oocytes that received microinjections of rPT32 displayed scattered foci of c-Yes throughout their cytoplasm, in addition to one or more pronuclei. Similarly, the injection of crude PT extracts caused pronuclear formation and c-Yes clustering, while the injection of a neutral protein, BSA-V, did not induce such an effect. Uninjected oocytes did not show clustering of cytoplasmic c-Yes or the formation of pronuclei after 20 hours of culture in fertilization medium. The c-Yes-containing oocyte-cytoplasmic foci overlapped with an endoplasmic reticulum (ER) marker, protein disulfide isomerase (PDI). Oocytes fertilized in vitro by sperm displayed cytoplasmic c-Yes foci similar to those seen in the rPT32-injected oocytes. Cytoplasmic annulate lamellae and nuclear pore complexes (NPC) on the nuclear envelope of the pronuclei were detected in rPT32-injected oocytes, consistent with the patterns of NPC turnover in normal, fertilized oocytes. The occurrence of c-Yes-positive foci in the cytoplasm of the injected oocytes was assessed after immunofluorescence labeling, and indicated that oocytes injected with rPT32 or PTX had a significantly higher level of cytoplasmic c-Yes recruitment to the ER.

Microinjection of Recombinant c-Yes into Bovine Oocyte Cytoplasm

The protein c-Yes is a Src-family tyrosine kinase that is naturally occurring in sperm PT. The amino acid sequence of an exemplary c-Yes protein is set forth in FIG. 10. Microinjection of c-Yes into bovine oocytes caused the oocytes to undergo cell cycle activation, pronuclear development and cortical granule exocytosis, all of which are hallmarks of oocyte activation (FIGS. 9A-9G). Co-injection of recombinant c-Yes (c-Yes$_r$) with recombinant PT32 further enhanced the rates of oocyte-activation and pronuclear development, while control oocytes that received injections of buffer without recombinant proteins did not become activated and displayed a metaphase-II arrangement of chromosomes along with intact cortical granules. Formation of the nuclear envelope with nuclear pore complexes (NPC) and the assembly of cytoplasmic NPC-containing annulate lamellae, which are landmarks of normal pronuclear development, were observed in bovine oocytes after the microinjection of c-Yes$_r$ or c-Yes$_r$ in combination with recombinant PT32. The exocytosis of cortical granules was evidenced by a reduction in LCA-labeling and a shift from a patchy to diffuse pattern of cortical granule distribution.

Developmentally, c-Yes is inserted into the bovine, human, and rhesus monkey perinuclear theca during spermatid elongation, a step at which spermatids acquire the ability to activate an oocyte upon being injected into its cytoplasm. By immunofluorescence, c-Yes labeling was detectable in elongating/elongated spermatids, testicular sperm, and ejaculated sperm. By immunofluorescence, c-Yes was absent in round spermatids and is not detectable in most ejaculated sperm prior to acrosome reaction, which was most likely due to post-translational modifications during epididymal sperm maturation. Ionomycin, which is a calcium-ionophore, induces the acrosome reaction and induces the unmasking of c-Yes in ejaculated rhesus monkey sperm. After culturing the sperm in the presence of 50 µM ionomycin, c-Yes was detectable by immunofluorescence. Sperm cultured for 30 minutes alone served as a control. In the absence of ionomycin, few sperm were labeled with anti-c-Yes antibodies. The unmasking of c-Yes in the sperm equatorial segment also occurs after the natural acrosome reaction, which is induced by the penetration of an oocyte's jelly coat, the zona pellucida.

c-Yes is also present in the cytosol of unfertilized oocytes. The binding of the sperm to the egg plasma membrane, the oolemma, or the injection of c-Yes$_r$ or c-Yes$_r$ in combination with recombinant PT32, induced c-Yes-containing foci in the oocyte cytoplasm which co-localized with the endoplasmic reticulum, a site of $Ca^{2+}$ release during oocyte activation. Few c-Yes-positive foci were detected in the cytoplasm of a metaphase-II-arrested oocyte, whereas an early-pronuclear stage oocyte showed an increase in the number of cytoplasmic c-Yes foci. Additionally, sperm bound to the surface of a fertilized oocyte at the sperm-oolemma binding stage showed intense labeling of c-Yes in their equatorial segment, and numerous c-Yes foci could be detected in the cytoplasm. In a lateral view of a rhesus spermatozoon at the time of sperm-oolemma binding, a reduction of c-Yes signal on the ventral, oolemma-touching, side of the spermatozoon could be detected.

In sum, the Src-family tyrosine kinase c-Yes naturally co-localizes with its co-factor analogue, PT32, in the equatorial segment of sperm PT. This part of the sperm head mediates the initial fusion with the oocyte. c-Yes can induce oocyte-activation alone or in combination with PT32, indicating that it is a sperm-borne oocyte activating factor or a component of the sperm borne oocyte activating factor(s).

Pronuclear Development and Cortical Granule Exocytosis after Injection of Recombinant c-Yes and PT32 into Oocytes Hyperstimulation of female rhesus monkeys exhibiting regular menstrual cycles was induced with exogenous gonadotropins. Beginning at menses, females were down-regulated by daily subcutaneous injections of a GnRH antagonist (Antide; Ares Serono, Aubonne, Switzerland; 0.5 mg/kg body weight) for 6 days. During this 6 day period, recombinant human follicle stimulating hormone (r-hFSH; Organon Inc., West Orange, N.J.; 30 IU, i.m.) was administered twice daily. This treatment was followed by 1, 2, or 3 days of treatment with r-hFSH and recombinant luteinizing hormone (r-hLH; Ares Serono; 30 IU each, i.m., twice daily). Ultrasonography was performed on day 7 of the stimulation to confirm an adequate follicular response.

When follicles 3-4 mm in diameter were observed, 1000 IU r-hCG (Serono, Randolph, Mass.) was injected i.m. for ovulation. Follicular aspiration was performed at 27 hours after administration of hCG. Oocytes were aspirated from follicles using a needle suction device lined with Teflon tubing. Briefly, a 10 mm trocar was placed through the abdominal wall, and a telescope was introduced. Ovaries were visualized by a monitor attached to the inserted telescope. Two small incisions in the skin were made to facilitate the insertion of 5 mm trocars bilaterally. Grasping forceps were introduced through each trocar to fix the ovary at two points. Subsequently, a 20 gauge stainless steel hypodermic needle with teflon tubing was attached to an OHMEDA vacuum regulator. The tubing was flushed with sterile TALP-HEPES, supplemented with 5 IU/mL heparin, and the tubing was then inserted through the abdominal wall and into each ovary. Using a continuous vacuum at approximately 40-60 mm Hg pressure, multiple individual follicles were aspirated into blood collection tubes containing 1 mL of TALP-HEPES medium supplemented with 5 IU/mL heparin and maintained at 37° C.

Collection tubes were immediately transported to a dedicated primate oocyte/zygote laboratory for oocyte recovery and evaluation of the maturation stage. The content of each collection tube was diluted in TALP-HEPES supplemented with 2 mg/mL hyaluronidase. Oocytes were rinsed and then transferred to pre-equilibrated CMRL medium containing 3 mg/mL BSA (CMRL-BSA) and supplemented with 10 mg/mL porcine FSH and 10 IU/mL hCG, prior to evaluation of maturational state. Metaphase II-arrested oocytes exhibiting expanded cumulus cells, a distinct perivitelline space, and a first polar body were maintained in CMRL-BSA for up to 8 hours before fertilization. Immature oocytes were matured in CMRL-BSA plus hormones for up to 24 hours.

Holding pipettes (outer diameter 100 µm; inner diameter 20 µm) and microinjection needles (O.D. 4-5 µm and I.D. 2-3 µm), with a 50° bevel and a short, sharp point (Humagen, Inc., Charlottesville, Va.) were prepared and mounted on a Nikon Diaphot microscope equipped with Narishige and Eppendorf micromanipulators and Hoffman modulation contrast (HMC) optics. Injections were carried out on a heated stage at 35° C. in TALP-HEPES medium. A 20 µl drop of PT extract or purified PT protein was placed next to the drop of TALP-HEPES medium with oocytes under mineral oil on a large Petri dish serving as a microinjection stage.

Approximately 5 picoliters of recombinant PT32, recombinant c-Yes, or a mixture of the two recombinant proteins (50/50 mix; conc. 1 mg/mL in KMH buffer; 78 mM KCl, 50 mM HEPES, 0.5 mM MgCl$_2$) were aspirated into the injection pipette. Oocytes were immobilized with the polar body at 12 o'clock, and the injection needle was inserted through the zona into oocyte cytoplasm. The oolemma was breached, and the extract was injected into the center of the cytoplasm. After injection, oocytes were incubated in 100 ml TALP drops at 37° C. in 5% CO$_2$ for 20 hours prior to assaying for oocyte activation. The oocytes were processed for epifluorescence microscopy with a mixture of a blue fluorescent DNA stain (DAPI) and a cortical granule-binding lectin (*Lens culinaris* agglutinin (LCA)) which was conjugated to a green fluorescent dye (FITC).

Oocytes were considered to be activated if they displayed activation-induced exocytosis of CG and either (i) a parthenogenetic female pronucleus or (ii) chromosomes arranged in anaphase or telophase of second meiosis. A control group of oocytes was injected with vehicle buffer alone (KMH; 78 mM KCl, 50 mM HEPES, 0.5 mM MgCl$_2$). The results obtained from three experiments are set forth in Tables 2-5. These experiments demonstrate that rhesus monkey oocytes are activated by (i) c-Yes alone, (ii) PT32 alone, and (iii) c-Yes and PT32 in combination.

TABLE 2

Experiment 1: Relative rates of pronuclear (PN) development and cortical granule (CG) exocytosis after intracytoplasmic injection of recombinant tyrosine kinase c-Yes and recombinant PT32 into rhesus monkey oocytes.*

| | M II | 1 PN | 2 PN | 3 or more PN | 2-cell** | Sum (%) activated | Sum injected | Diffuse | Rim |
|---|---|---|---|---|---|---|---|---|---|
| Ctrl | 7 | 0 | 0 | 0 | 0 | 0 (0) | 7 | 0 | 7 |
| c-Yes | 3 | 1 | 0 | 0 | 1 | 2 (40.0) | 5 | 2 | 3 |
| c-Yes/PT32 | 5 | 2 | 0 | 0 | 0 | 2 (28.6) | 7 | 2 | 5 |
| RPT32 | 1 | 0 | 0 | 0 | 4 | 4 (80.0) | 5 | 4 | 1 |
| No inj | 8 | 0 | 0 | 0 | 0 | 0 (0) | 8 | 0 | 8 | sum = 32

TABLE 3

Experiment 2: Relative rates of pronuclear (PN) development and cortical granule (CG) exocytosis after intracytoplasmic injection of recombinant tyrosine kinase c-Yes and recombinant PT32 into rhesus monkey oocytes.*

| | M II | AII-TII | 1 PN | 2 PN | 3 or more PN | 2-cell** | Sum (%) activated | Sum injected | Diffuse | Rim |
|---|---|---|---|---|---|---|---|---|---|---|
| Ctrl | 5 | 0 | 2 | 0 | 0 | 0 | 2 (28.6) | 7 | 0 | 7 |
| c-Yes | 1 | 3 | 2 | 0 | 1 | 0 | 6 (85.7) | 7 | 6 | 1 |
| c-Yes/PT32 | 1 | 0 | 2 | 0 | 0 | 0 | 2 (66.6) | 3 | 2 | 1 |
| RPT32 | 1 | 3 | 3 | 0 | 0 | 0 | 6 (85.7) | 7 | 6 | 1 |
| No inj | 2 | 0 | 1 | 0 | 0 | 0 | 1 (33.3) | 3 | 0 | 3 | sum = 27

TABLE 4

Total of experiments 1 and 2: Relative rates of pronuclear (PN) development and cortical granule (CG) exocytosis after intracytoplasmic injection of recombinant tyrosine kinase c-Yes and recombinant PT32 into rhesus monkey oocytes.*

| | M II | AII-TII | 1 PN | 2 PN | 3 or more PN | 2-cell** | Sum (%) activated | Sum injected | Diffuse | Rim |
|---|---|---|---|---|---|---|---|---|---|---|
| Ctrl | 12 | 0 | 2 | 0 | 0 | 0 | 2 (14.3) | 14 | 0 | 14 |
| c-Yes | 4 | 4 | 2 | 0 | 1 | 1 | 8 (66.7) | 12 | 8 | 4 |
| c-Yes/PT32 | 6 | 2 | 2 | 0 | 0 | 0 | 4 (40.0) | 10 | 4 | 6 |
| RPT32 | 2 | 3 | 3 | 0 | 0 | 4 | 10 (83.3) | 12 | 10 | 2 |
| No inj | 10 | 0 | 1 | 0 | 0 | 0 | 1 (9.1) | 11 | 0 | 11 | sum = 59

TABLE 5

Experiment 3: Relative rates of pronuclear (PN) development and cortical granule (CG) exocytosis after intracytoplasmic injection of recombinant tyrosine kinase c-Yes and recombinant PT32 into rhesus monkey oocytes that were aged and/or developmentally incompetent, resulting in some spontaneous activation (hence a relatively low success rate).*

| | M II | AII-TII | 1 PN | 2 PN | 3 or more PN | 2-cell** | Sum (%) activated | Sum injected | Diffuse | Rim |
|---|---|---|---|---|---|---|---|---|---|---|
| Ctrl | 3 | 0 | 1 | 0 | 0 | 3 | 4 (57.1) | 7 | 2 | 5 |
| c-Yes | 1 | 4 | 2 | 0 | 0 | 0 | 6 (85.7) | 7 | 6 | 1 |
| c-Yes/ PT32 | 2 | 0 | 3 | 0 | 0 | 0 | 3 (60.0) | 5 | 3 | 2 |
| RPT32 | 5 | 2 | 2 | 0 | 0 | 0 | 4 (44.4) | 9 | 5 | 4 |
| No inj | 3 | 0 | 2 | 0 | 0 | 0 | 1 (20.0) | 5 | 2 | 3 |
| | | | | | | | | sum = 33 | | |

*Oocytes were first scored for PN development by DIC microscopy 6 hours after microinjection and allowed to develop for another 24 hours. All of the activated oocytes shown in column "sum (%) activated" already had a pronucleus at this stage. The oocytes that became activated but did not cleave are shown as "1 PN." To confirm the presence of pronuclei or condensed chromosomes, the injected oocytes were labeled with DAPI (DNA stain). Oocytes were fixed and scored 30 hours after microinjection. M II = metaphase II; PN = pronucleus. Sum of activated oocytes includes all oocytes progressing beyond metaphase II. Vehicle buffer alone was injected into the control group (Ctrl). The classification of CG distribution is based on previous studies (Behalova et al., J. Reprod Fert. 11: 151-157 (1997); Terada et al., Mol. Reprod Dev. 56: 89-98 (2000)). In all cases, the eggs with one or more pronuclei displayed a diffuse distribution of CG, consistent with cortical granule exocytosis during oocyte activation. To visualize pronuclei or condensed chromosomes, the injected oocytes were labeled with DAPI (DNA stain). CG were visualized using *Lens culinaris agglutinin (LCA) conjugated with FITC. Oocytes were fixed and scored 30 hours after microinjection.*
**Two-cell embryos invariably showed signs of fragmentation.

What is claimed is:

1. A method for inducing oocyte activation, the method comprising contacting an oocyte with an effective amount of
   (a) an isolated polypeptide comprising:
      1) at least one of (i) the sequence PPPGY (SEQ ID NO: 1), and (ii) the sequence LPPAY (SEQ ID NO:2), and
      2) at least three domains, each domain comprising the sequence YGXPPXG (SEQ ID NO:3), wherein Y represents a Tyrosine residue, G represents a Glycine residue, L represents a Leucine residue, A represents an Alanine residue, X represents any amino acid residue, and P represents a Proline residue, said isolated polypeptide comprising an amino acid sequence having at least 75% sequence identity to the sequence of SEQ ID NO:5 or SEQ ID NO:12, and
   (b) globozoospermic sperm, round spermatids, or sperm, wherein said oocyte is activated.

2. A method for inducing oocyte activation, the method comprising contacting an oocyte with an effective amount of an isolated polypeptide comprising:
   1) at least one of (i) the sequence PPPGY (SEQ ID NO: 1), and (ii) the sequence LPPAY (SEQ ID NO:2), and
   2) at least three domains, each domain comprising the sequence YGXPPXG (SEQ ID NO:3), wherein Y represents a Tyrosine residue, G represents a Glycine residue, L represents a Leucine residue, A represents an Alanine residue, X represents any amino acid residue, and P represents a Proline residue,
wherein said isolated polypeptide comprises an amino acid sequence having at least 75% sequence identity to the sequence of SEQ ID NO:5 or SEQ ID NO:12, wherein said oocyte is activated.

3. The method of claim 1 or 2 further comprising contacting oocyte with tyrosine kinase c-Yes.

4. The method of claim 1 or 2, wherein the polypeptide comprises a sequence having at least 90% sequence identity to the sequence of SEQ ID NO:5 or a sequence having at least 90% sequence identity to the sequence of SEQ ID NO:12.

5. The method of claim 1 or 2, wherein the polypeptide comprises a sequence having at least 95% sequence identity to the sequence of SEQ ID NO:5 or a sequence having at least 95% sequence identity to the sequence of SEQ ID NO:12.

6. The method of claim 1 or 2, wherein the polypeptide comprises the sequence of SEQ ID NO:5 or the sequence of SEQ ID NO:12.

7. The method of claim 1 or 2, wherein the isolated polypeptide has a molecular weight of about 32 kDa.

8. The method of claim 1 or 2, wherein the isolated polypeptide comprises at least 10 domains, each domain comprising the sequence YGXPPXG (SEQ ID NO:3).

9. The method of claim 1 or 2, wherein the oocyte being activated is from a mammal.

10. The method of claim 9, wherein the mammal is a human.

11. The method of claim 9, wherein the mammal is selected from the group consisting of a bovine, a pig, a sheep, a mouse, a goat, a monkey and a horse.

12. A method for inducing oocyte activation, the method comprising contacting an oocyte with an effective amount of
    (a) an isolated polypeptide comprising the amino acid sequence of SEQ ID NO:18, and
    (b) globozoospermic sperm, round spermatids, or sperm, wherein said oocyte is activated.

13. A method for inducing oocyte activation, the method comprising contacting an oocyte with an effective amount of an isolated polypeptide comprising the amino acid sequence of SEQ ID NO:18, wherein said oocyte is activated.

* * * * *

SEQUENCE LISTING

<160> NUMBER OF SEQ ID NOS: 20

<210> SEQ ID NO 1
<211> LENGTH: 5
<212> TYPE: PRT
<213> ORGANISM: mammalian

<400> SEQUENCE: 1

Pro Pro Pro Gly Tyr
1               5

<210> SEQ ID NO 2
<211> LENGTH: 5
<212> TYPE: PRT
<213> ORGANISM: mammalian

<400> SEQUENCE: 2

Leu Pro Pro Ala Tyr
1               5

<210> SEQ ID NO 3
<211> LENGTH: 7
<212> TYPE: PRT
<213> ORGANISM: mammalian
<220> FEATURE:
<221> NAME/KEY: misc_feature
<222> LOCATION: (3)..(3)
<223> OTHER INFORMATION: X may be any amino acid residue
<220> FEATURE:

-continued

```
<221> NAME/KEY: misc_feature
<222> LOCATION: (6)..(6)
<223> OTHER INFORMATION: X may be any amino acid residue

<400> SEQUENCE: 3

Tyr Gly Xaa Pro Pro Xaa Gly
1               5

<210> SEQ ID NO 4
<211> LENGTH: 1413
<212> TYPE: DNA
<213> ORGANISM: mammalian
<220> FEATURE:
<221> NAME/KEY: CDS
<222> LOCATION: (36)..(974)
<223> OTHER INFORMATION:

<400> SEQUENCE: 4
cggcacgagg ggcggcagga gggggcctgg gcagg atg gca gtg aac cag agc         53
                                      Met Ala Val Asn Gln Ser
                                        1               5 cac acc gag agc cgt cgt ggg gcc ctc atc ccc tct ggc gaa agt gtc       101
His Thr Glu Ser Arg Arg Gly Ala Leu Ile Pro Ser Gly Glu Ser Val
             10                  15                  20 ttg aag cag tgt gag gat gtg gac ctc tgc ttc cta cag aaa cca gtg       149
Leu Lys Gln Cys Glu Asp Val Asp Leu Cys Phe Leu Gln Lys Pro Val
         25                  30                  35 gaa tcc tat ctc ttt aat ggc aca aag aaa gga acg ttg ttt ctc act       197
Glu Ser Tyr Leu Phe Asn Gly Thr Lys Lys Gly Thr Leu Phe Leu Thr
     40                  45                  50 tca tac cgg gtg gtc ttc gtg act tca cac tta gtc aat gac ccc atg       245
Ser Tyr Arg Val Val Phe Val Thr Ser His Leu Val Asn Asp Pro Met
 55                  60                  65                  70 ctt tct ttt atg atg ccg ttt ggc ctg atg agt gac tgc acc att gaa       293
Leu Ser Phe Met Met Pro Phe Gly Leu Met Ser Asp Cys Thr Ile Glu
                 75                  80                  85 caa cca att ttt gcc ccc aac tac att aaa gga acc att cag gca gct       341
Gln Pro Ile Phe Ala Pro Asn Tyr Ile Lys Gly Thr Ile Gln Ala Ala
             90                  95                 100 cca ggt ggt ggc tgg gaa gga caa gct gtt ttt aag tta tcc ttc agg       389
Pro Gly Gly Gly Trp Glu Gly Gln Ala Val Phe Lys Leu Ser Phe Arg
        105                 110                 115 aaa gga ggt gcc atc gaa ttt gcc caa ctg atg gta aaa gct gcc tct       437
Lys Gly Gly Ala Ile Glu Phe Ala Gln Leu Met Val Lys Ala Ala Ser
    120                 125                 130 gct gct gcc aga gga att cca ctt gga agt gta aat tac tgg ttc gac       485
Ala Ala Ala Arg Gly Ile Pro Leu Gly Ser Val Asn Tyr Trp Phe Asp
135                 140                 145                 150 act tca gga ctg tac ata att act gtc cca ggg gct gca gtg tgc tcc       533
Thr Ser Gly Leu Tyr Ile Ile Thr Val Pro Gly Ala Ala Val Cys Ser
                155                 160                 165 tca cag aca cct tgt cca gca tat cca att gtg atc tat gga ccc cca       581
Ser Gln Thr Pro Cys Pro Ala Tyr Pro Ile Val Ile Tyr Gly Pro Pro
            170                 175                 180 cca cca gga tat aca gtc caa cca ggg gaa tat gga act cca cca gaa       629
Pro Pro Gly Tyr Thr Val Gln Pro Gly Glu Tyr Gly Thr Pro Pro Glu
        185                 190                 195 gga tat gga gcc caa cca ggg gga tat gga gcc cca cct atg gga tat       677
Gly Tyr Gly Ala Gln Pro Gly Gly Tyr Gly Ala Pro Pro Met Gly Tyr
    200                 205                 210 gga gcc ccg cct gtg gga tat gga gtc cca cct ggg gga tat gga gtc       725
Gly Ala Pro Pro Val Gly Tyr Gly Val Pro Pro Gly Gly Tyr Gly Val
```

```
                215                 220                 225                 230
cca cct ggg gga tat gga gtc cca cct ggg gga tat gga gcc cca cct              773
Pro Pro Gly Gly Tyr Gly Val Pro Pro Gly Gly Tyr Gly Ala Pro Pro
                        235                 240                 245 ggg gga tat gga gtc cca cct ggg gga tat ggt gcc cca cct ggg gga              821
Gly Gly Tyr Gly Val Pro Pro Gly Gly Tyr Gly Ala Pro Pro Gly Gly
            250                 255                 260 tat gga gcc cca cct gca gga tat gga gcc cca cca gct gga aat gaa              869
Tyr Gly Ala Pro Pro Ala Gly Tyr Gly Ala Pro Pro Ala Gly Asn Glu
                265                 270                 275 gcc cta ccc cct gca tat gaa gct cca tct gct gga aat aca gct gcc              917
Ala Leu Pro Pro Ala Tyr Glu Ala Pro Ser Ala Gly Asn Thr Ala Ala
            280                 285                 290 tct cac aga tct atg aca gct cag cag gag act tct ctt ccc act acc              965
Ser His Arg Ser Met Thr Ala Gln Gln Glu Thr Ser Leu Pro Thr Thr
        295                 300                 305                 310 tca tct tct taggtccatt taccaccttc tcagagttaa accttgaaga                     1014
Ser Ser Ser ctcaccaagc aaagggcacc ctaaaactga agtcacagta agaaggaaga cccaggtgcc           1074
cagtggtagg aggtgttcgt gtgcacgcag tggtctgatc ttctccacac acctgtgagg          1134
tcctgtgcct caaaacagat gaaggtgaga agacgactcc tgttctcaag gaaggaagat          1194
gcttgaaaac agactgcaag ccaactagag agagagagat gtgaagtggc acataaaaca          1254
gcttggggat ggagactgac tctctttaga aaacaggcct tctccctgcc tctgacctga          1314
gcagaaaaga gaaatcgctg gaaccaaaga gctagggtca ccctgcttag acgccctcga          1374
ttaaagcctg cttgctgttg cataaaaaaa aaaaaaaaa                                 1413

<210> SEQ ID NO 5
<211> LENGTH: 313
<212> TYPE: PRT
<213> ORGANISM: mammalian

<400> SEQUENCE: 5

Met Ala Val Asn Gln Ser His Thr Glu Ser Arg Arg Gly Ala Leu Ile
1               5                   10                  15

Pro Ser Gly Glu Ser Val Leu Lys Gln Cys Glu Asp Val Asp Leu Cys
            20                  25                  30

Phe Leu Gln Lys Pro Val Glu Ser Tyr Leu Phe Asn Gly Thr Lys Lys
        35                  40                  45

Gly Thr Leu Phe Leu Thr Ser Tyr Arg Val Val Phe Val Thr Ser His
    50                  55                  60

Leu Val Asn Asp Pro Met Leu Ser Phe Met Met Pro Phe Gly Leu Met
65                  70                  75                  80

Ser Asp Cys Thr Ile Glu Gln Pro Ile Phe Ala Pro Asn Tyr Ile Lys
                85                  90                  95

Gly Thr Ile Gln Ala Ala Pro Gly Gly Gly Trp Glu Gly Gln Ala Val
            100                 105                 110

Phe Lys Leu Ser Phe Arg Lys Gly Gly Ala Ile Glu Phe Ala Gln Leu
        115                 120                 125

Met Val Lys Ala Ala Ser Ala Ala Ala Arg Gly Ile Pro Leu Gly Ser
    130                 135                 140

Val Asn Tyr Trp Phe Asp Thr Ser Gly Leu Tyr Ile Ile Thr Val Pro
145                 150                 155                 160

Gly Ala Ala Val Cys Ser Ser Gln Thr Pro Cys Pro Ala Tyr Pro Ile
                165                 170                 175
```

-continued

```
Val Ile Tyr Gly Pro Pro Pro Gly Tyr Thr Val Gln Pro Gly Glu
            180                 185                 190

Tyr Gly Thr Pro Pro Glu Gly Tyr Gly Ala Gln Pro Gly Gly Tyr Gly
        195                 200                 205

Ala Pro Pro Met Gly Tyr Gly Ala Pro Pro Val Gly Tyr Gly Val Pro
    210                 215                 220

Pro Gly Gly Tyr Gly Val Pro Gly Gly Tyr Gly Val Pro Pro Gly
225                 230                 235                 240

Gly Tyr Gly Ala Pro Pro Gly Gly Tyr Gly Val Pro Pro Gly Gly Tyr
                245                 250                 255

Gly Ala Pro Pro Gly Gly Tyr Gly Ala Pro Pro Ala Gly Tyr Gly Ala
            260                 265                 270

Pro Pro Ala Gly Asn Glu Ala Leu Pro Pro Ala Tyr Glu Ala Pro Ser
        275                 280                 285

Ala Gly Asn Thr Ala Ala Ser His Arg Ser Met Thr Ala Gln Gln Glu
    290                 295                 300

Thr Ser Leu Pro Thr Thr Ser Ser Ser
305                 310

<210> SEQ ID NO 6
<211> LENGTH: 24
<212> TYPE: PRT
<213> ORGANISM: mammalian

<400> SEQUENCE: 6

Thr Ser Tyr Arg Val Val Phe Val Thr Ser His Leu Val Asn Asp Pro
1               5                   10                  15

Met Leu Ser Phe Met Met Pro Phe
            20

<210> SEQ ID NO 7
<211> LENGTH: 16
<212> TYPE: PRT
<213> ORGANISM: mammalian

<400> SEQUENCE: 7

Asn Glu Ala Leu Pro Pro Ala Tyr Glu Ala Pro Ser Ala Gly Asn Thr
1               5                   10                  15

<210> SEQ ID NO 8
<211> LENGTH: 4
<212> TYPE: PRT
<213> ORGANISM: mammalian
<220> FEATURE:
<221> NAME/KEY: misc_feature
<222> LOCATION: (3)..(3)
<223> OTHER INFORMATION: X may be any amino acid

<400> SEQUENCE: 8

Pro Pro Xaa Tyr
1

<210> SEQ ID NO 9
<211> LENGTH: 239
<212> TYPE: PRT
<213> ORGANISM: Bos sp.

<400> SEQUENCE: 9

Met Pro Phe Gly Leu Met Ser Asp Cys Thr Ile Glu Gln Pro Ile Phe
1               5                   10                  15
```

```
Ala Pro Asn Tyr Ile Lys Gly Thr Ile Gln Ala Ala Pro Gly Gly Gly
            20                  25                  30

Trp Glu Gly Gln Ala Val Phe Lys Leu Ser Phe Arg Lys Gly Gly Ala
        35                  40                  45

Ile Glu Phe Ala Gln Leu Met Val Lys Ala Ala Ser Ala Ala Ala Arg
 50                  55                  60

Gly Ile Pro Leu Gly Ser Val Asn Tyr Trp Phe Asp Thr Ser Gly Leu
 65                  70                  75                  80

Tyr Ile Ile Thr Val Pro Gly Ala Ala Val Cys Ser Ser Gln Thr Pro
                85                  90                  95

Cys Pro Ala Tyr Pro Ile Val Ile Tyr Gly Pro Pro Pro Gly Tyr
                100                 105                 110

Thr Val Gln Pro Gly Glu Tyr Gly Thr Pro Pro Glu Gly Tyr Gly Ala
            115                 120                 125

Gln Pro Gly Gly Tyr Gly Ala Pro Pro Met Gly Tyr Gly Ala Pro Pro
130                 135                 140

Val Gly Tyr Gly Val Pro Pro Gly Gly Tyr Gly Val Pro Pro Gly Gly
145                 150                 155                 160

Tyr Gly Val Pro Pro Gly Gly Tyr Gly Ala Pro Pro Gly Gly Tyr Gly
                165                 170                 175

Val Pro Pro Gly Gly Tyr Gly Ala Pro Pro Gly Gly Tyr Gly Ala Pro
                180                 185                 190

Pro Ala Gly Tyr Gly Ala Pro Pro Ala Gly Asn Glu Ala Leu Pro Pro
            195                 200                 205

Ala Tyr Glu Ala Pro Ser Ala Gly Asn Thr Ala Ala Ser His Arg Ser
        210                 215                 220

Met Thr Ala Gln Gln Glu Thr Ser Leu Pro Thr Thr Ser Ser Ser
225                 230                 235

<210> SEQ ID NO 10
<211> LENGTH: 225
<212> TYPE: PRT
<213> ORGANISM: Homo sapiens

<400> SEQUENCE: 10

Met Pro Phe Asp Leu Met Thr Asn Leu Thr Val Glu Gln Pro Val Phe
 1               5                  10                  15

Ala Ala Asn Phe Ile Lys Gly Thr Ile Gln Ala Ala Pro Tyr Gly Gly
            20                  25                  30

Trp Glu Gly Gln Ala Thr Phe Lys Leu Val Phe Arg Asn Gly Asp Ala
        35                  40                  45

Ile Glu Phe Ala Gln Leu Met Val Lys Ala Ala Ser Ala Val Ile Val
 50                  55                  60

Tyr Gly Ala Pro Pro Ala Gly Tyr Gly Ala Pro Pro Gly Tyr Gly
 65                  70                  75                  80

Ala Pro Pro Ala Gly Tyr Gly Ala Gln Pro Val Gly Asn Glu Gly Pro
                85                  90                  95

Pro Val Gly Tyr Arg Ala Ser Pro Val Arg Tyr Gly Ala Pro Pro Leu
                100                 105                 110

Gly Tyr Gly Ala Pro Pro Ala Gly Tyr Gly Ala Pro Pro Leu Gly Tyr
            115                 120                 125

Gly Ala Pro Pro Leu Gly Tyr Gly Thr Pro Pro Leu Gly Tyr Gly Ala
            130                 135                 140

Pro Pro Leu Gly Tyr Gly Ala Pro Pro Ala Gly Asn Glu Gly Pro Pro
145                 150                 155                 160
```

```
Ala Gly Tyr Arg Ala Ser Pro Ala Gly Ser Gly Ala Arg Pro Gln Glu
            165                 170                 175

Ser Thr Ala Ala Gln Ala Pro Glu Asn Glu Ala Ser Leu Pro Ser Ala
        180                 185                 190

Ser Ser Ser Gln Asp Lys Glu Asp Ser Gly Gln Pro Phe Leu Arg
    195                 200                 205

Lys Ser Ala Phe Gln Cys Leu Leu Glu Cys Asp Asp Tyr Leu Ile Val
        210                 215                 220

Arg
225

<210> SEQ ID NO 11
<211> LENGTH: 1001
<212> TYPE: DNA
<213> ORGANISM: Homo sapiens
<220> FEATURE:
<221> NAME/KEY: CDS
<222> LOCATION: (1)..(708)
<223> OTHER INFORMATION:

<400> SEQUENCE: 11 atg cca ttt gat ctg atg acg aac ctc act gtt gaa caa cca gta ttt    48
Met Pro Phe Asp Leu Met Thr Asn Leu Thr Val Glu Gln Pro Val Phe
1               5                   10                  15 gct gca aac ttc att aag gga act att cag gca gct cca tat ggt ggc    96
Ala Ala Asn Phe Ile Lys Gly Thr Ile Gln Ala Ala Pro Tyr Gly Gly
            20                  25                  30 tgg gaa gga caa gct act ttt aaa tta gtc ttc aga aat gga gat gcc    144
Trp Glu Gly Gln Ala Thr Phe Lys Leu Val Phe Arg Asn Gly Asp Ala
        35                  40                  45 att gaa ttt gcc cag ttg atg gtg aaa gct gcc tct gct gtt gcc cga    192
Ile Glu Phe Ala Gln Leu Met Val Lys Ala Ala Ser Ala Val Ala Arg
    50                  55                  60 gga ttt cca ctt aga acc tta aat gac tgg ttc agc tct atg gga att    240
Gly Phe Pro Leu Arg Thr Leu Asn Asp Trp Phe Ser Ser Met Gly Ile
65                  70                  75                  80 tat gta att act ggg gaa ggg aat atg tgc act cca cag atg cct tgt    288
Tyr Val Ile Thr Gly Glu Gly Asn Met Cys Thr Pro Gln Met Pro Cys
                85                  90                  95 tca gtt att gtc tat ggg gcc cca cct gca gga tat gga gcc cca cct    336
Ser Val Ile Val Tyr Gly Ala Pro Pro Ala Gly Tyr Gly Ala Pro Pro
            100                 105                 110 ccc gga tac gga gcc cca cct gca gga tat gga gcc caa ccc gta gga    384
Pro Gly Tyr Gly Ala Pro Pro Ala Gly Tyr Gly Ala Gln Pro Val Gly
        115                 120                 125 aat gaa ggc ccg cct gtg gga tac aga gcc tca cct gtg cga tat gga    432
Asn Glu Gly Pro Pro Val Gly Tyr Arg Ala Ser Pro Val Arg Tyr Gly
    130                 135                 140 gcc cca cct ctt gga tac gga gcc cca cct gca gga tat gga gcc cca    480
Ala Pro Pro Leu Gly Tyr Gly Ala Pro Pro Ala Gly Tyr Gly Ala Pro
145                 150                 155                 160 cct cta gga tat gga gcc cca cct ctt gga tat gga acc cca cct ctc    528
Pro Leu Gly Tyr Gly Ala Pro Pro Leu Gly Tyr Gly Thr Pro Pro Leu
                165                 170                 175 gga tat gga gcc cca cct ctc gga tat gga gcc cca cct gca gga aat    576
Gly Tyr Gly Ala Pro Pro Leu Gly Tyr Gly Ala Pro Pro Ala Gly Asn
            180                 185                 190 gaa ggc ccg cct gcg gga tac aga gcc tca cct gct gga tca gga gcc    624
Glu Gly Pro Pro Ala Gly Tyr Arg Ala Ser Pro Ala Gly Ser Gly Ala
        195                 200                 205
```

-continued

```
agg cct cag gaa tct aca gca gcc cag gct cct gaa aac gag gct tct      672
Arg Pro Gln Glu Ser Thr Ala Ala Gln Ala Pro Glu Asn Glu Ala Ser
    210                 215                 220 ctt ccc tct gcc tcc tct tct cag gtc cat tct taa ccttctaaga           718
Leu Pro Ser Ala Ser Ser Ser Gln Val His Ser
225                 230                 235 tgtaaacctt gaagactcac caagcaaaga ggtaccctaa aattgaagtc aggataagga    778
ggacgactca gcttagagtc attgattgat ctgcattgtg aaaattagga aaccagatgc    838
tcccatgttc tcaaggacga cctttcttaa ggaagtcagt acgtgggcaa cagtgatgag    898
aggaagagag gagagactca accaactaga gcagggataa ggtttccctt gttcagcttt    958
tcagtgtctg ctggaatgtg atgattacct cattgtcagg tag                     1001
```

```
<210> SEQ ID NO 12
<211> LENGTH: 235
<212> TYPE: PRT
<213> ORGANISM: Homo sapiens

<400> SEQUENCE: 12

Met Pro Phe Asp Leu Met Thr Asn Leu Thr Val Glu Gln Pro Val Phe
1               5                   10                  15

Ala Ala Asn Phe Ile Lys Gly Thr Ile Gln Ala Ala Pro Tyr Gly Gly
                20                  25                  30

Trp Glu Gly Gln Ala Thr Phe Lys Leu Val Phe Arg Asn Gly Asp Ala
            35                  40                  45

Ile Glu Phe Ala Gln Leu Met Val Lys Ala Ala Ser Ala Val Ala Arg
        50                  55                  60

Gly Phe Pro Leu Arg Thr Leu Asn Asp Trp Phe Ser Ser Met Gly Ile
65                  70                  75                  80

Tyr Val Ile Thr Gly Glu Gly Asn Met Cys Thr Pro Gln Met Pro Cys
                85                  90                  95

Ser Val Ile Val Tyr Gly Ala Pro Ala Gly Tyr Gly Ala Pro Pro
                100                 105                 110

Pro Gly Tyr Gly Ala Pro Pro Ala Gly Tyr Gly Ala Gln Pro Val Gly
            115                 120                 125

Asn Glu Gly Pro Pro Val Gly Tyr Arg Ala Ser Pro Val Arg Tyr Gly
        130                 135                 140

Ala Pro Pro Leu Gly Tyr Gly Ala Pro Ala Gly Tyr Gly Ala Pro
145                 150                 155                 160

Pro Leu Gly Tyr Gly Ala Pro Pro Leu Gly Tyr Gly Thr Pro Pro Leu
                165                 170                 175

Gly Tyr Gly Ala Pro Pro Leu Gly Tyr Gly Ala Pro Ala Gly Asn
            180                 185                 190

Glu Gly Pro Pro Ala Gly Tyr Arg Ala Ser Pro Ala Gly Ser Gly Ala
        195                 200                 205

Arg Pro Gln Glu Ser Thr Ala Ala Gln Ala Pro Glu Asn Glu Ala Ser
    210                 215                 220

Leu Pro Ser Ala Ser Ser Ser Gln Val His Ser
225                 230                 235
```

```
<210> SEQ ID NO 13
<211> LENGTH: 22
<212> TYPE: DNA
<213> ORGANISM: Artificial Sequence
<220> FEATURE:
<223> OTHER INFORMATION: primer
```

-continued

<400> SEQUENCE: 13
ggcagggatg gcagtgaacc ag    22

<210> SEQ ID NO 14
<211> LENGTH: 23
<212> TYPE: DNA
<213> ORGANISM: Artificial Sequence
<220> FEATURE:
<223> OTHER INFORMATION: primer

<400> SEQUENCE: 14
gtccatttac caccttctca gag    23

<210> SEQ ID NO 15
<211> LENGTH: 18
<212> TYPE: DNA
<213> ORGANISM: Artificial Sequence
<220> FEATURE:
<223> OTHER INFORMATION: primer

<400> SEQUENCE: 15
atgccatttg atctgatg    18

<210> SEQ ID NO 16
<211> LENGTH: 18
<212> TYPE: DNA
<213> ORGANISM: Artificial Sequence
<220> FEATURE:
<223> OTHER INFORMATION: primer

<400> SEQUENCE: 16
atggagtaac agtccatc    18

<210> SEQ ID NO 17
<211> LENGTH: 166
<212> TYPE: PRT
<213> ORGANISM: Mus sp.

<400> SEQUENCE: 17

Met Ala Leu Asn Lys Asn His Ser Glu Gly Gly Val Ile Val Asn
1               5                   10                  15

Asn Thr Glu Ser Ile Leu Met Ser Tyr Asp His Val Glu Leu Thr Phe
            20                  25                  30

Asn Asp Met Lys Asn Val Pro Glu Ala Phe Lys Gly Thr Lys Lys Gly
        35                  40                  45

Thr Val Tyr Leu Thr Pro Tyr Arg Val Ile Phe Leu Ser Lys Gly Lys
    50                  55                  60

Asp Ala Met Gln Ser Phe Met Met Pro Phe Tyr Leu Met Lys Asp Cys
65                  70                  75                  80

Glu Ile Lys Gln Pro Val Phe Gly Ala Asn Phe Ile Lys Gly Ile Val
                85                  90                  95

Lys Ala Glu Ala Gly Gly Gly Trp Glu Gly Ser Ala Ser Tyr Lys Leu
            100                 105                 110

Thr Phe Thr Ala Gly Gly Ala Ile Glu Phe Gly Gln Arg Met Leu Gln
        115                 120                 125

Val Ala Ser Gln Ala Ser Arg Gly Glu Val Pro Asn Gly Ala Tyr Gly
    130                 135                 140

Tyr Pro Tyr Met Pro Ser Gly Ala Tyr Val Phe Pro Pro Val Ala
145                 150                 155                 160

Asn Gly Met Tyr Pro Cys
              165

<210> SEQ ID NO 18
<211> LENGTH: 359
<212> TYPE: PRT
<213> ORGANISM: Mus sp.

<400> SEQUENCE: 18

Met Ala Val Asn Gln Asn His Thr Val Asp Arg Arg Trp Ala Ala Ile
1               5                   10                  15
Pro His Gly Glu Ser Leu Leu Lys Lys Cys Ser Glu Val Asp Leu Ser
            20                  25                  30
Phe Pro Gln Ser Pro Pro Gly Ser Asn Leu Phe Ser Gly Thr Lys Arg
        35                  40                  45
Gly Ala Leu Phe Leu Thr Ser Tyr Arg Val Ile Phe Val Thr Ser Arg
    50                  55                  60
Ala Asp Asn Asp Pro Met Phe Ser Phe Thr Met Pro Phe His Leu Met
65                  70                  75                  80
Asn Asn Cys Thr Val Glu Gln Pro Ile Phe Gly Ala Asn Tyr Ile Lys
                85                  90                  95
Gly Thr Ile Gln Ala Ala Pro Asp Gly Gly Trp Glu Gly Ser Ala Thr
            100                 105                 110
Phe Lys Ile Val Phe Arg Lys Gly Gly Ala Ile Asp Phe Ala Gln Leu
        115                 120                 125
Met Ala Lys Ala Ala Ser Ala Ala Gln Gly Val Pro Leu Arg Val
    130                 135                 140
Ala Ser Phe Trp Met Gly Pro Leu Gly Ile Tyr Val Ile Thr Gly Asp
145                 150                 155                 160
Arg Asn Met Tyr Ala Pro Gln Ala Tyr Gln Val Ala Tyr Gly Ala Pro
                165                 170                 175
Pro Ala Gly Tyr Gly Ala Ser Pro Val Gly Tyr Gly Val Pro Ser Ala
            180                 185                 190
Gly Tyr Gly Ala Pro Pro Ala Gly Tyr Gly Ala Pro Pro Val Gly Tyr
        195                 200                 205
Val Ala Pro Ser Pro Gly Tyr Asp Val Leu Pro Pro Gly Tyr Gly Ala
    210                 215                 220
Val Arg Tyr Gly Ser Pro Pro Leu Tyr Val Ala Thr Pro Met Gly
225                 230                 235                 240
Tyr Gly Val Pro Pro Gly Tyr Gly Pro Pro Val Arg Tyr Gly
                245                 250                 255
Ser Pro Pro Gly Tyr Glu Ala Pro Thr Met Glu Tyr Gly Ala Gln
            260                 265                 270
Pro Pro Arg Tyr Gly Thr Thr Pro Met Gly Ser Gly Ser Pro Pro Pro
        275                 280                 285
Arg Tyr Glu Ala Pro Pro Met Gly Tyr Gly Thr Pro Pro Ser Gly Arg
    290                 295                 300
Glu Ser Ile Pro Pro Gly Ser Arg Ala Thr Ser Val Ala Gln Glu Ala
305                 310                 315                 320
Pro Pro Ala Gly Ser Glu Ala Gly His Pro Met Ser Val Ala Val Gln
                325                 330                 335
Asn Pro Glu Phe Gln Ala Ser Phe Pro Ser Thr Ser Ser Ser Gln Val
            340                 345                 350
His Ser Pro Arg Ser Lys Met
        355

```
<210> SEQ ID NO 19
<211> LENGTH: 171
<212> TYPE: PRT
<213> ORGANISM: Bos sp.

<400> SEQUENCE: 19

Met Ala Val Asn Gln Ser His Thr Glu Ser Arg Arg Gly Ala Leu Ile
1               5                   10                  15

Pro Ser Gly Glu Ser Val Leu Lys Gln Cys Glu Asp Val Asp Leu Cys
            20                  25                  30

Phe Leu Gln Lys Pro Val Glu Ser Tyr Leu Phe Asn Gly Thr Lys Lys
        35                  40                  45

Gly Thr Leu Phe Leu Thr Ser Tyr Arg Val Val Phe Val Thr Ser His
    50                  55                  60

Leu Val Asn Asp Pro Met Leu Ser Phe Met Met Pro Phe Gly Leu Met
65                  70                  75                  80

Ser Asp Cys Thr Ile Glu Gln Pro Ile Phe Ala Pro Asn Tyr Ile Lys
                85                  90                  95

Gly Thr Ile Gln Ala Ala Pro Gly Gly Gly Trp Glu Gly Gln Ala Val
            100                 105                 110

Phe Lys Leu Ser Phe Arg Lys Gly Gly Ala Ile Glu Phe Ala Gln Leu
        115                 120                 125

Met Val Lys Ala Ala Ser Ala Ala Arg Gly Ile Pro Leu Gly Ser
    130                 135                 140

Val Asn Tyr Trp Phe Asp Thr Ser Gly Leu Tyr Ile Ile Thr Val Pro
145                 150                 155                 160

Gly Ala Ala Val Cys Ser Ser Gln Thr Pro Cys
                165                 170

<210> SEQ ID NO 20
<211> LENGTH: 541
<212> TYPE: PRT
<213> ORGANISM: mammalian

<400> SEQUENCE: 20

Met Gly Cys Ile Lys Ser Lys Glu Asp Lys Gly Pro Ala Met Lys Tyr
1               5                   10                  15

Arg Thr Asp Asn Thr Pro Glu Pro Ile Ser Ser His Val Ser His Tyr
            20                  25                  30

Gly Ser Asp Ser Ser Gln Ala Thr Gln Ser Pro Ala Ile Lys Gly Ser
        35                  40                  45

Ala Val Asn Phe Asn Ser His Ser Met Thr Pro Phe Gly Gly Pro Ser
    50                  55                  60

Gly Met Thr Pro Phe Gly Gly Ala Ser Ser Phe Ser Ala Val Pro
65                  70                  75                  80

Ser Pro Tyr Pro Ser Thr Leu Thr Gly Gly Val Thr Val Phe Val Ala
                85                  90                  95

Leu Tyr Asp Tyr Glu Ala Arg Thr Thr Asp Asp Leu Ser Phe Lys Lys
            100                 105                 110

Gly Glu Arg Phe Gln Ile Ile Asn Asn Thr Glu Gly Asp Trp Trp Glu
        115                 120                 125

Ala Arg Ser Ile Ala Thr Gly Lys Thr Gly Tyr Ile Pro Ser Asn Tyr
    130                 135                 140

Val Ala Pro Ala Asp Ser Ile Gln Ala Glu Glu Trp Tyr Phe Gly Lys
145                 150                 155                 160
```

```
Met Gly Arg Lys Asp Ala Glu Arg Leu Leu Asn Pro Gly Asn Gln
            165                 170                 175

Arg Gly Ile Phe Leu Val Arg Glu Ser Glu Thr Thr Lys Gly Ala Tyr
            180                 185                 190

Ser Leu Ser Ile Arg Asp Trp Asp Glu Val Arg Gly Asp Asn Val Lys
            195                 200                 205

His Tyr Lys Ile Arg Lys Leu Asp Asn Gly Gly Tyr Tyr Ile Thr Thr
            210                 215                 220

Arg Ala Gln Phe Glu Ser Leu Gln Lys Leu Val Lys His Tyr Arg Glu
225                 230                 235                 240

His Ala Asp Gly Leu Cys His Lys Leu Thr Thr Val Cys Pro Thr Val
            245                 250                 255

Lys Pro Gln Thr Gln Gly Leu Ala Lys Asp Ala Trp Glu Ile Pro Arg
            260                 265                 270

Glu Ser Leu Arg Leu Glu Val Lys Leu Gly Gln Gly Cys Phe Gly Glu
            275                 280                 285

Val Trp Met Gly Thr Trp Asn Gly Thr Thr Lys Val Ala Ile Lys Thr
            290                 295                 300

Leu Lys Pro Gly Thr Met Met Pro Glu Ala Phe Leu Gln Glu Ala Gln
305                 310                 315                 320

Ile Met Lys Lys Leu Arg His Asp Lys Leu Val Pro Leu Tyr Ala Val
            325                 330                 335

Val Ser Glu Glu Pro Ile Tyr Ile Val Thr Glu Phe Met Thr Lys Gly
            340                 345                 350

Ser Leu Leu Asp Phe Leu Lys Glu Gly Glu Gly Lys Phe Leu Lys Leu
            355                 360                 365

Pro Gln Leu Val Asp Met Ala Ala Gln Ile Ala Asp Gly Met Ala Tyr
            370                 375                 380

Ile Glu Arg Met Asn Tyr Ile His Arg Asp Leu Arg Ala Ala Asn Ile
385                 390                 395                 400

Leu Val Gly Asp Asn Leu Val Cys Lys Ile Ala Asp Phe Gly Leu Ala
            405                 410                 415

Arg Leu Ile Glu Asp Asn Glu Tyr Thr Ala Arg Gln Gly Ala Lys Phe
            420                 425                 430

Pro Ile Lys Trp Thr Ala Pro Glu Ala Ala Leu Tyr Gly Arg Phe Thr
            435                 440                 445

Ile Lys Ser Asp Val Trp Ser Phe Gly Ile Leu Leu Thr Glu Leu Val
            450                 455                 460

Thr Lys Gly Arg Val Pro Tyr Pro Gly Met Val Asn Arg Glu Val Leu
465                 470                 475                 480

Glu Gln Val Glu Arg Gly Tyr Arg Met Pro Cys Pro Gln Gly Cys Pro
            485                 490                 495

Glu Ser Leu His Glu Leu Met Lys Leu Cys Trp Lys Lys Asp Pro Asp
            500                 505                 510

Glu Arg Pro Thr Phe Glu Tyr Ile Gln Ser Phe Leu Glu Asp Tyr Phe
            515                 520                 525

Thr Ala Thr Glu Pro Gln Tyr Gln Pro Gly Asp Asn Leu
530                 535                 540
```